(12) United States Patent
Hua et al.

(10) Patent No.: US 7,138,496 B2
(45) Date of Patent: Nov. 21, 2006

(54) HUMAN MONOCLONAL ANTIBODIES AGAINST HUMAN CXCR4

(75) Inventors: Shaobing Hua, Cupertino, CA (US); Michelle Haynes Pauling, San Mateo, CA (US); Li Zhu, Palo Alto, CA (US)

(73) Assignee: Genetastix Corporation, San Jose, CA (US)

( * ) Notice: Subject to any disclaimer, the term of this patent is extended or adjusted under 35 U.S.C. 154(b) by 616 days.

(21) Appl. No.: 10/360,828

(22) Filed: Feb. 7, 2003

(65) Prior Publication Data

US 2003/0206909 A1    Nov. 6, 2003

Related U.S. Application Data

(63) Continuation-in-part of application No. 10/133,978, filed on Apr. 25, 2002, now abandoned, which is a continuation-in-part of application No. 10/072,301, filed on Feb. 8, 2002, now Pat. No. 7,005,503, and a continuation-in-part of application No. 10/071,866, filed on Feb. 8, 2002, now abandoned.

(51) Int. Cl.
*C07K 16/00* (2006.01)
*C12P 21/08* (2006.01)

(52) U.S. Cl. ............... 530/387.1; 530/387.3; 530/387.9; 530/388.1; 530/388.2; 530/388.22; 530/388.7; 530/388.8; 530/389.7

(58) Field of Classification Search .......... None
See application file for complete search history.

(56) References Cited

U.S. PATENT DOCUMENTS 5,994,515 A  *  11/1999  Hoxie .......... 530/388.22

FOREIGN PATENT DOCUMENTS

WO    WO 99/ 50461    *  3/1999
WO    WO 01/79229     * 10/2001

OTHER PUBLICATIONS

Lederman et al. Molecular Immunology 1991. 28: 1171-1181.*
Li et al. PNAS 1980. 77: 3211-3214.*

* cited by examiner

*Primary Examiner*—Phillip Gambel
*Assistant Examiner*—Chun Crowder
(74) *Attorney, Agent, or Firm*—Wilson Sonsini Goodrich & Rosati

(57) ABSTRACT

Compositions are provided that comprise antibody against membrane proteins such as chemokine receptors. In particular, monoclonal human antibodies against human CXCR4 are provided that are capable of inhibiting HIV infection and chemotaxis in human breast cancer cells. The antibodies can be used as prophylactics or therapeutics to prevent and treat HIV infection and cancer, for screening drugs, and for diagnosing diseases or conditions associated with interactions with chemokine receptors.

5 Claims, 20 Drawing Sheets

FIGURE 1A

Amino acid sequence of human CCR5 [SEQ ID NO: 1]:

```
  1  MDYQVSSPIY DINYYTSEPC QKINVKQIAA RLLPPLYSLV FIFGFVGNML VILILINCKR
        N-Terminus                    Transmembrane Domain 1

61  LKSMTDIYLL NLAISDLFFL LTVPFWAHYA AAQWDFGNTM CQLLTGLYFI GFFSGIFFII
       LOOP 1    Transmembrane Domain 2    Loop 2    Transmembrane Domain 3

121  LLTIDRYLAV VHAVFALKAR TVTFGVVTSV ITWVVAVFAS LPGIIFTRSQ KEGLHYTCSS
       Loop 3       Transmembrane Domain 4                    Loop 4

181  HFPYSQYQFW KNFQTLKIVI LGLVLPLLVM VICYSGILKT LLRCRNEKKR HRAVRLIFTI
                  Transmembrane Domain 5              Loop 5

241  MIVYFLFWAP YNIVLLLNTF QEFFGLNNCS SSNRLDQAMQ VTETLGMTHC CINPIIYAFV
       Transmembrane Domain 6    Loop 6        Transmembrane Domain 7

301  GEKFRNYLLV FFQKHIAKRF CKCCSIFQQE APERASSVYT RSTGEQEISV GL
                           C-Terminus
```

FIGURE 1B

Peptide fragments derived from human CCR5 that are used as target peptides:

N-terminal fragment [SEQ ID NO: 8]:

MDYQVSSPIYDINYYTSEPCQKINVKQIAARLLPPL

Loop 4 fragment [SEQ ID NO: 9]:

TRSQKEGLHYTCSSHFPYSQYQFWKNFQTLKI

Loop 6 fragment [SEQ ID NO: 3]:

EFFGLNNCSSSNRLDQAMQVTETLGMTHC

A model of the secondary structure of human CCR5:

FIGURE 5

DNA sequence of clone 15.186.35 scFv against N-terminus fragment of human CCR5 [SEQ ID NO: 16]:

CAGGTTACCTTGAAGGAGTCTGGTCCTACGTTGGTGAAACCCACACAGACCCTCACGCTGACCTGCACCTTGTCTGGGTT
CTCACTCAGCACTAGTGGAGTGAGTGTGGGCTGGATCCGTCAGCCCCAGGAAAGGCCCTTGAGTGGCTTGCAAGCATAA
ATTGGAATGATGATAAGTGCTACAGCCCATCTCTGAAAAGCAGGCTCACCATCACCAAGgACACCCCCaAAAACCAGGTG
GTCCTTGCAATGAGCAACATGGACCCTGCGGACACAGCCACATATTCCTGTGCACTCGATATGCCCCCCCATGATAGTGG
CCCGCAATCTTTTGATGCTTCTGATGTCTGGGGCCCAGGGACAATGGTCACCGTCTCTTCAGGCGGTGGTGGATCAGGCG
GCGGAGGATCTGGCGGAGGTGGCAGCGGTGGTGGAGGCAGTTCCTATGAGCTGATGCAGCTACCCTCAGTGTCCGTGTCC
CCAGGACAGACAGCCAGCATCACCTGCTCTGGAGATAATTTGGGGGATAAATATGCCTGCTGGTATCAACAGAAGCCAGG
CCGGTCCCCTGTGCTGGTCATTTATGGAGATAACAAGCGGCCCTCAGGGATCCCTGAGCGATTCTCTGGCTCCAACTCTG
GGAACACAGCCACTCTGACCATCAGCGGGACCCAGGCTATGGATGAGGCTGACTATTACTGTCAGGCGTGGGACACCAGC
ACTGCTGTCTTCGGAACTGGGACCAAGCTCACCGTCCTA

Amino acid sequence of clone 15.186.35 scFv against N-terminus fragment of human CCR5 [SEQ ID NO: 17]:

QVTLKESGPTLVKPTQTLTLTCTLSGFSLSTSGVSVGWIRQPPGKALEWLASINWNDDKCYSPSLKSRLTITKDTPKNQV
VLAMSNMDPADTATYSCALDMPPHDSGPQSFDASDVWGPGTMVTVSSGGGGSGGGGSGGGGSGGGGSSYELMQLPSVSVS
PGQTASITCSGDNLGDKYACWYQQKPGRSPVLVIYGDNKRPSGIPERFSGSNSGNTATLTISGTQAMDEADYYCQAWDTS
TAVFGTGTKLTVL

DNA sequence of clone 15.150.11 scFv against loop 6 fragment of human CCR5 [SEQ ID NO: 18]:

CAGGTGCAGCTGCAGGAGTCGGGCCCAGGACTGGTGAAGCCTTCGGAGACCCTGTCCCTCACTTGCACTGTCTCTGGTGG
CTCCATCGGTCATGACTACTGGAGCTGGATACGGCAGCCCCCAGGGGAGGGACTGGAGTGGATTGGTTTCATCTTCTTCG
ATGGGAGCACCAACTACAACCCCTCCCTCAACGGTCGAGtCACCATCTCACTCGACACGTCGAAGAATCAGCTCTCCCTG
AGGCTGACCTCTGTGACCGCTGCGGACACGGCCGTGTATTTCTGTGCGAGACTAAAGGGGGCGTGGTTATTGTCTGAACC
CCCTTACTTCAGCTCCGACGGCATGGACGTCTGGGGCCAAGGGACCACGGTCACCGTCCCCTCAGGCGGTGGTGGATCAG
GCGGCGGAGGATCTGGCGGAGGTGGCAGCGGTGGTGGAGGCAGTAATTTTATGCTGACTCAGCCCCCCTCAGCGTCTGGG
ACCCCCGGGCAGAGGGTCAGCATCTCTTGTTCTGGGAGCAGCTCCGACATCGGAAGTAATACTGTAAACTGGTACCAGCA
ACTCCCAGGAACGGCCCCCAAACTCCTCATCTATAGTAATAATCAGCGGCCCTCAGGGGTCCCTGACCGATTCTCTGGCT
TCAAGTCTGGCACCTCAGCCTCCCTGGTCATCAGTGGCCTCCAGTCTGAGGATGAGGCTGATTATTATTGTGCAGCATGG
GATGAGAGCCTGAATGGTGTGGTGTTCGGCGGAGGACCAAGG

Amino acid sequence of clone 15.150.11 scFv against loop 6 fragment of human CCR5 [SEQ ID NO: 19]:

QVQLQESGPGLVKPSETLSLTCTVSGGSIGHDYWSWIRQPPGEGLEWIGFIFFDGSTNYNPSLNGRVTISLDTSKNQLSL
RLTSVTAADTAVYFCARLKGAWLLSEPPYFSSDGMDVWGQGTTVTVPSGGGGSGGGGSGGGGSGGGGSNFMLTQPPSASG
TPGQRVSISCSGSSSDIGSNTVNWYQQLPGTAPKLLIYSNNQRPSGVPDRFSGFKSGTSASLVISGLQSEDEADYYCAAW
DESLNGVVFGGGPR

FIGURE 5 (cont.)

DNA sequence of clone 15.150.12 scFv against loop 6 fragment of human CCR5 [SEQ ID NO: 20]:

CAGGTGCAGCTACAGCAGTGGGGCGCAGGACTGTTGAAGTCTTGGGGAACCCTGTCCCTCACCTGCGCTGTCTCTGGTGC
GTCGTTTAGTGGTtATTATTGGAGCTGGATCCGCCAGCCCCCAGGgAAGGGGCTGGAGTGGATTGGGGAGATCAATCATC
GTGGAAGCACTACCTACAACCCGTCCCTCGACGGTCGAGTCACCATATCATTAGACACATCTACCAACCAGATCTCCCTT
AAACTGACCTCTATGACCGCCGCGGACACGGCCGTGTATTACTGTGCGAGGACAGTGGCTGGTACTAGTGACTACTGGGG
CCAGGGAACCCTGGTCACCGTTTCCTCAGGGAGTGCATCCGCCCCAACGGGCGGTGGTGGATCAGGCGGCGGAGGATCTG
GCGGAGGTGGCAGCGGTGGTGGAGGCAGTAAAACGACACTCACGCAGTCTCCAGCATTCATGTCAGCGACTCCAGGAGAC
AAAGTCAGCATCTCCTGCAAAGCCAGCCGAGACGTTGATGATGATGTGAACTGGTACCAACAGAGACCAGGAGAAGCTCc
TATTTTcATTATTGAAGATGCTACTACTCTCGTTCcTGGAATCTCACCTCGATTCAGTGGCAGCGGGTATGGAACCGATT
TTACCCTCACAATTAATAACATCGATTCTGAGGATGCTGCATATTATTTCTGTCTACAACATGATAATTTCCCGCTCACC
TTCGGCGGAGGGACCAAGGTGGAGATCAAA

Amino acid sequence of clone 15.150.12 scFv against loop 6 fragment of human CCR5 [SEQ ID NO: 21]:

QVQLQQWGAGLLKSWGTLSLTCAVSGASFSGYYWSWIRQPPGKGLEWIGEINHRGSTTYNPSLDGRVTISLDTSTNQISL
KLTSMTAADTAVYYCARTVAGTSDYWGQGTLVTVSSGSASAPTGGGGSGGGGSGGGGSGGGGSKTTLTQSPAFMSATPGD
KVSISCKASRDVDDDVNWYQQRPGEAPIFIIEDATTLVPGISPRFSGSGYGTDFTLTINNIDSEDAAYYFCLQHDNFPLT
FGGGTKVEIK

DNA sequence of clone 15.150.24 scFv against loop 6 fragment of human CCR5 [SEQ ID NO: 22]:

CAGGTCACCTTGAAGGAGTCTGGTCCTACGCTGGTGAAACCCACACAGACCCTCACGCTGACCTGCACCTTCTCTGGGTT
CTCACTCAGAACTACTGGAGAGGGTGTGGGCTGGGTCCGTCAGCCCCCAGGAAAGGCCCTGGAATGGCTTGCACTCATTT
ATTGGGATGATGATAAGCGCTACAGCCCATCTCTGAAGAGCAGGCTCACCATCACCAAGGACACCTCCAAAAAGCAGGTG
GTCCTTACAATGACCAACGTGGACCCAGCGGACACAGCCACCTATTACTGTACACACGAGCAATACTATTATGATACTAG
TGGTCAGCCATACTACTTTGACTTCTGGGGCCAGGGCACCCTGGTCACCGTCTCCTCAGGCGGTGGTGGATCAGGCGGCG
GAGGATCTGGCGGAGGTGGCAGCGGTGGTGGAGGCAGTAACATCCAGGTGACCCAGTCTCCATCCTCCCTGTCTGCATCT
GTAGGAGACAGAGTCACCATGACTTGCCGGGCGAGTCAGGACATTAGGAAGAATTTAAATTGGTATCAGCAAAAACCAGG
GAAAGCCCCTAAGGTCCTGATCTACGATGCATCCGATTTGGAAACAGGGATCCCATCAAGGTTCAGTGGAAGTGGATCTG
GGACAGATTTTATCCTCACCATCAGCAGCCTGCAGCCTGAAGATATTGCAACATACTACTGTCAACAGTCTGATTATTTA
CCGCTCACTTTCGGCGGAGGGACCAAAGTGGATATCAAA

Amino acid sequence of clone 15.150.24 scFv against loop 6 fragment of human CCR5 [SEQ ID NO: 23]:

QVTLKESGPTLVKPTQTLTLTCTFSGFSLRTTGEGVGWVRQPPGKALEWLALIYWDDDKRYSPSLKSRLTITKDTSKKQV
VLTMTNVDPADTATYYCTHEQYYYDTSGQPYYFDFWGQGTLVTVSSGGGGSGGGGSGGGGSGGGGSNIQVTQSPSSLSAS
VGDRVTMTCRASQDIRKNLNWYQQKPGKAPKVLIYDASDLETGIPSRFSGSGSGTDFILTISSLQPEDIATYYCQQSDYL
PLTFGGGTKVDIK

FIGURE 6

DNA sequence of a variant of clone 15.186.35 scFv against N-terminus fragment of human CCR5 [SEQ ID NO: 24]:

CAGGTCACCTTGAAGGAGTCTGGTCCTACGTTGGTGAAACCCACACAGACCCTCACGCTGACCTGCACCTTGTCTGGGTT
CTCACTCAGCACTAGTGGAGTGAGTGTGGGCTGGATCCGTCAGCCCCAGGAAAGGCCCTTGAGTGGCTTGCAAGCATAA
ATTGGAATGATGATAAGTGCTACAGCCCATCTCTGAAAAGCAGGCTCACCATCACCAAGgACACCCCCaAAAACCAGGTG
GTCCTTGCAATGAGCAACATGGACCCTGCGGACACAGCCACATATTCCTGTGCACTCGATATGCCCCCCCATGATAGTGG
CCCGCAATCTTTTGATGCTTCTGATGTCTGGGGCCCAGGGACAATGGTCACCGTCTCTTCAGGCGGTGGTGGATCAGGCG
GCGGAGGATCTGGCGGAGGTGGCAGCGGTGGTGGAGGCAGTTCCTATGAGCTGATGCAGCTACCCTCAGTGTCCGTGTCC
CCAGGACAGACAGCCAGCATCACCTGCTCTGGAGATAATTTGGGGGATAAATATGCCTGCTGGTATCAACAGAAGCCAGG
CCGGTCCCCTGTGCTGGTCATTTATGGAGATAACAAGCGGCCCTCAGGGATCCCTGAGCGATTCTCTGGCTCCAACTCTG
GGAACACAGCCACTCTGACCATCAGCGGGACCCAGGCTATGGATGAGGCTGACTATTACTGTCAGGCGTGGGACACCAGC
ACTGCTGTCTTCGGAACTGGGACCAAGCTCACCGTCCTA

Amino acid sequence of a variant of clone 15.186.35 scFv against N-terminus fragment of human CCR5 [SEQ ID NO: 25]:

QVTLKESGPTLVKPTQTLTLTCTLSGFSLSTSGVSVGWIRQPPGKALEWLASINWNDDKCYSPSLKSRLTITKDTPKNQV
VLAMSNMDPADTATYSCALDMPPHDSGPQSFDASDVWGPGTMVTVSSGGGGSGGGGSGGGGSGGGGSSYELMQLPSVSVS
PGQTASITCSGDNLGDKYACWYQQKPGRSPVLVIYGDNKRPSGIPERFSGSNSGNTATLTISGTQAMDEADYYCQAWDTS
TAVFGTGTKLTVL

DNA sequence of a variant of clone 15.150.11 scFv against loop 6 fragment of human CCR5 [SEQ ID NO: 26]:

CAGGTGCAGCTGCAGGAGTCGGGCCCAGGACTGGTGAAGCCTTCGGAGACCCTGTCCCTCACTTGCACTGTCTCTGGTGG
CTCCATCGGTCATGACTACTGGAGCTGGATACGGCAGCCCCAGGGGAGGGACTGGAGTGGATTGGTTTCATCTTCTTCG
ATGGGAGCACCAACTACAACCCCTCCCTCAACGGTCGAGtCACCATCTCACTCGACACGTCGAAGAATCAGCTCTCCCTG
AGGCTGACCTCTGTGACCGCTGCGGACACGGCCGTGTATTTCTGTGCGAGACTAAAGGGGGCGTGGTTATTGTCTGAACC
CCCTTACTTCAGCTCCGACGGCATGGACGTCTGGGGCCAAGGGACCACGGTCACCGTCTCCTCAGGCGGTGGTGGATCAG
GCGGCGGAGGATCTGGCGGAGGTGGCAGCGGTGGTGGAGGCAGTAATTTTATGCTGACTCAGCCCCCCTCAGCGTCTGGG
ACCCCCGGGCAGAGGGTCAGCATCTCTTGTTCTGGGAGCAGCTCCGACATCGGAAGTAATACTGTAAACTGGTACCAGCA
ACTCCCAGGAACGGCCCCCAAACTCCTCATCTATAGTAATAATCAGCGGCCCTCAGGGGTCCCTGACCGATTCTCTGGCT
TCAAGTCTGGCACCTCAGCCTCCCTGGTCATCAGTGGCCTCCAGTCTGAGGATGAGGCTGATTATTATTGTGCAGCATGG
GATGAGAGCCTGAATGGTGTGGTGTTCGGCGGAGGAACCAAGGTGACCGTCCTA

Amino acid sequence of a variant of clone 15.150.11 scFv against loop 6 fragment of human CCR5 [SEQ ID NO: 27]:

QVQLQESGPGLVKPSETLSLTCTVSGGSIGHDYWSWIRQPPGEGLEWIGFIFFDGSTNYNPSLNGRVTISLDTSKNQLSL
RLTSVTAADTAVYFCARLKGAWLLSEPPYFSSDGMDVWGQGTTVTVSSGGGGSGGGGSGGGGSGGGGSNFMLTQPPSASG
TPGQRVSISCSGSSSDIGSNTVNWYQQLPGTAPKLLIYSNNQRPSGVPDRFSGFKSGTSASLVISGLQSEDEADYYCAAW
DESLNGVVFGGGTKVTVL

FIGURE 6 (cont.)

DNA sequence of a variant of clone 15.150.12 scFv against loop 6 fragment of human CCR5 [SEQ ID NO: 28]:

CAGGTGCAGCTACAGCAGTGGGGCGCAGGACTGTTGAAGTCTTGGGGAACCCTGTCCCTCACCTGCGCTGTCTCTGGTGC
GTCGTTTAGTGGTtATTATTGGAGCTGGATCCGCCAGCCCCCAGGgAAGGGGCTGGAGTGGATTGGGGAGATCAATCATC
GTGGAAGCACTACCTACAACCCGTCCCTCGACGGTCGAGTCACCATATCATTAGACACATCTACCAACCAGATCTCCCTT
AAACTGACCTCTATGACCGCCGCGGACACGGCCGTGTATTACTGTGCGAGGACAGTGGCTGGTACTAGTGACTACTGGGG
CCAGGGAACCCTGGTCACCGTTTCCTCAGGGAGTGCATCCGCCCCAACGGGCGGTGGTGGATCAGGCGGCGGAGGATCTG
GCGGAGGTGGCAGCGGTGGTGGAGGCAGTGAAACGACACTCACGCAGTCTCCAGCATTCATGTCAGCGACTCCAGGAGAC
AAAGTCAGCATCTCCTGCAAAGCCAGCCGAGACGTTGATGATGATGTGAACTGGTACCAACAGAGACCAGGAGAAGCTCc
TATTTTcATTATTGAAGATGCTACTACTCTCGTTCcTGGAATCTCACCTCGATTCAGTGGCAGCGGGTATGGAACCGATT
TTACCCTCACAATTAATAACATCGATTCTGAGGATGCTGCATATTATTTCTGTCTACAACATGATAATTTCCCGCTCACC
TTCGGCGGAGGGACCAAGGTGGAGATCAAA

Amino acid sequence of a variant of clone 15.150.12 scFv against loop 6 fragment of human CCR5 [SEQ ID NO: 29]:

QVQLQQWGAGLLKSWGTLSLTCAVSGASFSGYYWSWIRQPPGKGLEWIGEINHRGSTTYNPSLDGRVTISLDTSTNQISL
KLTSMTAADTAVYYCARTVAGTSDYWGQGTLVTVSSGSASAPTGGGGSGGGGSGGGGSGGGGSETTLTQSPAFMSATPGD
KVSISCKASRDVDDDVNWYQQRPGEAPIFIIEDATTLVPGISPRFSGSGYGTDFTLTINNIDSEDAAYYFCLQHDNFPLT
FGGGTKVEIK

DNA sequence of a variant of clone 15.150.24 scFv against loop 6 fragment of human CCR5 [SEQ ID NO: 30]:

CAGGTCACCTTGAAGGAGTCTGGTCCTACGCTGGTGAAACCCACACAGACCCTCACGCTGACCTGCACCTTCTCTGGGTT
CTCACTCAGAACTACTGGAGAGGGTGTGGGCTGGGTCCGTCAGCCCCCAGGAAAGGCCCTGGAATGGCTTGCACTCATTT
ATTGGGATGATGATAAGCGCTACAGCCCATCTCTGAAGAGCAGGCTCACCATCACCAAGGACACCTCCAAAAAGCAGGTG
GTCCTTACAATGACCAACGTGGACCCAGCGGACACAGCCACCTATTACTGTACACACGAGCAATACTATTATGATACTAG
TGGTCAGCCATACTACTTTGACTTCTGGGGCCAGGGCACCCTGGTCACCGTCTCCTCAGGCGGTGGTGGATCAGGCGGCG
GAGGATCTGGCGGAGGTGGCAGCGGTGGTGGAGGCAGTAACATCCAGGTGACCCAGTCTCCATCCTCCCTGTCTGCATCT
GTAGGAGACAGAGTCACCATGACTTGCCGGGCGAGTCAGGACATTAGGAAGAATTTAAATTGGTATCAGCAAAAACCAGG
GAAAGCCCCTAAGGTCCTGATCTACGATGCATCCGATTTGGAAACAGGGATCCCATCAAGGTTCAGTGGAAGTGGATCTG
GGACAGATTTTATCCTCACCATCAGCAGCCTGCAGCCTGAAGATATTGCAACATACTACTGTCAACAGTCTGATTATTTA
CCGCTCACTTTCGGCGGAGGGACCAAAGTGGATATCAAA

Amino acid sequence of a variant of clone 15.150.24 scFv against loop 6 fragment of human CCR5 [SEQ ID NO: 31]:

QVTLKESGPTLVKPTQTLTLTCTFSGFSLRTTGEGVGWVRQPPGKALEWLALIYWDDDKRYSPSLKSRLTITKDTSKKQV
VLTMTNVDPADTATYYCTHEQYYYDTSGQPYYFDFWGQGTLVTVSSGGGGSGGGGSGGGGSGGGGSNIQVTQSPSSLSAS
VGDRVTMTCRASQDIRKNLNWYQQKPGKAPKVLIYDASDLETGIPSRFSGSGSGTDFILTISSLQPEDIATYYCQQSDYL
PLTFGGGTKVDIK

FIGURE 7

Amino acid sequence alignment of variants of selected scFv antibodies against loop 6 of human CCR5

$V_H$ region:

```
                                             CDR1                     CDR2                                                      CDR3
15.150.11 QVQLQESGPGLVKPSETLSLTCTVSGGSI--GHDYWSWIRQPPGEGLEWIGFIFFDGSTNYNPSLNGRVTISLDTSKNQLSLRLTSVTAADTAVYFCARLKGAWLLSEPPYFSSDGMDVWGQGTTVTVSS
15.150.12 QVQLQQWGAGLLKSWGTLSLTCAVSGASF--SGYYWSWIRQPPGKGLEWIGEINHRGSTTYNPSLDGRVTISLDTSTNQISLKLTSMTAADTAVYYCART------------VAGTSDYWGQGTLVTVSS
15.150.24 QVTLKESGPTLVKPTQTLTLTCTFSGFSLRTTGEGVGWVRQPPGKALEWLALIYWDDDKRYSPSLKSRLTITKDTSKKQVVLTMTNVDPADTATYYCTHEQYYYDTSGQPYY----FDFWGQGTLVTVSS
```

$V_L$ region:

```
                                          CDR1                  CDR2                                          CDR3
15.150.11 NFMLTQPPS-ASGTPGQRVSISCSGSSS-DIGSNTVNWYQQLPGTAPKLLIYSNNQRPSGVPDRFSGFKSGTSASLVISGLQSEDEADYYCAAWDESLNGVVFGGGTKVTVL
15.150.12 ETTLTQSPAFMSATPGDKVSISCKASR--DVDDD-VNWYQQRPGEAPIFIIEDATTLVPGISPRFSGSGYGTDFTLTINNIDSEDAAYYFCLQHDNF--PLTFGGGTKVEIK
15.150.24 NIQVTQSPSSLSASVGDRVTMTCRASQ--DI-RKNLNWYQQKPGKAPKVLIYDASDLETGIPSRFSGSGSGTDFILTISSLQPEDIATYYCQQSD-YL-PLTFGGGTKVDIK
```

FIGURE 8

Amino acid sequences of variable regions of clone 15.186.35 scFv against N-terminus fragment of human CCR5

V$_H$ region [SEQ ID NO: 34]:
QVTLKESGPTLVKPTQTLTLTCTLSGFSLSTSGVSVGWIRQPPGKALEWLASINWNDDKCYSPSLKSRLTITKDTPKNQV
VLAMSNMDPADTATYSCALDMPPHDSGPQSFDASDVWGPGTMVTVSS V$_L$ region [SEQ ID NO: 35]:
SYELMQLPSVSVSPGQTASITCSGDNLGDKYACWYQQKPGRSPVLVIYGDNKRPSGIPERFSGSNSGNTATLTISGTQAM
DEADYYCQAWDTSTAVFGTGTKLTVL

Partial amino acid sequences of variable regions of clone 15.150.11 scFv against loop 6 fragment of human CCR5

V$_H$ region [SEQ ID NO: 36]:
QVQLQESGPGLVKPSETLSLTCTVSGGSIGHDYWSWIRQPPGEGLEWIGFIFFDGSTNYNPSLNGRVTISLDTSKNQLSL
RLTSVTAADTAVYFCARLKGAWLLSEPPYFSSDGMDVWGQGTTVTV V$_L$ region [SEQ ID NO: 37]:
NFMLTQPPSAXGTPGQRVSISCSGSSSDIGSNTVNWYQQLPGTAPKLLIYSNNQRPSGVPDRFSGFKSGTSASLVISGLQ
SEDEADYYCAAWDESLNGVVFGGG

Partial amino acid sequences of variable regions of clone 15.150.12 scFv against loop 6 fragment of human CCR5

V$_H$ region [SEQ ID NO: 38]:
QVQLQQWGAGLLKSWGTLSLTCAVSGASFSGYYWSWIRQPPGKGLEWIGEINHRGSTTYNPSLDGRVTISLDTSTNQISL
KLTSMTAADTAVYYCARTVAGTSDYWGQGTLVTVSS V$_L$ region [SEQ ID NO: 39]:
TTLTQSPAFMSATPGDKVSISCKASRDVDDDVNWYQQRPGEAPIFIIEDATTLVPGISPRFSGSGYGTDFTLTINNIDS
EDAAYYFCLQHDNFPLTFGGGTKVEIK

Amino acid sequences of variable regions of clone 15.150.24 scFv against loop 6 fragment of human CCR5

V$_H$ region [SEQ ID NO: 40]:
QVTLKESGPTLVKPTQTLTLTCTFSGFSLRTTGEGVGWVRQPPGKALEWLALIYWDDDKRYSPSLKSRLTITKDTSKKQV
VLTMTNVDPADTATYYCTHEQYYYDTSGQPYYFDFWGQGTLVTVSS V$_L$ region [SEQ ID NO: 41]:
NIQVTQSPSSLSASVGDRVTMTCRASQDIRKNLNWYQQKPGKAPKVLIYDASDLETGIPSRFSGSGSGTDFILTISSLQP
EDIATYYCQQSDYLPLTFGGGTKVDIK

DNA Sequence of scFv Ab124 against CXCR4 Loop 6 [SEQ ID NO: 59]:

CAGGTGCAGCTGCAGGAGTCCGGCCCAGGACTGGTGAAGCCTTCGGAGACCCTGTCCCTCACCTGCACTGTCTCTGGTGG
CTCCATCAGCAGTAGTAGTTACTACTGGGGCTGGATCCGCCAGCCCCCAgGGAAGGGGCTGGAGTGGATTGGGAGTATCT
ATTATAGTGGGAGCACCTACTACAACCCGTCCCTCAAGAGTCGAGTCACCATATCCGTAGACACGTCCAAGAACCAGTTC
TCCCTGAAGCTGAGCTCTGTGACCGCCGCAGACACGGCTGTGTATTACTGTGCGAGACATATTCTTACGAAAGCAGCTGG
CTACTGGTACTTCGATCTCTGGGGCCGTGGCACCCTGGTCACCGTCTCCTCTGGCGGTGGTGGATCAGGCGGCGGAGGAT
CTGGCGGAGGTGGCAGCGGTGGTGGAGGCAGTCAGTCTGTTCTGATTCAGCCTCGCTCAGTGTCCGGGTCTCCTGGACAG
TCAGTCACCATCTCCTGCACTGGAACCAGCAGTGATGTTGGTGGTTATAACTATGTCTCCTGGTACCAACAGCACCCAGG
CAAAGCCCCCAAACTCATGATTTATGATGTCAGTAAGCGGCCCTCAGGGGTCCcTGATCgCTTCTCTGGCTCCAAGTCTG
GCAACACGGCCTCCCTGACcATcTCTGGGCTCCAGGCTGAGGATGAGGCTGATTATTACTGCTGCTCATATGCAGGCAGC
TACAGGGATTATGTCTTCGGAACTGGGACCAAGCTGACCGTCCTA

Amino acid sequence of Ab124 V$_H$ [SEQ ID NO: 60]:

QVQLQESGPGLVKPSETLSLTCTVSGGSISSSSYYWGWIRQPPGKGLEWIGSIYYSGSTYYNPSLKSRVTISVD
TSKNQFSLKLSSVTAADTAVYYCARHILTKAAGYWYFDLWGRGTLVTVSS

Amino acid sequence of Ab124 V$_L$ [SEQ ID NO: 61]:

QSVLIQPRSVSGSPGQSVTISCTGTSSDVGGYNYVSWYQQHPGKAPKLMIYDVSKRPSGVPDRFSGSKSGNTAS
LTISGLQAEDEADYYCCSYAGSYRDYVFGTGTKLTVL

B. Ab125

DNA Sequence of scFv Ab125 against CXCR4 Loop 6 [SEQ ID NO: 62]:

CAGGTGCAGCTACAGCAGTGGGGCGCAGGACTGTTGAAGCCTTCGGAGACCCTGTCCCTCACCTGCGCTGTCTATGGTGG
GTCCTTCAGTGGTTACTACTGGAGCTGGATCCGCCAGCCCCCAGGGAAGGGGCTGGAGTGGATTGGGGAAATCAATCATA
GTGGAAGCACCAACTACAACCCGTCCCTCAAGAGTCGAGTCACCATATCAGTAGACACGTCCAAAAACCAATTCTCCCTG
AAGCTGAGCTCTGTGACCGCCGCGGACACGGCTGTGTATTACTGTGCGAGAGGCCGACGTAGTATAGCAGCTCGTCCGTT
TTCTTTTGATATCTGGGGCCAAGGGACAATGGTCACCGTCTCTTCAGGCGGTGGTGGATCAGGCGGCGGAGGATCTGGCGGAGGTGGC
AGCGGTGGTGGAGGCAGTCAGCCTGTGCTGACTCAATCACCCTCAGCGTCTGGGACCCCCGGCCAGAGGGTCACCATCTC
TTGTTCTGGAAgCAGCTCCaACATCGGAATTAATCCTGTAAACTGGTACCAGCAGCTCCcAGGAGCGGCTCCCAAACTcC
TCATCTACACTACTAATCAGCGGCCCTCAGGGGTCCCTGACCGATTCTCTGCCTCCAAGTCTGGCACCTCGGCCTCCCCG
GCCATCAGTGGACTCCAGTCTGCGGATGAGGCTGATTATTACTGTGCAGCGTGGGATGACAGGCTGAATGGTGTGGTTTT
CGGCGGTGGGACCAAGCTCACCGTCCTC

Amino acid sequence of Ab125 V$_H$ [SEQ ID NO: 63]:

QVQLQQWGAGLLKPSETLSLTCAVYGGSFSGYYWSWIRQPPGKGLEWIGEINHSGSTNYNPSLKSRVTISVDTS
KNQFSLKLSSVTAADTAVYYCARGRRSIAARPFSFDIWGQGTMVTVSS

Amino acid sequence of Ab125 V$_L$ [SEQ ID NO: 64]:

QPVLTQSPSASGTPGQRVTISCSGSSSNIGINPVNWYQQLPGAAPKLLIYTTNQRPSGVPDRFSASKSGTSASP
AISGLQSADEADYYCAAWDDRLNGVVFGGGTKLTVL

HUMAN MONOCLONAL ANTIBODIES AGAINST HUMAN CXCR4

CROSS REFERENCE TO RELATED APPLICATIONS

This application is a continuation-in-part of Application entitled "METHODS FOR GENERATING MONOCLONAL ANTIBODY AGAINST FUSION PROTEIN CONTAINING PEPTIDE GRAGMENT DERIVED FROM MEMBRANE PROTEIN", application Ser. No. 10/133,978, now abandoned, filed Apr. 25, 2002, which is a continuation-in-part of Application entitled "HUMAN MONOCLONAL ANTIBODY AGAINST CORECEPTORS FOR HUMAN IMMUNODEFICIENCY VIRUS", application Ser. No. 10/072,301, now U.S. Pat. No. 7,005,503, filed on Feb. 8, 2002, and Application entitled "HIGH THROUGHPUT GENERATION HUMAN MONOCLONAL ANTIBODY AGAINST PEPTIDE FRAGMENTS DERIVED FROM MEMBRANE PROTEINS", application Ser. No. 10/071,866, now abandoned, filed Feb. 8, 2002. These applications are incorporated herein by reference in their entirety.

BACKGROUND OF THE INVENTION

1. Field of the Invention

This invention relates to methods for generating monoclonal antibody against cell membrane proteins, and, more particularly, to methods for generating human monoclonal antibodies against cell surface coreceptors for human immunodeficiency virus (HIV) and using these antibodies for diagnostic or therapeutic purposes.

2. Description of Related Art

HIV infection has been implicated as the primary cause of the slowly degenerate disease of the immune system termed acquired immune deficiency syndrome (AIDS). Barre-Sinoussi et al. (1983) Science 220:868–870; and Gallo et al. (1984) Science 224:500–503. Infection of the CD4+ subclass of T-lymphocytes with the HIV-1 virus leads to depletion of this essential lymphocyte subclass which inevitably leads to opportunistic infections, neurological disease, neoplastic growth and eventually death. HIV-1 infection and HIV-1 associated diseases represent a major health problem and considerable attention is currently being directed towards the successful design of effective therapeutics.

HIV-1 is a member of the lentivirus family of retroviruses. Teich et al. (1984) In RNA Tumor Viruses ed. R. Weiss, N. Teich, H. Varmus, J. Coffin CSH Press, pp. 949–56. The life cycle of HIV-1 is characterized by a period of proviral latency followed by active replication of the virus. The primary cellular target for the infectious HIV-1 virus is the CD4 subset of human T-lymphocytes. Targeting of the virus to the CD4 subset of cells is due to the fact that the CD4 cell surface protein acts as the cellular receptor for the HIV-1 virus. Dalgleish et al. (1984) Nature 312:763–67; Klatzmann (1984) Nature 312:767–68; and Maddon et al. (1986) Cell 47:333–48.

After binding to the cell surface, the HIV-1 virion becomes internalized, and once inside the cell, the viral life cycle begins by conversion of the RNA genome into linear DNA molecules. This process is dependent on the action of the virally encoded reverse transcriptase. Following replication of the viral genome, the linear DNA molecule integrates into the host genome through the action of the viral integrase protein, thus establishing the proviral form of HIV-1.

It was later discovered that other than CD4, HIV-1 utilizes several cell membrane proteins as its coreceptor to falitate viral entry into the host cell. Alkhatib et al. (1996) Science 272: 1955–1958; and Deng et al. (1996) Nature 388:296–300. Examples of chemokine receptors include CXCR4, CCR5, CCR1, CCR2b, CCR3, CCR4, CCR8, CXCR1, CXCR2, CXCR3, and $CX_3CR1$. Examples of chemokine receptor-like orphan proteins include STRL33/BONZO and GPR15/BOB.

CXCR4 (also known as "fusin") is a receptor for chemokines such as SDF-1α and SDF-1β. CCR5 is a receptor for several CC chemokines such as MIP-1α (also named GOS19, LD78, pAT464 gene product, TY5 (murine) and SISα (murine)), MIP-1β (also named Act-2, G-26, pAT744 gene product, H-400 (murine) and hSISγ (murine)) and RANTES (regulated on activation, normal T cell expressed and secreted, or CCL5). Cocchi et al. (1995) Science 270: 1811–1815; and Mellado et al. (2001) Annu. Rev. Immunol. 19:397–421. The roles of these CC chemokine molecules in regulating T cell fate include possible indirect effects on antigen-presenting cells and direct effects on differentiating T cells. Luther & Cyster (2001) Nat. Immunol. 2:102–107.

Specific chemokine receptors such as CXCR4 and CCR5 receptors play important roles in mediating HIV entry and tropism for different target cells. See reviews by Berger (1997) AIDS 11, Suppl. a: S3–S16; and Dimitrov (1997) Cell 91: 721–730; and Burger et al. (1999) Annu. Rev. Immunol. 17:657–700. Macrophages-tropic (M-tropic) strains of HIV virus can replicate in primary $CD4^+$ T cells and macrophages and use the β-chemokine receptor CCR5 and less often, CCR3 receptor. T cell line-tropic (T-tropic) HIV strains can also replicate in primary $CD4^+$ T cells but can in addition infect established $CD4^+$ T cell lines in vitro via the α-chemokine receptor CXCR4. Many of the T-tropic strains can use CCR5 in addition to CXCR4. Chemokine receptor-like HIV coreceptor STRL33 is expressed in activated peripheral blood lymphocytes and T-cell lines and can function as an entry cofactor for Env proteins from M-tropic, T-tropic and dual tropic strains of HIV-1 and SIV. Other HIV coreceptors have also been identified by numerous in vitro assays, including chemokine receptors CCR2b, CCR3, CCR8 and CX3CR1 as well as several chemokine receptor-like orphan receptor proteins such as GPR15/BOB and STRL33/BONZO. Each or a set of these HIV coreceptors can mediate entry of different strains of HIV virus into the host cell.

The CC chemokine receptor CCR5 is a principal HIV-1 coreceptor that plays a dominant role in disease transmission and in the early course of infection. Berger et al. (1999) Annu. Rev. Immunol. 17:657–700. Molecular epidemiology studies clearly demonstrated that CCR5 plays critical roles in HIV-1 transmission and pathogenesis. Individuals lacking two copies of functional CCR5 alleles (Δ32 allele) are strongly protected against HIV-1 infection. Dean et al. (1996) Science 273:1856–1862. Individuals with one Δ32 and one normal CCR5 gene on average express lower levels of CCR5 on their T cells. Wu et al. (1997) J. Exp Med. 185:1681–1691. Heterozygosity for the Δ32 allele does not protect against HIV-1 infection but does confer an improved prognosis in the form of significantly increased AIDS-free and overall survival periods. Husman et al. (1997) Ann. Intern. Med. 127:882–890. Moreover, CCR5 heterozygotes are overrepresented among long-term nonprogressors, i.e., those individuals who do not progress to AIDS after 10 or more years of infection. Dean et al. (1996) Science 273: 1856–1862. Because it is an essential coreceptor for clinically relevant strains of HIV-1 and yet is apparently dispensable for human health, CCR5 provides an attractive target for new antiretroviral therapies. Liu et al. (1996) Cell 86:367–377; and Michael & Moore (1999) Nat. Med. 5:740–742.

Several approaches have been employed to target HIV coreceptors, involving proteins, peptides and small molecules. It has been found that some CCR5-targeting chemokines and chemokine analogs are capable of inhibiting HIV-1 replication in vitro. Berger et al. (1999) Annu. Rev. Immunol. 17:657–700. Of the CC chemokines that bind CCR5, RANTES possesses significantly greater breadth of antiviral activity than MIP-1α and MIP-1β, although all CC chemokines show interisolate variation in potency. Trkola et al. (1998) J. Viol. 72:396–404. The antiviral activity of the CC chemokines better correlates with their ability to downregulate rather than to bind CCR5 on CD4 T cells, and sustained down-regulation of CCR5 has been suggested to be a principal mechanism of action for the chemokine analog aminooxypentane (AOP)-RANTES. Mack et al. (1998) J. Exp. Med. 187:1215–1224. A small non-peptide molecule designated TAK-779 was found to be an antagonist against CCR5 presumably through binding to a hydrophobic pocket defined by the transmembrane helices 1, 2, 3 and 7. Baba et al. (1999) Proc. Natl. Acad. Sci. USA 96:5698–5703; Shiraishi et al. (2000) J. Med. Chem. 43:2049–2063; and Dragic et al. (2000) Proc. Natl. Acad. Sci. USA 97:5639–5644.

Phage display has been utilized to select for single chain antibody against CCR5 from a human antibody library by using CCR5-expressing CD4$^+$ lymphocytes as the target in the presence and absence of MIP-1α. Osbourn et al. (1998) Nature Biotech. 16:778–781. The selected phage particles were analyzed by phage ELISA for their ability to recognize CD4$^+$ lymphocytes, CCR5-transfected CHO cell line, non-transfected CHO cell line, and a BSA-conjugated peptide corresponding to the N-terminal 20 amino acid peptide of CCR5. Osbourn et al. found that none of the antibodies selected in the presence of MIP-1α blocked MIP-1α binding to CD4$^+$ lymphocytes. Among the antibodies selected in the absence of MIP-1α, around 20% inhibited MIP-1α binding to CD4$^+$ lymphocytes, as well as MIP-1α-mediated calcium signaling.

Mouse monoclonal antibodies have also been generated to target CCR5 by using the whole protein of CCR5 as the antigen. For example, Wu et al. immunized mice with the murine pre-B cell lymphoma cell line L1.2 expressing high levels of transfected CCR5, which generated a IgG1 monoclonal antibody, designated as mAb 2D7. Wu et al. (1997) J. Exp. Med. 186:1373–1381. The binding site of this monoclonal on CCR5 was mapped to the second extracellular loop of CCR5. MAb 2D7 was shown to be able block the binding and chemotaxis of the three natural chemokine ligands of CCR5, RANTES, macrophage inflammatory protein MIP-1α, and MIP-1β, to CCR5 transfectants. MAb 2D7 failed to stimulate an increase in intracellular calcium concentration in the CCR5 transfectants, but blocked calcium response elicited by RANTES, MIP-1α and MIP-1β chemotactic responses of activated T cells, but not of monocyte. In contrast, a group of mAbs that were also generated in the same process and failed to clock chemokine binding were all mapped to the N-terminal region of CCR5.

Using a similar strategy to Wu et al. (1997), Olson et al. isolated 6 anti-CCR5 murine monoclonal antibodies (MAbs) by intraperitoneally immunizing female BALB/c mice with murine L1.2 cells expressing CCR5. Olson et al. (1999) J. Virol. 73:4145–4155. Epitope mapping of these MAbs reveals that the epitopes of these antibodies reside in the N-terminus and/or second extracellular loop regions of CCR5. This structural information was correlated with the antibodies' abilities to inhibit (1) HIV-1 entry; (2) HIV-1 envelope glycoprotein-mediated membrane fusion; (3) gp120 binding to CCR5; and (4) CC-chemokine acitvity. Surprisingly, each of the antibodies displayed distinctly different activities in different stages of HIV-1 entry. In particular, one of these MAbs, PRO140, was shown to exert inhibitory effects on HIV-1 infection on primary peripheral blood mononuclear cells (PBMC). Trkola et al. (2001) J. Virol, 75:579–588.

SUMMARY OF THE INVENTION

The present invention provides innovative methods for generating antibodies against a wide variety of proteins targets, especially against membrane proteins. In particular, methods are provided for eliciting monoclonal antibody against a target membrane protein by using a fusion protein as an immunogen that contains a peptide fragment derived from the membrane protein. More particularly, efficient high through methods are provided for screening fully human antibody library against membrane proteins such as HIV coreceptors in yeast.

In one aspect of the invention, a method is provided for eliciting antibodies against a membrane protein in a non-human animal. The method comprises: immunizing a non-human animal with an antigen that is a fusion protein between a peptide fragment of a target membrane protein and a heterologous chaperon protein that stabilizes the peptide fragment.

The step of immunizing the animal may include injecting the antigen directly into the animal. For example, the antigen may be injected into a mouse to elicit polyclonal antibodies, or monoclonal antibodies by using a hybridoma technology. The animal may be a natural animal, a transgenic animal that has been genetically modified to produce human antibodies, such as XENOMOUSE® and HuMab Mouse, or a transchromosome (TC) mouse.

Optionally, the step of immunizing the animal may include transfecting the animal with an expression vector encoding the antigen. For example, DNA sequence encoding the antigen can be inserted into a mammalian expression vector or a viral vector (e.g., retroviral, adenoviral, and adeno-associated viral vectors) and the resulting expression vector can be injected into the animal where the expression of the antigen by the vector elicits immune responses to the antigen. Antibodies can then be isolated from the serum of the animal and used to target the membrane protein for therapeutic or diagnostic purposes.

In another aspect of the invention, a method is provided for selecting antibody against a membrane protein in vitro. The method comprises: contacting a library of antibodies with an antigen that is a fusion protein between a peptide fragment of a target membrane protein and a heterologous chaperon protein that stabilizes the peptide fragment; and selecting the antibodies that bind to the antigen.

According to the above-described methods, the chaperon protein may be any protein or a domain of a protein that is capable of stabilizing the fused peptide, for example, structurally stabilizing the conformation of the peptide under the condition of the immunization or screening process and/or preventing degradation of the peptide. Preferably, the chaperon protein may be a DNA binding domain (BD) or an activation domain (AD) of a transcription factor. More preferably, the chaperon protein may include Gal4 DNA binding domain, LexA binding domain, lambda cl DNA binding domain, cdc25 or Sos (guanine nucleotide exchange factor), T18 bacterial protein, T25 bacterial protein, the alpha and omega fragments of beta-lactamase, glutathion-S-transferase (GST) and thioredoxin.

The library of antibodies may be a library of antibodies mixed in solution, immobilized to a substrate in the form of an array, or displayed by mRNA, ribosome, phage, and cells such as yeast cells.

The antibodies in the library may be in the form of a single chain antibody, Fab antibody and fully assembled antibody.

In yet another aspect of the invention, a method is provided for screening a library of single chain antibodies (scFv) against a target peptide in yeast. In one embodiment, the method comprising:

expressing a library of scFv fusion proteins in yeast cells, each scFv fusion protein comprising either an activation domain or a DNA binding domain of a transcription activator and a scFv, the scFv comprising a $V_H$ of antibody whose sequence varies within the library, a $V_L$ of antibody whose sequence varies within the library independently of the $V_H$, and a linker peptide which links the $V_H$ and $V_L$;

expressing a target fusion protein in the yeast cells expressing the scFv fusion proteins, the target fusion protein comprising either the DNA binding domain or the activation domain of the transcription activator which is not comprised in the scFv fusion proteins, and a target peptide; and selecting those yeast cells in which a reporter gene is expressed, the expression of the reporter gene being activated by a reconstituted transcriptional activator formed by binding of the scFv fusion protein to the target fusion protein.

According to the embodiment, the diversity of the library scFv fusion proteins is preferably higher than $1\times10^4$, more preferably higher than $1\times10^6$, and most preferably higher than $1\times10^7$. Optionally, the diversity of the library scFv fusion proteins is between $1\times10^4$–$1\times10^{11}$, $1\times10^6$–$1\times10^{10}$, $1\times10^7$–$1\times10^{10}$, $1\times10^7$–$1\times10^9$, or $1\times10^8$–$1\times10^{10}$.

In yet another aspect of the invention, a method is provided for screening a library of antibodies against a target peptide in yeast. In one embodiment, the method comprising:

expressing a library of antibody fusion proteins in yeast cells, each antibody fusion protein comprising either an activation domain or a DNA binding domain of a transcription activator which is fused with either $V_H$ or $V_L$ of the antibody, wherein the sequences of $V_H$ and $V_L$ of the antibody vary independently within the library, and the $V_H$, $V_L$ and their fusions thereof are expressed as separate proteins and assemble in yeast to form the antibody fusion proteins;

expressing a target fusion protein in the yeast cells expressing the antibody fusion proteins, the target fusion protein comprising either the DNA binding domain or the activation domain of the transcription activator which is not comprised in the antibody fusion proteins, and a target peptide; and selecting those yeast cells in which a reporter gene is expressed, the expression of the reporter gene being activated by a reconstituted transcriptional activator formed by binding of the antibody fusion protein to the target fusion protein.

According to the embodiment, the diversity of the library antibody fusion proteins is preferably higher than $1\times10^4$, more preferably higher than $1\times106$, and most preferably higher than $1\times10^7$. Optionally, the diversity of the library antibody fusion proteins is between $1\times10^4$–$1\times10^{11}$, $1\times10^6$–$1\times10^{10}$, $1\times10^7$–$1\times10^{10}$, $1\times10^7$–$1\times10^9$, or $1\times10^8$–$1\times10^{10}$.

According to any of the above methods, the length of the target peptide is preferably 5–100 aa, more preferably 10–80 aa, and most preferably 20–60 aa.

According to any of the above methods, the target peptide or peptide fragment may be a fragment of a protein that includes an antigenic determinant or epitope, preferably a fragment of a membrane protein, more preferably an extracellular domain of a membrane protein, and most preferably an extracellular loop of a transmembrane protein.

Examples of the membrane protein include, but are not limited to, receptors for growth factors (e.g., vascular endothelial growth factor (VEGF), transforming growth factor (TGF), fibroblast growth factor (FF), platelet derived growth factor (PDGF), insulin-like growth factor), insulin receptor, MHC proteins (e.g. class I MHC and class II MHC protein), CD3 receptor, T cell receptors, cytokine receptors (e.g., interleukin (IL)-1, IL-2, IL-3, IL-4, IL-5, IL-6, IL-7, IL-8, IL-9, IL-10, IL-11, IL-12, IL-13, IL-14, IL-15 receptors), tyrosine-kinase-associated receptors such as Src, Yes, Fgr, Lck, Flt, Lyn, Hck, and Blk, and G-protein coupled receptors such as receptors for the hormone relaxin (LGR7 and LGR8) and chemokine receptor (e.g., CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CX3CR1, and XCR1), PSGR, beta1-adrenergic receptor, beta2-adrenergic receptor, parathyroid hormone (PTH) receptor, EDG1, G10d, opioid receptors, neutensin recetpors, neuropeptide Y (NPY) receptors, melatonin receptor, adrenocorticotrophin (ACTH) receptor, leukotriene receptors, 5-hydroxytryptamine (5-HT, or serotonin) receptors (including 5-TH1a, 5-TH1b, 5-TH1d, 5-TH1e, 5-TH1f, 5-TH2a, 5-TH2b, 5-TH2c, 5-TH3, 5-TH4, 5-TH5 receptors), FSH receptor, LH/hCG recetpor, TSH receptor, formyl-methionyl peptide (fMLP) receptors (FPR1 receptor, FPR2 receptor, FPR3 receptor), GABA receptors, endothelin (ET) receptors, sarafotoxin receptors, dopamin receptors (D1 receptor, D2 receptor, D3 receptor, D4 receptor, D5 receptor), cannabinoid receptor, CGRP1 receptor, CGRP2 receptor, amylin receptor, calcitonin receptor, C5a receptor, bradykinin receptors (B1, B2 and B3 receptors), bombesin Receptors (BB1, BB2 and BB3 receptors), angiotensin receptors (AT1 a, AT1 b and AT2 receptors), adrenaline and noradrenaline receptors (or adrenoceptors), acetylcholine Receptors, platelet activating factor (PAF) receptor, prostanoid receptors (DP, EP1, EP2, EP3, FP, IP and TP receptors), somatostanin receptors (SS1, SS2, SS3, SS4 receptors), tachykinin Recetpors (NK1, NK2 and NK3 receptors), thrombin receptor, vasoactive Intestinal polypeptide (VIP) receptor family (GRF, PACAP, secretin, VIP and helodermin-preferring receptors), stresscopin receptor, urocortin receptor, corticotropin releasing hormone receptors, LGR4, LGR5, LGR6, LGR7 and LGR8; and GPCR orphan receptors designated as GPR1–58 at GenBank.

The target peptide or peptide fragment may also be derived from a viral surface or core protein. Examples of these viral proteins include, but are not limited to, glycoproteins (or surface antigens, e.g., GP120 and GP41) and capsid proteins (or structural proteins, e.g., P24 protein); surface antigens or core proteins of hepatitis A, B, C, D or E virus (e.g. small hepatitis B surface antigen (SHBsAg) of hepatitis B virus and the core proteins of hepatitis C virus, NS3, NS4 and NS5 antigens); glycoprotein (G-protein) or the fusion protein (F-protein) of respiratory syncytial virus (RSV); surface and core proteins of herpes simplex virus HSV-1 and HSV-2 (e.g., glycoprotein D from HSV-2).

In one particular variation of the embodiment, the target peptide comprises an extracellular domain of human CCR5 selected from the group consisting of N-terminal domain, loop 2, loop 4, and loop 6 of human CCR5. Preferably, the extracellular domain of human CCR5 comprises a sequence selected from the group consisting of SEQ ID Nos: 2, 3, 8, and 9.

In another particular variation of the embodiment, the target peptide comprises an extracellular domain of human CXCR4 selected from the group consisting of N-terminal domain, loop 2, loop 4, and loop 6 of human CXCR4. Preferably, the extracellular domain of human CXCR4 comprises SEQ ID NO: 58.

Also according to the embodiment, the activation domain or the DNA binding domain of the transcription activator may optionally be fused to C-terminus of the scFv, or to the N-terminus of the scFv.

Also according to the embodiment, the activation domain or the DNA binding domain of the transcription activator may optionally be fused to C-terminus of the target peptide, or to the N-terminus of the target peptide.

According to the embodiment, the step of expressing the library of scFv fusion proteins in yeast cells may include transforming a library of scFv expression vectors into the yeast cells which contain the reporter gene.

Optionally, the step of expressing the target fusion proteins includes transforming a target expression vector into the yeast cells simultaneously or sequentially with the library of scFv expression vectors.

Also according to the embodiment, the steps of expressing the library of scFv fusion proteins and expressing the target fusion protein may optionally include causing mating between first and second populations of haploid yeast cells of opposite mating types.

The first population of haploid yeast cells comprises a library of scFv expression vectors for the library of scFv fusion proteins. The second population of haploid yeast cells comprises a target expression vector. Either the first or second population of haploid yeast cells comprises the reporter gene.

The haploid yeast cells of opposite mating types may preferably be α and a type strains of yeast. The mating between the first and second populations of haploid yeast cells of α and a type strains may be conducted in a rich nutritional culture medium.

It should be noted that the above-described target peptide fragment derived from a membrane protein may be screened against an antibody library in other organisms or in vitro. For example, the target peptide may be expressed as a fusion protein with another protein and screened against an antibody library co-expressed in mammalian cells. The target peptide may also be immobilized to a substrate as a single peptide or a fusion protein and selected against a library of antibodies displayed by mRNA, ribosome, phage or cells such as yeast cells. In addition, the target peptide may be introduced to a xenomouse, a HuMab mouse, or a transchromosomal mouse that contains a library of human antibody, and selected for monoclonal human antibodies with specific binding affinity to target peptide and/or the target membrane protein.

In yet another aspect of the invention, compositions that comprise at least one of the heavy chain and light chain variable region of an antibody are provided which recognize epitopes on the extracellular domains of human CCR5.

In one embodiment, the composition comprises an antibody that binds to loop 6 of human CCR5. In a variation, the antibody is capable of inhibiting HIV-1 infection of human cells.

It is noted the antibody may be a polyclonal or a monoclonal antibody, including but not limited to fully assembled antibody, single chain antibody, Fab fragment, and chimeric antibody.

Optionally, CDR2 of the heavy chain variable region of the antibody comprises amino acid sequence $GSTX_1YNPSL$ [SEQ ID NO: 32], wherein $X_1$ is asparagine (N) or threonine (T).

Optionally, CDR2 of the light chain variable region of the antibody comprises amino acid sequence $DAX_2X_3L$ [SEQ ID NO: 33], wherein $X_2$ is threonine (T) or serine (S), and $X_3$ is threonine (T) or aspartic acid (D).

Optionally, CDR2 of the heavy chain variable region of the antibody comprises amino acid sequence $GSTX_1YNPSL$ [SEQ ID NO: 32]; and CDR2 of the light chain variable region of the antibody comprises amino acid sequence $DAX_2X_3L$ [SEQ ID NO: 33], wherein $X_1$ is asparagine (N) or threonine (T), $X_2$ is threonine (T) or serine (S), and $X_3$ is threonine (T) or aspartic acid (D).

Optionally, CDR3 of the heavy chain variable region of the monoclonal antibody comprises 5, 6, 7, 8, 9 or more consecutive amino acids of a sequence elected from the group consisting of

| | |
|---|---|
| RLKGAWLLSEPPYFSSDGMDV, | [SEQ ID NO: 43] |
| RTVAGTSDY, and | [SEQ ID NO: 44] |
| HEQYYYDTSGQPYYFDF. | [SEQ ID NO: 45] |

Optionally, CDR3 of the light chain variable region of the monoclonal antibody comprises 5, 6, 7, 8, 9 or more consecutive amino acids of a sequence elected from the group consisting of

| | |
|---|---|
| AAWDESLNGVV, | [SEQ ID NO: 46] |
| LQHDNFPLT, and | [SEQ ID NO: 47] |
| QQSDYLPLT. | [SEQ ID NO: 48] |

Optionally, CDR3 of the heavy chain variable region of the monoclonal antibody comprises an amino acid sequence selected from the group consisting of SEQ ID Nos: 43–45; and CDR3 of the light chain variable region of the monoclonal antibody comprises an amino acid sequence selected from the group consisting of SEQ ID Nos: 46–48.

It is noted that the above-described different CDR regions may all be included in the antibody independent of each other, or in combination with one or more of each other.

Optionally, CDR3 of the heavy chain variable region of the antibody comprises an amino acid sequence selected from the group consisting of SEQ ID Nos: 43–45; and CDR3 of the light chain variable region of the antibody comprises an amino acid sequence selected from the group consisting of SEQ ID Nos: 46–48.

Optionally, the heavy chain variable region of the antibody comprises an amino acid sequence selected from SEQ ID Nos: 36, 38, and 40.

Optionally, the light chain variable region of the antibody comprises an amino acid sequence selected from SEQ ID Nos: 37, 39, and 41.

In yet another aspect of the invention, compositions that comprise at least one of the heavy chain and light chain variable region of an antibody are provided which recognize epitopes on the extracellular domains of human CXCR4.

In one embodiment, the composition comprises an antibody that binds to loop 6 of human CXCR4. In a variation, the antibody is capable of inhibiting HIV-1 infection of human cells. In another variation, the antibody is capable of inhibiting chemotaxis of cells, optionally human cancer cells, optionally human breast cancer cells.

It is noted the antibody may be a polyclonal or a monoclonal antibody, including but not limited to fully assembled antibody, single chain antibody, Fab fragment, and chimeric antibody. For example, the antibody is a single chain antibody encoded by DNA SEQ ID NO: 59 or 62.

Optionally, the heavy chain variable region of the antibody comprises an amino acid sequence with SEQ ID NO: 60 or 63.

Optionally, the light chain variable region of the antibody comprises an amino acid sequence with SEQ ID NO: 61 or 64.

The antibody of the present invention may be produced by expression in bacteria, yeast, plant, and animal cells in any form including but not limited to single chain, Fab, full length IgA, secretion form sIgA, or IgG.

The antibody of present invention may be used for the prevention or treatment of HIV infection. For example, the antibodies against human CCR5 may be administered to an individual with high risk of HIV infection or already infected with HIV to block the entry of HIV-1 into the cells.

The antibody of present invention may also be conjugated with a molecule such as an antiviral drug and a radio-isotope to specifically target cells expressing human CCR5 and/or CXCR4.

The antibody of the present invention may be used in a therapy for the treatment of various diseases such as cancer, autoimmune diseases, and viral infection. The antibody may also be used in a combination therapy in conjunction with other therapeutic agents such as anti-viral agents (e.g., nucleoside or non-nucleoside HIV reverse transcriptase inhibitors, HIV protease inhibitors, and HIV integrase inhibitors), and anti-neoplastic agents.

Examples of the nucleoside HIV reverse transcriptase inhibitor include, but are not limited to zidovudine (AZT), didanosine (ddI), zalcitabine (ddC), lamivudine (3TC), stavudine (d4T), abacavir (1592U89), and adefovir dipivoxil (bis(POM)-PMEA). Examples of the non-nucleoside HIV reverse transcriptase inhibitor include, but are not limited to neviparine (BI-RG-587), delavirdine (BHAP, U-90152) and efavirenz (DMP 266). Examples of the HIV protease inhibitors include, but are not limited to indinavir (MK-639), ritonavir (ABT-538), saqinavir (Ro-31-8959), nelfinavir (AG-1343), and amprenavir (141W94).

Examples of anti-neoplastic agents include, but are not limited to, alkylating agents (e.g., cyclophosphamide and cisplatin), antibiotic agents (e.g., doxorubicin, mitomycin C, and bleomycin), antimetabolic agents (e.g., fluorouracil (5-FU) and methotrexate), hormonal agents (e.g., tamoxifen), plant-derived agents (paclitaxel, vincristine and camptothecin), and biologic agents (e.g., monoclonal antibodies such as HERCEPTIN® (Trastruzumab) and RITUXAN® (Rituximab), and cytokines).

The antibody of the present invention may be administered to a mammal, preferably a human, via a variety of routes, including but not limited to, orally, parenterally, intraperitoneally, intravenously, intraarterially, topically, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The antibody may also be delivered to the host locally (e.g., via stents or cathetors) and/or in a timed-release manner.

Additionally, the antibody of the present invention may be used for diagnosis of diseases associated with membrane proteins interactions such as CXCR4 and CCR5, the co-receptors of HIV. Moreover, the antibody may be used in assays for screening therapeutic agents against these diseases.

BRIEF DESCRIPTION OF FIGURES

FIG. 1A shows the amino acid sequence of human CCR5.

FIG. 1B shows the amino acid sequences of peptide fragments derived from human CCR5 that are used as target peptides for eliciting antibody according to the present invention.

FIG. 5 shows DNA and amino acid sequences of four distinct scFv antibodies against human CCR5 fragments.

FIG. 6 shows DNA and amino acid sequences of variants of the four scFv antibodies against human CCR5 fragments.

FIG. 7 shows a homology alignment of amino acid sequences of three scFv antibodies against human CCR5 Loop6.

FIG. 8 shows amino acid sequences of $V_H$ and $V_L$ of the four scFv antibodies against human CCR5 fragments.

FIG. 15 shows DNA sequence, amino acid sequences of $V_H$ and $V_L$ of single chain antibodies Ab124 and Ab125.

DETAILED DESCRIPTION OF THE INVENTION

Figure 1C:
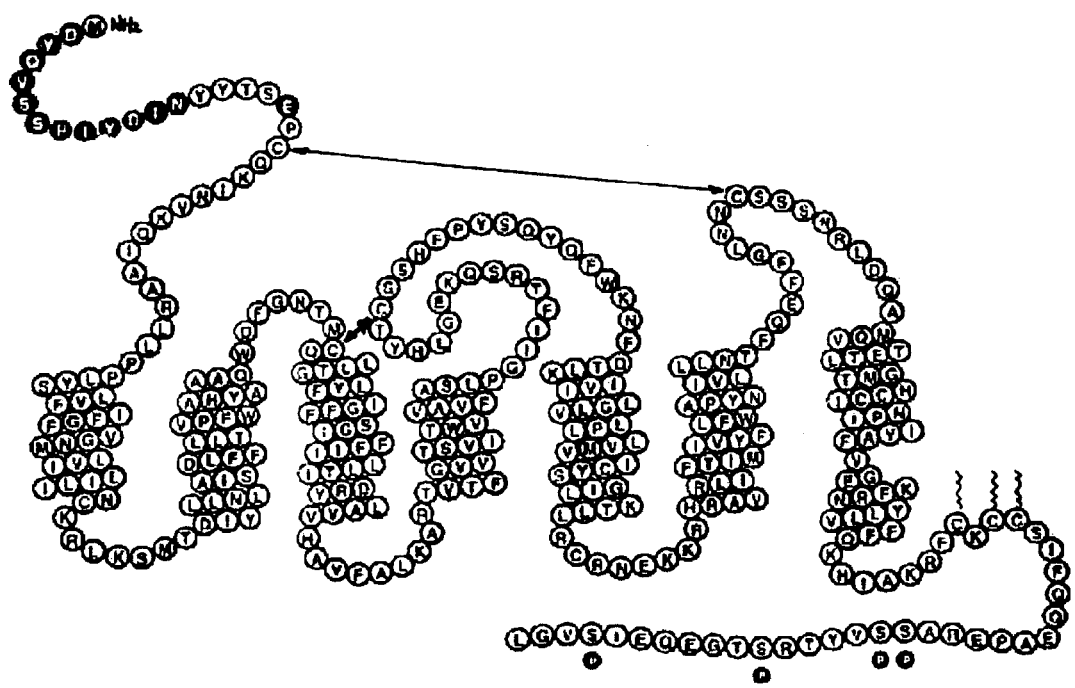
FIG. 1C shows and a model of the secondary structure of human CCR5.

The present invention provides innovative methods for efficient, high throughput screening of antibody library against a wide variety of target proteins, especially membrane proteins. In particular, the methods can be used to systematically and efficiently screen human antibody against epitopes on a target protein and select for antibodies with high affinity and efficacy in regulating the biological functions of the target protein. More particularly, fully human antibodies can be selected by using these methods to target therapeutically significant membrane proteins, such as cell surface co-receptors for HIV envelope protein (e.g., CXCR4 and CCR5).

Membrane proteins are generally considered to be evasive targets for screening agents for therapeutic intervention and rational drug design because of difficulties associated with isolation and purification, as well as the structural uncertainty of the isolated protein adopted in vitro. As described in the section of "Background of the Invention", skilled artisans resorted to using cells expressing the whole protein of the membrane protein such as CCR5 as an immunogen to elicit monoclonal antibody against it.

Surprisingly, the inventors discovered that peptide fragments of a membrane protein, as opposed to the whole protein, can be excellent targets against which high affinity antibody can be selected in a yeast two-hybrid system. The peptide fragment is expressed as a target fusion protein with the DNA-binding domain (BD) (or the activation domain (AD)) of a transcription activator in yeast cells. A library of fully human single-chain antibody is expressed as tester fusion proteins with the AD (or the BD) of the transcription activator in the same yeast cells. Binding of the antibody to the peptide target triggers expression of a reporter gene in the yeast cell, which facilitates identification and isolation of the clones containing the monoclonal human antibody. The ability of the selected monoclonal antibodies in blocking HIV entry and inhibiting infection has been validated. See the "EXAMPLE" section below.

Not wishing to be bound by the theory, the inventors believe that a peptide fragment derived from a membrane protein, when fused with a heterologous protein that acts like a chaperon to stabilize the conformation adopted by the peptide in isolation from the membrane protein, can serve as an immunogen to elicit antibody in an animal or as a target ligand in screening assays in vitro. The fusion protein formed by the peptide and the chaperon protein may present the peptide in a conformation similar to that adopted by the peptide in its native context, i.e., in the membrane protein located on the cell. In particular, extracellular loops adopted by stretches of peptide sequences in the membrane protein are attractive targets because these loops can serve as accessible epitopes for extracellular binding with antibodies to block downstream signal transduction mediated by the membrane protein. This feature is desirable for therapeutic and diagnostic applications targeting cells expressing the membrane protein.

In one aspect, a method is provided for eliciting antibodies against a membrane protein in a non-human animal. The method comprises: immunizing a non-human animal with an antigen that is a fusion protein between a peptide fragment of a target membrane protein and a heterologous chaperon protein that stabilizes the peptide fragment.

The step of immunizing the animal may include injecting the antigen directly into the animal. For example, the antigen may be injected into a mouse to elicit polyclonal antibodies, or monoclonal antibodies by using a conventional hybridoma technology, examples of which are described in detail in Section 2 below. The animal may be a natural animal, a transgenic animal that has been genetically modified to produce human antibodies, such as XENOMOUSE® and HuMab Mouse, or a transchromosome (TC) mouse (Tomizuka et al. (2000) Proc Natl Acad Sci USA. 97:722–727. This document, and all documents cited to herein, are incorporated by reference as if fully reproduced below).

For example, the fusion protein formed by the peptide and the chaperon protein may be administered into a XENOMOUSE® by following protocols described in U.S. Pat. Nos. 6,075,181 and 6,114,598 which are incorporated herein by reference. Briefly, two to six xenomice aged 6–30 weeks are age-matched and immunized intraperitoneally with 10–100 µg of the fusion protein in complete Freund's adjuvant for primary immunization and in incomplete Freund's adjuvant for subsequent injections. The mice received 6 injections 2–3 weeks apart. Serum titers are determined after the second dose and following each dose thereafter. Bleeds are performed 6–7 days after injections from the retrobulbar plexus. The blood is allowed to clot at room temperature for about 2 hours and then incubated at 4° C. for at least 2 hours before separating and collecting the sera. The sera of the immunized xenomice (or the supernatants from immortalized B cells) are titrated for antigen specific human antibodies using a standard ELISA assay. In this assay, the antigen used for immunization, i.e., the fusion protein, was immobilized onto wells of microtiter plates. The plates are washed and blocked and the sera (or supernatants) are added as serial dilutions for 1–2 hours of incubation. After washing, bound antibody having human characteristics are detected by adding the appropriate antispecies Ig (typically antihuman κ or antihuman µ) conjugated to horseradish peroxidase (HRP) for one hour. The bound antibodies may be tested for murine characteristics using antimurine antibodies, typically antimurine γ. After again washing, the chromogenic reagent o-phenylene diamine (OPD) substrate and hydrogen peroxide are added and the plates are read 30 minutes later at 492 nm using a microplate reader. The hybridoma secreting the target antigen-binding antibodies is used to obtain the cDNA encoding fully human variable regions. Such xenogeneic antibodies can then converted to fully human antibodies by cloning the variable region sequences into plasmids containing the coding sequences for human antibodies. Queens et al. Proc. Natl. Acad. Sci. (1989) 86:10029.

Optionally, the step of immunizing the animal may include transfecting the animal with an expression vector encoding the antigen. For example, DNA sequence encoding the antigen can be inserted into a mammalian expression vector or a viral vector (e.g., retroviral, adnoviral, and adeno-associated viral vectors) and the resulting expression vector can be injected into the animal where the expression of the antigen by the vector elicits immune responses to the antigen. Antibodies can then be isolated from the serum of the animal and used to target the membrane protein for therapeutic or diagnostic purposes.

In another aspect, a method is provided for selecting antibody against a membrane protein in vitro. The method comprises: contacting a library of antibodies with an antigen that is a fusion protein between a peptide fragment of a target membrane protein and a heterologous chaperon protein that stabilizes the peptide fragment; and selecting the antibodies that bind to the antigen.

The library of antibodies may be a library of antibodies mixed in solution, immobilized to a substrate in the form of an array, or displayed by mRNA, ribosome, phage, and cells such as yeast cells.

The antibodies in the library may be in the form of a single chain antibody, Fab antibody and fully assembled antibody.

The chaperon protein may be any protein or a domain of a protein that is heterologous to the membrane protein and capable of stabilizing the fused peptide, for example, structurally stabilizing the conformation of the peptide under the condition of the immunization or screening process and/or preventing degradation of the peptide. Preferably, the chaperon protein may be a DNA binding domain (BD) or an activation domain (AD) of a transcription factor. More preferably, the chaperon protein may include Gal4 DNA binding domain, LexA binding domain, lambda cl DNA binding domain, cdc25 or Sos (guanine nucleotide exchange factor), T18 bacterial protein, T25 bacterial protein, the alpha and omega fragments of beta-lactamase, glutathion-S-transferase (GST) and thioredoxin.

In yet another aspect, the present invention provides a method for selecting monoclonal single chain antibody (scFv) against a peptide target. A single chain antibody generally includes a heavy chain variable region ($V_H$) of antibody covalently linked to a light chain variable region ($V_L$) of antibody via a peptide linker. In one embodiment, the method comprising:

expressing a library of scFv fusion proteins in yeast cells, each scFv fusion protein comprising either an activation domain or a DNA binding domain of a transcription activator and a scFv, the scFv comprising a $V_H$ of antibody whose sequence varies within the library, a $V_L$ of antibody whose sequence varies within the library independently of the $V_H$, and a linker peptide which links the $V_H$ and $V_L$;

expressing a target fusion protein in the yeast cells expressing the scFv fusion proteins, the target fusion protein comprising either the DNA binding domain or the activation domain of the transcription activator which is not comprised in the scFv fusion proteins, and a target peptide having a length of 5–100 amino acid residues (aa); and selecting those yeast cells in which a reporter gene is expressed, the expression of the reporter gene being activated by a reconstituted transcriptional activator formed by binding of the scFv fusion protein to the target fusion protein.

According to the embodiment, the diversity of the library scFv fusion proteins is preferably higher than $1 \times 10^4$, more preferably higher than $1 \times 10^6$, and most preferably higher than $1 \times 10^7$.

Also according to the embodiment, the length of the target peptide is preferably 10–80 aa, more preferably 20–60 aa, and most preferably 30–50 aa.

Also according to the embodiment, the target peptide is preferably a fragment of a membrane protein, more preferably an extracellular domain of a membrane protein, and most preferably an extracellular loop of a transmembrane protein.

By using the methods of present invention, antibodies with high affinity and specificity can be selected against the target peptide expressed as a fusion protein in vivo and in vitro. In particular, compared to conventional approaches of generating monoclonal antibody by hybridoma technology and the recently developed XENOMOUSE® technology, the inventive method for screening in yeast may provide a more efficient and economical way to screen for fully human antibodies against virtually any target peptide in a much shorter period of time. More importantly, the screening of the antibody libraries can be readily adopted for high throughput screening in vivo.

In a particular embodiment, the method of the present invention has been used for screening fully human antibody library against HIV coreceptors such as CCR5 and CXCR4 in yeast. Significantly, single chain antibodies against fragments of CCR5 have been selected and demonstrated to bind to human CCR5 with high affinity and inhibit HIV-1 infection at sub-nanomolar concentrations.

The overall process of screening in yeast is very efficient and high throughput. For any targeted membrane protein, each domain (or fragment) of the protein can be can systematically screened against the same library of human antibody with high diversity ($>1 \times 10^7$). Since the peptide comprising the domain is expressed intracellularly and screened for binding with the library of antibody intracellularly, the peptide needs not be isolated or synthesized in vitro, thus greatly simplifying the process and reducing labor and cost.

Further, the fast proliferation rate of yeast cells and ease of handling makes a process of "molecular evolution" dramatically shorter than the natural process of antibody affinity maturation in a mammal. Therefore, antibody repertoires with extremely high diversity can be produced and screened directly against the fusion protein containing the target peptide in yeast cells at a much lower cost and higher efficiency than prior processes such as the painstaking, stepwise "humanization" of monoclonal murine antibodies isolated by using the conventional hybridoma technology (a "protein redesign") or the recently-developed XENOMOUSE™ technology.

According to the "protein redesign" approach, murine monoclonal antibodies of desired antigen specificity are modified or "humanized" in vitro in an attempt to reshape the murine antibody to resemble more closely its human counterpart while retaining the original antigen-binding specificity. Riechmann et al. (1988) Nature 332:323–327. This humanization demands extensive, systematic genetic engineering of the murine antibody, which could take months, if not years. Additionally, extensive modification of the backbone of the murine monoclonal antibody may result in reduced specificity and affinity.

In comparison, by using the inventive method for screening in yeast, fully human antibodies with high affinity to a specified target peptide can be screened and isolated directly from yeast cells without going through site-by-site modification of the antibody, and without sacrifice of specificity and affinity of the selected antibodies.

By using the methods of the present invention, any peptide fragment derived from the target protein can be expressed as a fusion protein with a chaperon protein, such as a DNA-binding domain (or an activation domain) of a transcription activator and selected against the library of antibody in vivo or in vitro (e.g., in a yeast-2-hybrid system). Moreover, multiple peptide targets may be arrayed in multiple-well plates and screened against the library of antibodies in a high throughput and automated manner.

Various aspects of the present invention are described in detail in the following sections.

1. Peptide Fragment from a Membrane Protein as the Target Peptide

In a preferred embodiment, the target peptide is a fragment of a membrane protein. The target peptide is expressed in yeast as a target fusion protein with either a DNA binding domain or an activation domain of a transcription activator which is not comprised in the scFv fusion proteins. The epitope on the target peptide is presented by the target fusion protein in yeast and recognized by some member(s) in the library of scFv fusion proteins. Such interactions trigger expression of a reporter gene within the same cell, allowing identification of the yeast clones expressing the binding scFv fusion protein.

Member protein is a protein that is associated with the plasma membrane of a cell. Plasma membrane encloses the cell by forming a selective permeability barrier, defines its boundaries, and maintains the essential differences between the cytosol and the extracellular environmen. The plasma membrane consists lipids, proteins, and some carbohydrates. Lipids form a bilayer in which the membrane proteins are embedded to varying degrees.

Different membrane proteins are associated with the membranes in different ways. Many membrane proteins extend through the lipid bilayer, with part of their mass on either side. These transmembrane proteins are amphipathic, having regions that are hydrophobic and regions that are hydrophilic. Their hydrophilic regions are exposed to water on one or the other side of the membrane. Other membrane proteins are located entirely in the cytosol and are associated with the bilayer only by means of one or more covalently attached fatty acid chains or other types of lipid chains called prenyl groups. Yet other membrane proteins are entirely exposed at the external cell surface, being attached to the bilayer only the covalent linkage (e.g., via a specific oligosaccharide) to phosphatidylinositol in the outer lipid monolayer of the plasma membrane.

In a more preferred embodiment, the membrane protein is a transmembrane protein. Typically, a transmembrane protein has its cytoplasmic and extracellular domains which are separated by the membrane-spanning segments of the polypeptide chain. The membrane-spanning segments contact the hydrophobic environment of the lipid bilayer and are composed largely of amino acid residues with non-polar side chains. The great majority of transmembrane proteins are glycosylated. The oligosaccharide chains are usually present in the excellular domain. Further, the reducing environment of the cytosol prevents the formation of intrachain (and interchain) disulfide (S-S) bonds between cysteine residues on the cytosolic side membranes. These disulfide bonds do form on the extracellular side, e.g., between the N-terminal domain and an extracellular loop.

Transmembrane proteins are notoriously difficult to crystallize for X-ray structural studies. The folded three-dimensional structures are quite uncertain for the isolated forms of these proteins. Thus, these features present a problem in the attempt to use the whole transmembrane protein as a target for isolating molecules that would bind to it in vitro.

According to the present invention, a peptide fragment derived from one of the extracellular domains of the transmembrane protein could serve as the target peptide. Antibody selected by using the screening methods of present invention binds to the exacelluar cellular domain, thereby effectively blocking interactions of the transmembrane protein with its excellular ligand.

Examples of the membrane protein include, but are not limited to, receptors for growth factors (e.g., vascular endothelial growth factor (VEGF), transforming growth factor (TGF), fibroblast growth factor (FF), platelet derived growth factor (PDGF), insulin-like growth factor), insulin receptor, MHC proteins (e.g. class I MHC and class II MHC protein), CD3 receptor, T cell receptors, cytokine receptors (e.g., interleukin (IL)-1, IL-2, IL-3, IL-4, IL-5, IL-6, IL-7, IL-8, IL-9, IL-10, IL-11, IL-12, IL-13, IL-14, IL-15 receptors), tyrosine-kinase-associated receptors such as Src, Yes, Fgr, Lck, Flt, Lyn, Hck, and Blk, and G-protein coupled receptors such as receptors for the hormone relaxin (LGR7 and LGR8) and chemokine receptors (e.g., CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CX3CR1, and XCR1), PSGR,s beta1-adrenergic receptor, beta2-adrenergic receptor, parathyroid hormone (PTH) receptor, EDG1, G10d, opioid receptors, neutensin recetpors, neuropeptide Y (NPY) receptors, melatonin receptor, adrenocorticotrophin (ACTH) receptor, leukotriene receptors, 5-hydroxytryptamine (5-HT, or serotonin) receptors (including 5-TH1a, 5-TH1b, 5-TH1d, 5-TH1e, 5-TH1f, 5-TH2a, 5-TH2b, 5-TH2c, 5-TH3, 5-TH4, 5-TH5 receptors), FSH receptor, LH/hCG recetpor, TSH receptor, formyl-methionyl peptide (fMLP) receptors (FPR1 receptor, FPR2 receptor, FPR3 receptor), GABA receptors, endothelin (ET) receptors, sarafotoxin receptors, dopamin receptors (D1 receptor, D2 receptor, D3 receptor, D4 receptor, D5 receptor), cannabinoid receptor, CGRP1 receptor, CGRP2 receptor, amylin receptor, calcitonin receptor, C5a receptor, bradykinin receptors (B1, B2 and B3 receptors), bombesin Receptors (BB1, BB2 and BB3 receptors), angiotensin receptors (AT1a, AT1b and AT2 receptors), adrenaline and noradrenaline receptors (or adrenoceptors), acetylcholine Receptors, platelet activating factor (PAF) receptor, prostanoid receptors (DP, EP1, EP2, EP3, FP, IP and TP receptors), somatostanin receptors (SS1, SS2, SS3, SS4 receptors), tachykinin Recetpors (NK1, NK2 and NK3 receptors), thrombin receptor, vasoactive Intestinal polypeptide (VIP) receptor family (GRF, PACAP, secretin, VIP and helodermin-preferring receptors), stresscopin receptor, urocortin receptor, corticotropin releasing hormone receptors, LGR4, LGR5, LGR6, LGR7 and LGR8, and GPCR orphan receptors designated as GPR1-58 at GenBank.

G protein-coupled receptors (GPCR) are a superfamily of transmembrane proteins that play important roles in the signal transduction process of a cell. GPCR mediates the cellular responses to an enormous diversity of signaling molecules, including hormones, neurotransmitters, and local mediators. The signal molecules vary in their structure and function, including proteins, small peptides, as well as amino acid and fatty acid derivatives. See reviews by Watson S., and Arkinstall S.: "The G-Protein Linked Receptor Facts Book". 1994, Academic Press, Harcourt Brace & Company, Publishers. London, San Diego, New York; Proudfoot A. E. I.: "Chemokine Receptors: Multifaceted Therapeutic Targets." 2002, Nature Review Immunology 2:106–115; and Ji T. H., Grossman M. and Ji I.: "G Protein-coupled Receptors." 1998, J. Biol. Chem. 273:17299–17302. These documents, and all documents cited to herein, are incorporated by reference as if fully reproduced below.

For example, receptors for the hormone relaxin (LGR7 and LGR8) have been found recently to be G-protein coupled receptors. Hsu et al. (2002) Science 295:671–674. Relaxin is a hormone important for the growth and remodeling of reproductive and other tissues during pregnancy. Hsu et al demonstrated that two orphan heterotrimeric guanine nucleotide binding protein (G-protein) receptors, LGR7 and LGR8 are capable of mediating the action of relaxin through an adenosine 3',5'-monophosphate (cAMP)-dependent pathway distinct from that of the structurally related insulin and insulin-like growth factor. These receptors for relaxin are implicated to play roles in reproductive, brain, renal, cardiovascular and other functions.

Despite the chemical and functional diversity of the signaling molecules that bind to them, all of GPCRs share a structural similarity in that the polypeptide chain threads back and forth across the lipid bilayer several times, e.g., seven times to form 7 transmembrane domains which are connected by 3 extracellular loops and 3 intracellular loops.

Both CCR5 and CXCR4 are chemokine receptors are members of the GPCR superfamily. CCR5 is a receptor for several CC chemokines such as MIP-1α (also named GOS19, LD78, pAT464 gene product, TY5 (murine) and SISα (murine)), MIP-1β (also named Act-2, G-26, pAT744 gene product, H-400 (murine) and hSISγ (murine)) and RANTES (regulated on activation, normal T cell expressed and secreted, or CCL5). Cocchi et al. (1995) Science 270: 1811–1815; and Mellado et al. (2001) Annu. Rev. Immunol. 19:397–421. CXCR4 (also named LESTR or fusin before) is a human chemokine receptor with the C-X-C motif, and is highly expressed in leukocytes. Loetscher M, et al (1994) J Biol Chem. 269:232–237. The lymphocyte chemoattractant stromal cell derived factor-1 (or SDF-1) or CXCL12 is a ligand for CXCR4 (Bleul C C, et al. (1996) Nature. 382: 829–833). CXCR4 acts as a coreceptor of HIV-1 (Feng Y, (1996) Science 272:872–877). Its expression is also correlated with cancer, including prostate cancer (Taichman R S, et al (2002) Cancer Res. 62:1832–1837) and breast caner metastasis (Muller A, et al (2001) Nature. 410:50–56; and Moore M A (2001) Bioessays. 23:674–676). Thus, the inventive methodology disclosed herein can be used to generate antibodies against these chemokine receptors. The resultant antibodies can then be used for the prevention and/or treatment of HIV infection, cancer and other diseases associated with abnormal chemokine activities. As will be shown in the Example section below, human monoclonal single chain antibodies against CCR5 and CXCR4 were generated using the inventive methods and used to inhibit HIV infection of peripheral blood mononuclear cells and chemotaxis in breast cancer cells, respectively.

FIG. 1A shows the amino acid sequence of human CCR5 with 7 transmembrane domains that are connected by loops 2, 4, and 6 which are extracellular loops and by loops 1, 3, 5 which are intracellular loops. FIG. 1B shows a model of the secondary structure of human CCR5. Blanpain et al. (1999) J. Biol. Chem. 274:34719–34727.

In particular, peptides derived from excellular loops of the membrane protein could serve an ideal target for screening against the library of antibody.

Other than CCR5 and CXCR4, examples of a chemokine receptor or a chemokine receptor-like orphan receptor also include, but are not limited to, CCR1, CCR2b, CCR3, CCR4, CCR8, CXCR1, CXCR2, CXCR3, CX$_3$CR1, STRL33/BONZO and GPR15/BOB. Berger, E. a. (1997) AIDS 11, Suppl. a: S3–S16; and Dimitrov, D.S. (1997) Cell 91: 721–730. Each or a set of these HIV coreceptors can mediate entry of different strains of HIV virus into the host cell.

By using the method of the present invention, high affinity monoclonal antibodies can be generated against a peptide fragment of a chemokine receptor efficiently and in a high throughput manner. Administering one or more of these antibodies to a host may offer protection against or inhibit infection of HIV strains with broad-spectrum tropisms.

Other membrane proteins described above, the target peptide may be derived from any protein. For example, the target peptide may be derived from a disease-associated antigen, such as tumor surface antigen such as B-cell idiotypes, CD20 on malignant B cells, CD33 on leukemic blasts, and HER2/neu on breast cancer. Antibody selected against these antigens can be used in a wide variety of therapeutic and diagnostic applications, such as treatment of cancer by direct administration of the antibody itself or the antibody conjugated with a radioisotope or cytotoxic drug, and in a combination therapy involving coadministration of the antibody with a chemotherapeutic agent, or in conjunction with radiation therapy.

Alternatively, the target peptide may be derived from a growth factor receptor. Examples of the growth factor include, but are not limited to, epidermal growth factors (EGFs), transferrin, insulin-like growth factor, transforming growth factors (TGFs), interleukin-1, and interleukin-2. For example, high expression of EGF receptors have been found in a wide variety of human epithelial primary tumors. TGF-α have been found to mediate an autocrine stimulation pathway in cancer cells. Several murine monoclonal antibody have been demonstrated to be able to bind EGF receptors, block the binding of ligand to EGF receptors, and inhibit proliferation of a variety of human cancer cell lines in culture and in xenograft medels. Mendelsohn and Baselga (1995) "Antibodies to growth factors and receptors", in Biologic Therapy of Cancer, 2$^{nd}$ Ed., J B Lippincott, Philadelphia, pp607–623; Leget and Czuczman (1998) "Use of rituximab, the new FDA-approved antibody'. Curr Opin Oncol. 10:548–551; and Goldenberg (1999) "Trastuzumab, a recombinant DNA-derived humanized monoclonal antibody, a novel agent for the treatment of metastatic breast cancer. Clin Ther. 21:309–318). Thus, fully human antibodies selected against these growth factors by using the method of the present invention can be used to treat a variety of cancer.

The target peptide may also be derived from a cell surface protein or receptor associated with coronary artery disease such as platelet glycoprotein lib/IIIa receptor, autoimmune diseases such as CD4, CAMPATH-1 and lipid A region of the gram-negative bacterial lipopolysaccharide. Humanized antibodies against CD4 has been tested in clinical trials in the treatment of patients with mycosis fungoides, generalized postular psoriasis, severe psoriasis, and rheumatoid arthritis. Antibodies against lipid A region of the gram-negative bacterial lipopolysaccharide have been tested clinically in the treatment of septic shock. Antibodies against CAMPATH-1 has also been tested clinically in the treatment of against refractory rheumatoid arthritis. Thus, fully human antibodies selected against these growth factors by using the method of the present invention can be used to treat a variety of autoimmune diseases (Vaswani et al. (1998) "Humanized antibodies as potential therapeutic drugs" Annals of Allergy, Asthma and Immunology 81:105–115); inflammation (Present et al. (1999) "Infliximab for the treatment of fistulas in patients with Crohn's disease" N Engl J Med. 340: 1398–1405); and immuno-rejection in transplantation (Nashan et al. (1999) "Reduction of acute renal allograft rejection by daclizumab. Daclizumab Double Therapy Study Group", Transplantation 67:110–115.

The target peptide may also be derived from proteins associated with human allergic diseases, such as those inflammatory mediator protein, e.g. Interleukin-1 (IL-1), tumor necrosis factor (TNF), leukotriene receptor and 5-lipoxygenase, and adhesion molecules such as V-CAM/VLA-4. In addition, IgE may also serve as the target antigen because IgE plays pivotal role in type I immediate hypersensitive allergic reactions such as asthma. Studies have shown that the level of total serum IgE tends to correlate with severity of diseases, especially in asthma. Burrows et al. (1989) "Association of asthma with serum IgE levels and skin-test reactivity to allergens" New Engl. L. Med. 320: 271–277. Thus, fully human antibodies selected against IgE by using the method of the present invention may be used to reduce the level of IgE or block the binding of IgE to mast cells and basophils in the treatment of allergic diseases without having substantial impact on normal immune functions.

The target peptide may also be derived from a viral surface or core protein which may serve as an antigen to trigger immune response of the host. Examples of these viral proteins include, but are not limited to, glycoproteins (or surface antigens, e.g., GP120 and GP41) and capsid proteins (or structural proteins, e.g., P24 protein); surface antigens or core proteins of hepatitis A, B, C, D or E virus (e.g. small hepatitis B surface antigen (SHBsAg) of hepatitis B virus and the core proteins of hepatitis C virus, NS3, NS4 and NS5 antigens); glycoprotein (G-protein) or the fusion protein (F-protein) of respiratory syncytial virus (RSV); surface and core proteins of herpes simplex virus HSV-1 and HSV-2 (e.g., glycoprotein D from HSV-2). For example, humanized monoclonal antibody has been developed for the prevention of respiratory syncytial virus (RSV) infection. Storch (1998) "Humanized monoclonal antibody for prevention of respiratory syncytial virus infection" Pediatrics. 102:648–651.

The target peptide may also be derived from a mutated tumor suppressor gene that have lost its tumor-suppressing function and may render the cells more susceptible to cancer. Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. Thus, fully human antibodies selected against a mutated tumor suppressor gene product by using the method of the present invention can be used to block the interactions of the gene product with other proteins or biochemicals in the pathways of tumor onset and development.

2. Antibody Against Loop 6 of CCR5

The inventors also discovered that certain fragments derived from loop 6 of CCR5 (designated hereafter "CCR5 Loop 6") present excellent epitopes for recognition by antibodies. The epitope(s) on CCR5 Loop 6 can be used to elicit antibody by using the method of present invention or other methods for generating antibody known in the art.

CCR5 Loop 6 includes amino acid residue aa 261–277: QEFFGLNNCSSSNRLDQ [SEQ ID NO:2] (shown in FIG. 1A). As demonstrated in the section of "EXAMPLE", a peptide fragment containing most of the Loop 6 region and a portion of transmembrane domain 7, EFFGLNNCS SSNRLDQAMQ VTETLGMTHC [SEQ ID NO:3], could elicit monoclonal antibodies that bind to CCR5 with high affinity and inhibit HIV-1 infection at sub-nanomolar concentrations.

According to the present invention, a peptide comprising a substantial portion of Loop 6 may serve as an epitope for elicit antibodies by using the method of the present invention or conventional methods such as hybridoma techniques and bacteriophage display panning. In particular, the loop 6 peptide may be fused with a chaperon protein such as Gal4 DNA binding domain to form a fusion protein. Such a fusion protein can be used as an immunogen for eliciting antibodies in animals or as a ligand for screening an antibody library in vitro. The antibodies against CCR5 Loop 6 include but are not limited to polyclonal, monoclonal, Fab fragments, single chain antibodies, chimeric antibodies (e.g., humanized antibodies), etc.

For the production of antibodies against CCR5 Loop 6, various host animals may be immunized by injection with an immunogen containing a peptide derived from CCR5 Loop 6. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a peptide derived from CCR5 Loop 6 or its fusion with a chaperon protein, or an antigenic functional derivative thereof. For the production of polyclonal antibodies, host animals such as those described above, may be immunized by injection with a peptide comprising a portion of CCR5 Loop 6 supplemented with adjuvants as also described above. It may be useful to conjugate the peptide to a protein that is immunogenic in the species to be immunized, e.g., keyhole limpet hemocyanin (KLH), serum albumin, bovine thyroglobulin, or soybean trypsin inhibitor, by using a bifunctional or derivatizing agent, for example, maleimidobenzoyl sulfosuccinimide ester (conjugation through cysteine residues), N-hydroxysuccinimide (through lysine residues), glutaraldehyde, succinic anhydrid or $SOCl_2$.

Briefly, animals are immunized against CCR5 Loop 6 peptide or its immunogenic conjugates by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ or ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with conjugate of the same antigen, but conjugated to a different protein and/or through a different cross-linking reagent.

Conjugates can also be made in recombinant cell culture as protein fusions. In addition, aggregating agents such as alum are suitably used to enhance the immune response.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein (1975) Nature 256:495–497; and U.S. Pat. No. 4,376,110, the human B-cell hybridoma technique (Kosbor et al. (1983) Immunology Today 4:72; Cole et al. (1983) Proc. Natl. Acad. Sci. USA 80:2026–2030, and the EBV-hybridoma technique (Cole et al. (1985) Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo.

In the hybridoma method, a mouse or other appropriate host animal, such as hamster or macaque monkey, is immunized as herein above described to elicit lymphocytes that produce or are capable of producing antibodies that will specifically bind to the antigen used for immunization. Alternatively, lymphocytes may be immunized in vitro. Lymphocytes are then fused with myeloma cells using a suitable fusing agent, such as polyethylene glycol, to form a hybridoma cell. Goding (1986) "Monoclonal Antibodies: Principles and Practice", pp. 59–103, Academic Press.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthaine guanine phosphoribosyl transferase (HGPRT or HPRT), the culture medium for the hybridoma typically will include hypoxanthine, aminopterin, and thymidine (HAT medium), which substances prevent the growth of HGPRT-deficient cells.

Preferred meyloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors, SP-2 or X63-Ag8–653 cells available from the American Typeure Collection (ATCC), Rockville, Md. Human myeloma and mouse-human heteromyeloma cell lines also have been described for the production of human monoclonal antibodies.

Culture medium in which hybridoma cell are growing is assayed for production of monoclonal antibodies directed against CCR5 Loop 6 antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods. Suitable culture media for this purpose include, for example, DEME or RPMI-1640 medium. In addition, hybridoma cell may be grown in vivo as ascites tumors in an animal.

The monoclonal antibodies secreted by the subclones are suitably separated from the culture medium, ascites fluid, or serum, by conventional immunoglobulin purification procedures such as protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transferred into host cell such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

Monoclonal antibodies against CCR5 Loop 6 may also be generated by using bacteriophage display. Combinatorial libraries of antibodies have been generated in bacteriophage lambda expression systems which are screened as bacteriophage plaques or as colonies of lysogens (Huse et al. (1989) Science 246: 1275; Caton and Koprowski (1990) Proc. Natl. Acad. Sci. (U.S.A.) 87: 6450; Mullinax et al (1990) Proc. Natl. Acad. Sci. (U.S.A.) 87: 8095; Persson et al. (1991) Proc. Natl. Acad. Sci. (U.S.A.) 88: 2432). Various embodiments of bacteriophage antibody display libraries and lambda phage expression libraries have been described (Kang et al. (1991) Proc. Natl. Acad. Sci. (U.S.A.) 88: 4363; Clackson et al. (1991) Nature 352: 624; McCafferty et al. (1990) Nature 348: 552; Burton et al. (1991) Proc. Natl. Acad. Sci. (U.S.A.) 88: 10134; Hoogenboom et al. (1991) Nucleic Acids Res. 19: 4133; Chang et al. (1991) J. Immunol. 147: 3610; Breitling et al. (1991) Gene 104: 147; Marks et al. (1991) J. Mol. Biol. 222: 581; Barbas et al. (1992) Proc. Natl. Acad. Sci. (U.S.A.) 89: 4457; Hawkins and Winter (1992) J. Immunol. 22: 867; Marks et al. (1992) Biotechnology 10: 779; Marks et al. (1992) J. Biol. Chem. 267: 16007; Lowman et al (1991) Biochemistry 30: 10832; Lerner et al. (1992) Science 258: 1313). Also see review by Rader, C. and Barbas, C. F. (1997) "Phage display of combinatorial antibody libraries" Curr. Opin. Biotechnol. 8:503–508.

Various scFv libraries displayed on bacteriophage coat proteins have been described. Marks et al. (1992) Biotechnology 10: 779; Winter G and Milstein C (1991) Nature 349: 293; Clackson et al. (1991) op.cit.; Marks et al. (1991) J. Mol. Biol. 222: 581; Chaudhary et al. (1990) Proc. Natl. Acad. Sci. (USA) 87: 1066; Chiswell et al. (1992) TIBTECH 10: 80; and Huston et al. (1988) Proc. Natl. Acad. Sci. (USA) 85: 5879.

Generally, a phage library is created by inserting a library of a random oligonucleotide or a cDNA library encoding antibody fragment such as $V_L$ and $V_H$ into gene 3 of M13 or fd phage. Each inserted gene is expressed at the N-terminal of the gene 3 product, a minor coat protein of the phage. As a result, peptide libraries that contain diverse peptides can be constructed. The phage library is then affinity screened against immobilized target molecule of interest, such as a peptide comprising a portion of CCR5 Loop6 or its fusion with a chaperon protein, and specifically bound phages are recovered and amplified by infection into *Escherichia coli* host cells. Typically, the target molecule of interest, such as a peptide comprising a portion of CCR5 Loop6 or its fusion with a chaperon protein (e.g., Gal4 DNA binding domain), is immobilized by covalent linkage to a chromatography resin to enrich for reactive phage by affinity chromatography) and/or labeled for screen plaques or colony lifts. This procedure is called biopanning. Finally, amplified phages can be sequenced for deduction of the specific antibody sequences.

In addition, techniques developed for the production of "chimeric antibodies" or "humanized antibodies" may be utilized to modify mouse monoclonal antibodies to reduce immunogenicity of non-human antibodies. Morrison et al. (1984) Proc. Natl. Acad. Sci. 81:6851–6855; Neuberger et al. (1984) Nature, 312:604–608; Takeda et al. (1985) Nature, 314:452–454. Such antibodies are generated by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird (1988) Science 242:423–426; Huston et al. (1988) Proc. Natl. Acad. Sci. USA 85:5879–5883; and Ward et al. (1989) Nature 334:544–546) can be adapted to produce differentially expressed or pathway gene-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al. (1989) Science 246:1275–1281) to allow rapid and easy identification of monoclonal Fab fragments with the desired specificity.

By using the inventive method for screening a fully human antibody library in a yeast two-hybrid system, three monoclonal scFv antibodies were selected. FIG. 7 shows a homology alignment of the amino acid sequences of the three scFv antibodies. As shown in FIG. 7, other than the framework regions, there is also substantial homology between the three scFv antibodies in heavy chain CDR2 (in sequence GSTX$_1$YNPSL [SEQ ID NO: 32], X$_1$=N or T) and light chain CDR2 (DAX$_2$ X$_3$L [SEQ ID NO: 33], X$_2$=T or S, and X$_3$=T or D) regions. Thus, mutants of the three antibodies may be generated while conserving the consensus sequences in the heavy and/or light chain CDR2 regions.

In one embodiment, an antibody is provided that binds to loop 6 of human CCR5. In a variation, the antibody is capable of inhibiting HIV-1 infection of human cells.

Optionally, CDR2 of the heavy chain variable region of the antibody comprises amino acid sequence GSTX$_1$YNPSL [SEQ ID NO: 32], wherein X$_1$ is asparagine (N) or threonine (T).

Optionally, CDR2 of the light chain variable region comprises amino acid sequence DAX$_2$ X$_3$L [SEQ ID NO: 33], wherein X$_2$ is threonine (T) or serine (S), and X$_3$ is threonine (T) or aspartic acid (D). Optionally, CDR2 of the heavy chain variable region of the antibody comprises amino acid sequence GSTX$_1$YNPSL [SEQ ID NO: 32]; and CDR2 of the light chain variable region comprises amino acid sequence DAX$_2$ X$_3$L [SEQ ID NO: 33], wherein X$_1$ is asparagine (N) or threonine (T), X$_2$ is threonine (T) or serine (S), and X$_3$ is threonine (T) or aspartic acid (D).

Optionally, CDR3 of the heavy chain variable region of the monoclonal antibody comprises 5, 6, 7, 8, 9 or more consecutive amino acids of a sequence elected from the group consisting of

| | |
|---|---|
| RLKGAWLLSEPPYFSSDGMDV, | [SEQ ID NO: 43] |
| RTVAGTSDY, and | [SEQ ID NO: 44] |
| HEQYYYDTSGQPYYFDF. | [SEQ ID NO: 45] |

Optionally, CDR3 of the light chain variable region of the monoclonal antibody comprises 5, 6, 7, 8, 9 or more consecutive amino acids of a sequence elected from the group consisting of

| | |
|---|---|
| AAWDESLNGVV, | [SEQ ID NO: 46] |
| LQHDNFPLT, and | [SEQ ID NO: 47] |
| QQSDYLPLT. | [SEQ ID NO: 48] |

Optionally, CDR3 of the heavy chain variable region of the monoclonal antibody comprises an amino acid sequence selected from the group consisting of SEQ ID Nos: 43–45; and CDR3 of the light chain variable region of the monoclonal antibody comprises an amino acid sequence selected from the group consisting of SEQ ID Nos: 46–48.

It is noted that the above-described different CDR regions may all be included in the antibody independent of each other, or in combination with one or more of each other.

Optionally, the heavy chain variable region of the monoclonal antibody comprises an amino acid sequence selected from SEQ ID Nos: 36, 38, and 40 (shown in FIG. 8).

Optionally, the light chain variable region of the monoclonal antibody comprises an amino acid sequence selected from SEQ ID Nos: 37, 39, and 41 (shown in FIG. 8).

It should be appreciated that the present invention also provides for analogs of antibodies against CCR5 Loop 6 obtained according to the methods described above. Analogs may differ from naturally occurring proteins by conservative amino acid sequence differences or by modifications which do not affect sequence, or by both.

For example, conservative amino acid changes may be made, which although they alter the primary sequence of the peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications of the antibodies include in vivo, or in vitro chemical derivatization of proteins, e.g., acetylation, or carboxylation. Also included are modifications of glycosylation, e.g., those made by modifying the glycosylation patterns of a protein during its synthesis and processing or in further processing steps; e.g., by exposing the protein to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are antibodies which have been modified using ordinary molecular biological techniques so as to improve their resistance to proteolytic degradation or to optimize solubility properties. Analogs of such proteins include those containing residues other than naturally occurring L-amino acids, e.g., D-amino acids or non-naturally occurring synthetic amino acids. The proteins of the invention are not limited to products of any of the specific exemplary processes listed herein.

3. Use of Antibody Against HIV Coreceptors for Prevention and Treatment of HIV Infection The antibodies of the present invention selected against target peptides derived from HIV coreceptors may be used for prevention and treatment of HIV infection in vitro and in vivo.

To inhibit infection of cells by HIV in vitro, cells are treated with the antibody of the invention, or a derivative thereof, either prior to or concurrently with the addition of virus. Inhibition of infection of the cells by the antibody of the present invention is assessed by measuring the replication of virus in the cells, by identifying the presence of viral nucleic acids and/or proteins in the cells, for example, by performing PCR, Southern, Northern or Western blotting analyses, reverse transcriptase (RT) assays, or by immunofluorescence or other viral protein detection procedures. The amount of antibody and virus to be added to the cells will be apparent to one skilled in the art from the teaching provided herein.

To prevent or inhibit infection of cells by HIV in vivo, the antibody of the present invention, or a derivative thereof, is administered to a human subject who is either at risk of acquiring HIV infection, or who is already infected with HIV.

The antibody of the present invention may be formulated for delivery via various routes of administration, including but not limited to, orally, parenterally, intraperitoneally, intravenously, intraarterially, topically, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally.

In an embodiment, the antibody is in an injectable formulation. The formulation is suitable for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulatory agents such as suspending, stabilizing and/or dispersing agents.

Prior to administration, the antibody, or a derivative thereof, is suspended in a pharmaceutically acceptable formulation such as a saline solution or other physiologically acceptable solution which is suitable for the chosen route of administration and which will be readily apparent to those skilled in the art of antibody preparation and administration. The dose of antibody to be used may vary dependent upon any number of factors including the age of the individual, the route of administration and the extent of HIV infection in the individual. The antibody is prepared for administration by being suspended or dissolved in a pharmaceutically acceptable carrier such as saline, salt solution or other formulations apparent to those skilled in such administration.

Typically, the antibody is administered in a range of 0.1 µg to 1 g of protein per dose. Approximately 1–10 doses are administered to the individual at intervals ranging from once per day to once every few years.

The antibody may optionally be administered orally to a human. For example, the antibody of the present invention would be formulated in propylene glycol solution by attaching the antibody a polymer carrier. Polymers or liposomes can stabilize the protein and desensitize it to digestive enzymes by encapsulating the protein within.

Also optionally, the antibody may be formulated for pulmonary delivery via inhalation. For example, the antibody could be delivered as aerosolized powder to a host using an inhaler. The lung provides an excellent site for delivery of protein or peptide drug because the drugs are absorbed quickly into the blood-stream due to the huge surface area of the lung. In addition, the layer separating airflow from blood vessels is very narrow, so that the drug does not have far to travel to enter blood.

Also optionally, the antibody of the invention may be administered to a host in a sustained release formulation using a biodegradable biocompatible polymer, or by on-site delivery using micelles, gels and liposomes, or rectally (e.g., by suppository or enema). For example, the antibody is formulated with a polymer such as pluronic F127. The gel formulation may be injected subcutaneously or intramuscularly to allow the antibody to be bled out over a period of time to ensure efficacy.

Also optionally, the antibody of the invention may be administered to a host in a topical formulation. The antibody may be formulated with suitable pharmaceutically acceptable carrier that does not denature or inactivate the protein in the form of lotion, cream, gel or suppository. For example, the anti-human CCR5 antibody of the present invention may be used as prophylactic or therapeutic to prevent or treat infection of HIV (or other sexually transmitted diseases or STD) via skin or mucosa of the body. The topical formulation of the antibody may be applied to all areas of skin likely to come in intimate contact during sexual activity, especially to any area that has sores or breaks in the skin. For example, cream or lotion containing the antibody may be applied to the surfaces of the penis, the base of the penis and scrotum, the upper vagina, the inner and outer lips of the vulva, the inner thighs, pubic and perianal regions. The antibody may also be applied to the anus and/or delivered directly to the rectum via the penis. In addition, the antibody may be incorporated into an intrauterine device or an intravaginal device that timely releases the antibody into the uterus or into the vagina to provide continuous protection against infection of viruses. For example, the antibody may be formulated as co-polymer with ethylene-vinyl acetate which forms a soft, rubber-like material. The procedures for forming an antibody co-polymer with ethylene-vinyl acetate are described in U.S. Pat. No. 4,391,797 which is incorporated herein by reference in its entirety.

Applying the antibody to the skin and mucosa of the body is advantageous in that the surfaces of skin and mucus epithelia that are exposed to semen and other body fluids during sexual activity are most at risk of exposure to HIV or other STD pathogens. It is believed that the major roles of secreted antibodies are to block the adhesive groups that enable a pathogen to adhere to its target cell. The antibody of the present invention can be used to block the adhesion of HIV to its target cells such as $CD4^+$ cells by binding to HIV coreceptor such as CCR5 and CXCR4. With the occupation of the antibody on the coreceptors on the host's cells, HIV carried by body fluid such as semen and blood of another individual can be prevented from entry into the host's cells, thus significantly reducing the risk of infection.

The antibody of the present invention may be used in combination with a variety of anti-retroviral drugs for prevention or treatment of HIV infection. Anti-retroviral drugs include many small molecule drugs (e.g. organic compounds) and macromolecule drugs (antisense DNAs/RNAs, ribozymes, viral surface protein-binding proteins or nucleotides, etc.).

Anti-retroviral drugs against HIV have been developed since the discovery of correlation between HIV and AIDS. In particular, many anti-retroviral drugs have been developed to target critical enzymes of retroviruses and inhibit replication of the virus inside the host cell. For example, nucleoside or nucleotide analogs such as AZT, dideoxycytidine (ddC), and dideoxyinosine (ddI) were developed to inhibit reverse transcriptase (RT) of retroviruses by acting as competitive inhibitors and chain terminators. Non-nucleoside or nucleotide inhibitors have also been found to inhibit reverse transcriptase activity of retroviruses by exerting an allosteric effect by binding to a hydrophobic pocket close to the active site of RT. The protease (PRO) inhibitors in current use are targeted at the active site of the enzyme.

In addition to the RT and PRO inhibitors of HIV infection, other classes of antiviral agents targeting different components of HIV or interfering with different stages of HIV life cycle may be also be used in conjunction with the antibody to achieve efficacious clinical results. For example, synthetic peptides have been modeled to mimic the coiled-coiled helical bundle formed by heptad repeat sequences of one of the two subunits of HIV envelop glycoprotein, the transmembrane glycoprotein (gp41). Wild C. T. et al. "A synthetic peptide inhibitor of HIV replication: correlation between solution structure and viral inhibition" Proc. Natl. Acad. Sci. USA 89: 10537–10541 (1992). These heptad sequences play important roles in the conformational changes essential for membrane fusion of HIV with host cells. The synthetic peptides, DP107 and DP178, have been shown to inhibit infection in vitro by disrupting the gp41 conformational changes associated with membrane fusion. Wild, C. et al. "Peptides corresponding to a predictive alpha-helical domain of HIV-1 gp41 are potent inhibitors of virus infection" Proc. Natl. Acad. Sci. USA 91: 9770–9774 (1994). In particular, a 36-amino acid peptide (T-20), corresponding to DP178, functions as a potent inhibitor of the HIV-1 envelop-cell membrane fusion and viral entry. Wild, C. et al. "A synthetic peptide from HIV-1 gp41 is a potent inhibitor of virus-mediated cell-cell fusion" AIDS Res. Hum. Retroviruses 9:1051–1053 (1993). When used in monotherapy, T-20 demonstrated potent antiviral activity in vivo when administered as an intravenous subcutaneous infusion in trials of 28 days or less. Lalezari, J. et al "Safety, pharmacokinetics, and antiviral activity of T-20 as a single agent in heavily pretreated patients" 6$^{th}$ Conference on Retroviruses and Opportunistic Infections, Chicago, February 1999 [Abstract LB13]. Such inhibitors of HIV fusion and entry into the host cells may be combined with the antibodies of the present invention, as well as other anti-retroviral agents to inhibit HIV infection at different stages of the retroviral life cycle.

Further, inhibitors of retroviral integrase may be used in conjunction with in combination with the antibodies of the present invention according to the present invention. A variety of inhibitors of HIV integrase have been identified that inhibit HIV integration at different stages. In general, retroviral integration occurs in the following three biochemical stages: 1) assembly of a stable complex with specific DNA sequences at the end of the HIV-1 long terminal repeat (LTR) regions, (2) endonucleolytic processing of the viral DNA to remove the terminal dinucleotide from each 3' end, and (3) strand transfer in which the viral DNA 3' ends are covalently linked to the cellular (target) DNA. Pommier, Y. and Neamati, N. in Advances in Viral Research, K. Maramorosch, et al. eds. Academic Press, New York (1999), pp 427–458. Compounds have been identified to interfere with assembly of the stable complex in assays with purified, recombinant integrase. Hazuda, D. J. et al. Drug Des. Discovery 15: 17 (1997). In a random screening of more than 250,000 samples. A variety of compounds have been discovered as inhibitors of strand transfer reaction catalyzed by integrase. Hazuda, D. J. et al. "Inhibitors of strand transfer that prevent integration and inhibit HIV-1 replication in cells" Science 287:646–650 (2000). The most potent and specific compounds each contained a distinct diketo acid moiety, such as compound L-731,988, L-708,906, L-731,927, and L-731,942. Hazuda, D. J. et al. (2000), supra. Such inhibitors of HIV integration into the host genome may be combined with in combination with the antibodies of the present invention, as well as other anti-retroviral agents to inhibit HIV infection at different stages of the retroviral life cycle.

In the pharmaceutical compositions of the present invention, nucleoside reverse transcriptase inhibitors, non-nucleoside reverse transcriptase inhibitors, protease inhibitors, fusion inhibitors and integrase inhibitors are the preferred anti-retroviral drugs in combination with the antibody. Examples of the nucleoside HIV reverse transcriptase inhibitor include, but are not limited to zidovudine (AZT), didanosine (ddI), zalcitabine (ddC), lamivudine (3TC), stavudine (d4T), abacavir (1592U89), and adefovir dipivoxil (bis(POM)-PMEA). Examples of the non-nucleoside HIV reverse transcriptase inhibitor include, but are not limited to nevirapine (BI-RG-587), delavirdine (BHAP, U-90152) and efavirenz (DMP 266). Examples of the HIV protease inhibitors include, but are not limited to indinavir (MK-639), ritonavir (ABT-538), saqinavir (Ro-31-8959), nelfinavir (AG-1343), and amprenavir (141W94).

The antibody of the present invention may be used in combination with any one or more of the antiretroviral drugs, preferably with a "cocktail" of nucleoside reverse transcriptase inhibitors, non-nucleoside HIV reverse transcriptase inhibitors, and protease inhibitors. For example, the antibody of the present invention may be combined with two nucleoside reverse transcriptase inhibitors (e.g. zidovudine (AZT) and lamivudine (3TC)), and one protease inhibitor (e.g. indinavir (MK-639)). The antibody of the present invention may also be combined with one nucleoside reverse transcriptase inhibitor (e.g. stavudine (d4T)), one non-nucleoside reverse transcriptase inhibitor (e.g. nevirapine (BI-RG-587)), and one protease inhibitor (e.g. nelfinavir (AG-1343)). Alternatively, the antibody of the present invention may be combined with one nucleoside reverse transcriptase inhibitor (e.g. zidovudine (AZT)), and two protease inhibitors (e.g. nelfinavir (AG-1343) and saqinavir (Ro-31-8959)).

Optionally, the pharmaceutical composition of the present invention further includes one or more general antiviral agents. Examples of general antiviral agents include, but are not limited to acyclovir, ganciclovir, trisodium phosphonoformate, novapren (Novaferon Labs, Inc., Akron, Ohio), Peptide T Octapeptide Sequence (Peninsula Labs, Belmont, Calif.), ansamycin LM 427 (Adria Labortories, Dublin, Ohio), dextran sulfate, virazole, ribavirin (Virateck/ICN, Costa Mesa, Calif.), α-interferon, and β-interferon. General antiviral agents can be used to prevent or inhibit opportunistic infections of other viruses.

4. Use of Antibody Against HIV Coreceptors for Screening Anti-HIV Agents

The antibody of the present invention may also be used in a method of screening agents for anti-HIV activity. A test agent (e.g., a compound) is first screened for the ability to bind to the antibody of the invention. Compounds which bind to the antibody are likely to share structural and perhaps biological activities with the HIV coreceptor (e.g., CCR5) and thus, may serve as competitive inhibitors for inhibition of the interaction of HIV envelope protein with CD4 and/or CCR5 plus CD4. An antibody-binding compound is further tested for antiviral activity by treating cells with the compound either prior to or concurrently with the addition of virus to the cells. Alternatively, the virus and the compound may be mixed together prior to the addition of the mixture to the cells. The ability of the compound to affect virus infection is assessed by measuring virus replication in the cells using any one of the known techniques, such as a RT assay, immunofluorescence assays and other assays known in the art useful for detection of viral proteins or nucleic acids in cells. Generation of newly replicated virus may also be measured using known virus assays such as those which are described herein.

The antibody of the present invention may also be used in competition assays to screen for compounds that bind to the HIV coreceptor (e.g., CCR5) and which therefore prevent binding of the antibody to the coreceptor. Such compounds, once identified, may be examined further to determine whether or not they prevent entry of virus into cells. Compounds which prevent entry of virus into cells are useful as anti-viral compounds.

Additional uses for the antibody of the present invention include the identification of cells in the body which are potential targets for infection by HIV. These cells express HIV coreceptor(s) and are therefore capable of being infected by HIV. For example, cells which are potential targets for HIV infection may be identified by virtue of the presence of CCR5 on their surface. The antibody of the present invention facilitates identification of these cells as follows.

The antibody of the present invention is first combined with an identifiable marker, such as an immunofluorescent or radioactive marker. Cells which are obtained from a human subject are then reacted with the tagged antibody. Binding of the antibody to cells is an indication that such cells are potential targets for HIV infection. The identification of cells which may be infected with HIV is important for the design of therapies for the prevention of HIV infection. In the case of individuals who are infected with HIV, the identification of target cells provides an immune profile of these individuals which provides useful information regarding the progress of their infection.

In addition to the aforementioned uses for the monoclonal antibody of the present invention, the antibody may be useful for the detection of CCR5 on a variety of cell types on which CCR5 may be expressed.

The monoclonal antibody of the present invention may be useful for monitoring CCR5 expression levels on a variety of cell types, which expression may be an indication of a disease state in a human, including, but not limited to HIV infection, atherosclerosis, and the like.

5. Construction of scFv Library Via Homologous Recombination in Yeast

The library of scFv proteins may be produced in vivo or in vitro by using any methods known in the art. In a preferred embodiment, the library of scFv proteins is constructed in yeast by exploiting the intrinsic property of yeast—homologous recombination at an extremely high level of efficiency.

Figure 3:
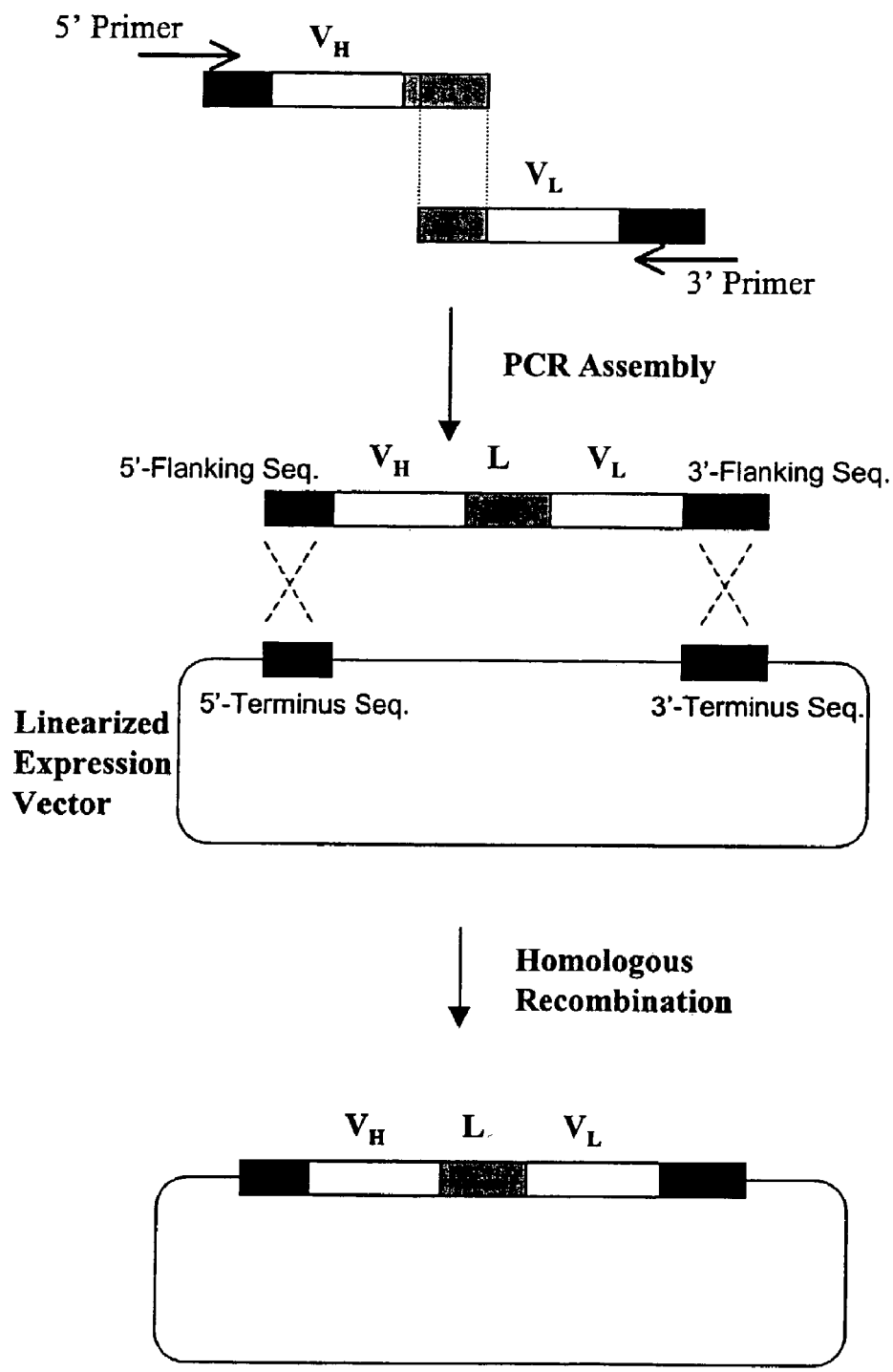
FIG. 3 illustrates a method of constructing a human scFv antibody library via homologous recombination in yeast.

FIG. 3 shows a flow chart delineating a method for generating and screening highly diverse libraries of single-chain human antibodies (scFv) in yeast. As illustrated in FIG. 3, a highly complex library of scFv is constructed in yeast cells. In particular, cDNA libraries of the heavy and light chain variable regions ($V_H$ and $V_L$) are transferred into a yeast expression vector by direct homologous recombination between the sequences encoding $V_H$ and $V_L$, and the yeast expression vector containing homologous recombination sites. The resulting expression vector is called scFv expression vector. This primary antibody library may reach a diversity preferably between $10^6$–$10^{12}$, more preferably between $10^7$–$10^{12}$, and most preferably between $10^8$–$10^{12}$.

The diversity of $V_H$ and $V_L$ within the library of scFv fusion proteins may be preferably between $10^3$–$10^8$, more preferably between $10^4$–$10^8$, and most preferably between $10^5$–$10^8$.

Optionally, AD is an activation domain of yeast GAL 4 transcription activator; and BD is a DNA binding domain of yeast GAL 4 transcription activator.

The linker sequence L may have a specific sequence, or vary within the library of the yeast expression vectors.

The linker sequences L in the library of expression vectors is preferably between 30–120 bp in length, more preferably between 45–102 bp in length, and most preferably between 45–63 bp in length. The linker sequence in the library of expression vectors preferably comprises a nucleotide sequence encoding an amino acid sequence of Gly-Gly-Gly-Gly-Ser in 3 or 4 tandem repeats.

The linker peptides expressed by the library of expression vectors preferably provide a substantially conserved conformation between the first and second polypeptide subunits across the fusion proteins expressed by the library of expression vectors. For example, a linker peptide Gly-Gly-Gly-Gly-Ser [SEQ ID NO: 42] in 4 tandem repeats ($G_4S$)$_4$ [SEQ ID NO: 4] is believed to provide a substantially conserved conformation of scFv antibodies which preserves its antigen-binding site in the variable regions of the corresponding full antibody.

DNA sequences encoding human antibody $V_H$ and $V_L$ segments may be polynucleotide segments of at least 30 contiguous base pairs substantially encoding genes of the immunoglobulin superfamily. A. F. Williams and A. N. Barclay (1989) "The Immunoglobulin Gene Superfamily", in Immunoglobulin Genes, T. Honjo, F. W. Alt, and T. H. Rabbitts, eds., Academic Press: San Diego, Calif., pp. 361–387. The $V_H$ and $V_L$ genes are most frequently encoded by human, non-human primate, avian, porcine, bovine, ovine, goat, or rodent heavy chain and light chain gene sequences.

The library of DNA sequences encoding human antibody $V_H$ and $V_L$ segments may be derived from a variety of sources. For example, mRNA encoding the human antibody $V_H$ and $V_L$ libraries may be extracted from cells or organs from immunized or non-immunized animals or humans. Preferably, organs such as human fetal spleen and lymph nodes may be used. Peripheral blood cells from non-immunized humans may also be used. The blood samples may be from an individual donor, from multiple donors, or from combined blood sources.

The human antibody $V_H$- and $V_L$-coding sequences may be derived and amplified by using sets of oligonucleotide primers to amplify the cDNA of human heavy and light chains variable domains by polymerase chain reaction (PCR). Orlandi et al. (1989) Proc. Natl. Acad. Sci. USA 86: 3833–3837. For example, blood sample may be from healthy volunteers and B-lymphocyte in the blood can be isolated. RNA can be prepared by following standard procedures. Cathala et al. (1983) DNA 3:329. The cDNA can be made from the isolated RNA by using reverse transcriptase.

Alternatively, the $V_H$- and $V_L$-coding sequences may be derived from an artificially rearranged immunoglobulin gene or genes. For example, immunoglobulin genes may be rearranged by joining of germ line V segments in vitro to J segments, and, in the case of $V_H$ domains, D segments. The joining of the V, J and D segments may be facilitated by using PCR primers which have a region of random or specific sequence to introduce artificial sequence or diversity into the products.

The fusion protein formed by linking $V_H$ and $V_L$ polypeptides is also referred as a single-chain antibody, scFv. A typical scFv comprises a $V_H$ domain and a $V_L$ domain in polypeptide linkage, generally linked via a spacer/linker peptide L. The linker peptide sequence L may encode an appropriately designed linker peptide, such as (Gly-Gly-Gly-Gly-Ser)$_4$ [SEQ. ID NO: 4] or equivalent linker peptide(s). The linker bridges the C-terminus of the first V region and N-terminus of the second, ordered as either $V_H$-L-$V_L$ or $V_L$-L-$V_H$.

A scFv may comprise additional amino acid sequences at the amino- and/or carboxy-termini. For example, a single-chain antibody may comprise a tether segment for linking to the constant regions of a complete or full antibody. A functional single-chain antibody generally contains a sufficient portion of an immunoglobulin superfamily gene product so as to retain the property of binding to a specific target molecule, typically a receptor or antigen (epitope).

In a preferred embodiment, the expression vector is based on a yeast plasmid, especially one from *Saccharomyces cerevisiae*. After transformation of yeast cells, the exogenous DNA encoding scFv fusion proteins are uptaken by the cells and subsequently expressed by the transformed cells.

More preferably, the expression vector may be a yeast-bacteria shuttle vector which can be propagated in either *Escherichia coli* or yeast Struhl, et al. (1979) Proc. Natl. Acad. Sci. 76:1035–1039. The inclusion of *E. coli* plasmid DNA sequences, such as pBR322, facilitates the quantitative preparation of vector DNA in *E. coli*, and thus the efficient transformation of yeast.

The types of yeast plasmid vector that may serve as the shuttle may be a replicating vector or an integrating vector. A replicating vector is yeast vector that is capable of mediating its own maintenance, independent of the chromosomal DNA of yeast, by virtue of the presence of a functional origin of DNA replication. An integrating vector relies upon recombination with the chromosomal DNA to facilitate replication and thus the continued maintenance of the recombinant DNA in the host cell. A replicating vector may be a 2µ-based plasmid vector in which the origin of DNA replication is derived from the endogenous 2µ plasmid of yeast. Alternatively, the replicating vector may be an autonomously replicating (ARS) vector, in which the "apparent" origin of replication is derived from the chromosomal DNA of yeast. Optionally, the replicating vector may be a centromeric (CEN) plasmid which carries in addition to one of the above origins of DNA replication a sequence of yeast chromosomal DNA known to harbor a centromere.

The vectors may be transformed into yeast cells in a closed circular form or in a linear form. Transformation of yeast by integrating vectors, although with inheritable stability, may not be efficient when the vector is in in a close circular form (e.g. 1–10 transformants per ug of DNA). Linearized vectors, with free ends located in DNA sequences homologous with yeast chromosomal DNA, transforms yeast with higher efficiency (100–1000 fold) and the transforming DNA is generally found integrated in sequences homologous to the site of cleavage. Thus, by cleaving the vector DNA with a suitable restriction endonuclease, it is possible to increase the efficiency of transformation and target the site of chromosomal integration. Integrative transformation may be applicable to the genetic modification of brewing yeast, providing that the efficiency of transformation is sufficiently high and the target DNA sequence for integration is within a region that does not disrupt genes essential to the metabolism of the host cell.

ARS plasmids, which have a high copy number (approximately 20–50 copies per cell) (Hyman et al., 1982), tend to be the most unstable, and are lost at a frequency greater than 10% per generation. However, the stability of ARS plasmids can be enhanced by the attachment of a centromere; centromeric plasmids are present at 1 or 2 copies per cell and are lost at only approximately 1% per generation.

The expression vector of the present invention is preferably based on the 2µ plasmid. The 2µ plasmid is known to be nuclear in cellular location, but is inherited in a non-Mendelian fashion. Cells that lost the 2µ plasmid have been shown to arise from haploid yeast populations having an average copy number of 50 copies of the 2µ plasmid per cell at a rate of between 0.001% and 0.01% of the cells per generation. Futcher & Cox (1983) J. Bacteriol. 154:612. Analysis of different strains of *S. cerevisiae* has shown that the plasmid is present in most strains of yeast including brewing yeast. The 2µ plasmid is ubiquitous and possesses a high degree of inheritable stability in nature.

The 2µ plasmid harbors a unique bidirectional origin of DNA replication which is an essential component of all 2µ-based vectors. The plasmid contains four genes, REP1, REP2, REP3 and FLP which are required for the stable maintenance of high plasmid copy number per cell Jaysram et al. (1983) Cell 34:95. The REP1 and REP2 genes encode trans-acting proteins which are believed to function in concert by interacting with the REP3 locus to ensure the stable partitioning of the plasmid at cell division. In this respect, the REP3 gene behaves as a cis acting locus which effects the stable segregation of the plasmid, and is phenotypically analogous to a chromosomal centromere. An important feature of the 2µ plasmid is the presence of two inverted DNA sequence repeats (each 559 base-pairs in length) which separate the circular molecule into two unique regions. Intramolecular recombination between the inverted repeat sequences results in the inversion of one unique region relative to the other and the production in vivo of a mixed population of two structural isomers of the plasmid, designated A and B. Recombination between the two inverted repeats is mediated by the protein product of a gene called the FLP gene, and the FLP protein is capable of mediating high frequency recombination within the inverted repeat region. This site specific recombination event is believed to provide a mechanism which ensures the amplification of plasmid copy number. Murray et al. (1987) EMBO J. 6:4205.

The expression vector may also contain an *Escherichia coli* origin of replication and *E. coli* antibiotic resistance genes for propagation and antibiotic selection in bacteria. Many *E. coli* origins are known, including ColE1, pMB1 and pBR322, The ColE origin of replication is preferably used in this invention. Many *E. coli* drug resistance genes are known, including the ampicillin resistance gene, the chloramphenoicol resistance gene and the tetracycline resistance gene. In one particular embodiment, the ampicillin resistance gene is used in the vector.

The transformants that carry the scFv library may be selected by using various selection schemes. The selection is typically achieved by incorporating within the vector DNA a gene with a discernible phenotype. In the case of vectors used to transform laboratory yeast, prototrophic genes, such as LEU2, URA3 or TRP1, are usually used to complement auxotrophic lesions in the host. However, in order to transform brewing yeast and other industrial yeasts, which are frequently polyploid and do not display auxotrophic requirements, it is necessary to utilize a selection system based upon a dominant selectable gene. In this respect replicating transformants carrying 2μ-based plasmid vectors may be selected based on expression of marker genes which mediate resistance to: antibiotics such as G418, hygromycin B and chloramphenicol, or otherwise toxic materials such as the herbicide sulfometuron methyl, compactin and copper.

6. Screening of scFv Library Against the Target Peptide in Yeast Two-Hybrid System The present invention provides efficient methods for screening the scFv library against any target peptide in a yeast two-hybrid system.

The two-hybrid system is a selection scheme designed to screen for polypeptide sequences which bind to a predetermined polypeptide sequence present in a fusion protein. Chien et al. (1991) Proc. Natl. Acad. Sci. (USA) 88: 9578). This approach identifies protein-protein interactions in vivo through reconstitution of a transcriptional activator. Fields and Song (1989) Nature 340: 245), the yeast Gal 4 transcription protein. The method is based on the properties of the yeast Gal 4 protein, which consists of separable domains responsible for DNA-binding and transcriptional activation. Polynucleotides encoding two hybrid proteins, one consisting of the yeast Gal 4 DNA-binding domain (BD) fused to a polypeptide sequence of a known protein and the other consisting of the Gal4 activation domain (AD) fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site.

Typically, the two-hybrid method is used to identify novel polypeptide sequences which interact with a known protein. Silver and Hunt (1993) Mol. Biol. Rep. 17: 155; Durfee et al. (1993) Genes Devel. 7; 555; Yang et al. (1992) Science 257: 680; Luban et al. (1993) Cell 73: 1067; Hardy et al. (1992) Genes Devel. 6; 801; Bartel et al. (1993) Biotechniques 14: 920; and Vojtek et al. (1993) Cell 74: 205. The two-hybrid system was used to detect interactions between three specific single-chain variable fragments (scFv) and a specific antigen. De Jaeger et al. (2000) FEBS Lett. 467: 316–320. The two-hybrid system was also used to screen against cell surface proteins or receptors such as receptors of hematopoietic super family in yeast. Ozenberger, B. A., and Young, K. H. (1995) "Functional interaction of ligands and receptors of hematopoietic superfamily in yeast" Mol Endocrinol. 9:1321–1329.

Variations of the two-hybrid method have been used to identify mutations of a known protein that affect its binding to a second known protein Li and Fields (1993) FASEB J. 7: 957; Lalo et al. (1993) Proc. Natl. Acad. Sci. (USA) 90: 5524; Jackson et al. (1993) Mol. Cell. Biol. 13; 2899; and Madura et al. (1993) J. Biol. Chem. 268: 12046.

Two-hybrid systems have also been used to identify interacting structural domains of two known proteins or domains responsible for oligomerization of a single protein. Bardwell et al. (1993) Med. Microbiol. 8: 1177; Chakraborty et al. (1992) J. Biol. Chem. 267: 17498; Staudinger et al. (1993) J. Biol. Chem. 268: 4608; and Milne G T; Weaver D T (1993) Genes Devel. 7; 1755; Iwabuchi et al. (1993) Oncogene 8; 1693; Bogerd et al. (1993) J. Virol. 67: 5030).

Variations of two-hybrid systems have been used to study the in vivo activity of a proteolytic enzyme. Dasmahapatra et al. (1992) Proc. Natl. Acad. Sci. (USA) 89: 4159. Alternatively, an *E. coli*/BCCP interactive screening system was used to identify interacting protein sequences (i.e., protein sequences which heterodimerize or form higher order heteromultimers). Germino et al. (1993) Proc. Natl. Acad. Sci. (U.S.A.) 90: 933; and Guarente L (1993) Proc. Natl. Acad. Sci. (U.S.A.) 90: 1639.

Typically, selection of binding protein using a two-hybrid method relies upon a positive association between two Gal4 fusion proteins, thereby reconstituting a functional Gal4 transcriptional activator which then induces transcription of a reporter gene operably linked to a Gal4 binding site. Transcription of the reporter gene produces a positive readout, typically manifested either (1) as an enzyme activity (e.g., β-galactosidase) that can be identified by a colorimetric enzyme assay or (2) as enhanced cell growth on a defined medium (e.g., HIS3 and Ade 2). Thus, the method is suited for identifying a positive interaction of polypeptide sequences, such as antibody-antigen interactions.

False positives clones that indicate activation of the reporter gene irrespective of the specific interaction between the two hybrid proteins, may arise in the two-hybrid screening. Various procedures have developed to reduce and eliminate the false positive clones from the final positives. For example, 1) prescreening the clones that contains the target vector and shows positive in the absence of the two-hybrid partner (Bartel, P. L., et al. (1993) "Elimination of false positives that arise in using the two-hybrid system" BioTechniques 14:920–924); 2) by using multiple reporters such as His3, β-galactosidase, and Ade2 (James, P. et al. (1996) "Genomic libraries and a host strain designed for highly efficient two-hybrid selection in yeast" Genetics 144:1425–1436); 3) by using multiple reporters each of which is under different GAL 4-responsive promoters such as those in yeast strain Y190 where each of the His 3 and β-Gal reporters is under the control of a different promoter Gal 1 or Gal 10, but both response to Gal 4 signaling (Durfee, T., et al (1993) "The retinoblastoma protein associates with the protein phosphatase type 1 catalytic subunit" Genes Devel. 7:555–569); and 4) by post-screening assays such as testing isolates with target consisting of GAL 4-BD alone.

In addition, the false positive clones may also be eliminated by using unrelated targets to confirm specificity. This is a standard control procedure in the two-hybrid system which can be performed after the library isolate is confirmed by the above-described 1)–4) procedures. Typically, the library clones are confirmed by co-transforming the initially isolated library clones back into the yeast reporter strain with one or more control targets unrelated to the target used in the original screening. Selection is conducted to eliminate those library clones that show positive activation of the reporter gene and thus indicate non-specfic interactions with multiple, related proteins.

When the library of scFv fusion proteins are expressed by the expression vector in yeast cells, such as cells from the *Saccharomyces cerevisiae* strains, the scFv fusion protein undergoes a process of protein folding to adopt one or more conformations. The peptide sequence encoded by the linker sequence L also facilitates the folding by providing a flexible hinge between the $V_H$ and $V_L$. The conformation(s) adopted by the scFv fusion protein may have suitable binding site(s) for a specific target peptide expressed as fusion protein with the domain BD of a transcription activator. The AD domain of the scFv fusion protein should be able to activate transcription of gene(s) once the AD and BD domains are reconstituted to form an active transcription activator in vitro or in vivo by a two-hybrid method.

In a preferred embodiment, the highly complex primary antibody libraries is screened against the peptide target, for example a 30 aa peptide derived from loop 6 of CCR5. This screening for antibody-antigen interaction is conveniently carried out in yeast by using a yeast two-hybrid method. The library of scFv expression vectors are introduced into yeast cells. Expression of the scFv antibody library in the yeast cells produces a library of scFv fusion proteins, each fusion protein comprising a scFv and an activation domain (AD) of a transcription activator. The yeast cells are also modified to express a recombinant fusion protein comprising a DNA-binding domain (BD) of the transcription activator and the target peptide. The yeast cells are also modified to express a reporter gene whose expression is under the control of a specific DNA binding site. Upon binding of the scFv antibody from the library to the target antigen, the AD is brought into close proximity of BD, thereby causing transcriptional activation of a reporter gene downstream from a specific DNA binding site to which the BD binds. It is noted that the library of scFv expression vectors may contain the BD domain while the modified yeast cells express a fusion protein comprising the AD domain and the target peptide.

These scFv expression vectors may be introduced to yeast cells by co-transformation of diploid yeast cells or by direct mating between two strains of haploid yeast cells. For example, the scFv expression vectors and an expression vector containing the target peptide can be used to co-transform diploid yeast cells in a form of yeast plasmid or bacteria-yeast shuttle plasmid. Alternatively, two strains haploid yeast cells (e.g. α- and a-type strains of yeast), each containing the scFv expression vector and the target peptide expression vector, respectively, are mated to produce a diploid yeast cell containing both expression vectors. Preferably, the haploid yeast strain containing the target peptide expression vector also contains the reporter gene positioned downstream of the specific DNA binding site.

The yeast clones containing scFv antibodies with binding affinity to the target peptide are selected based on phenotypes of the cells or other selectable markers. The plasmids encoding these primary antibody leads can be isolated and further characterized. The affinity and biological activity of the primary antibody leads can be determined using assays particularly designed based on the specific target protein from which the target peptide is derived.

Figure 2A:
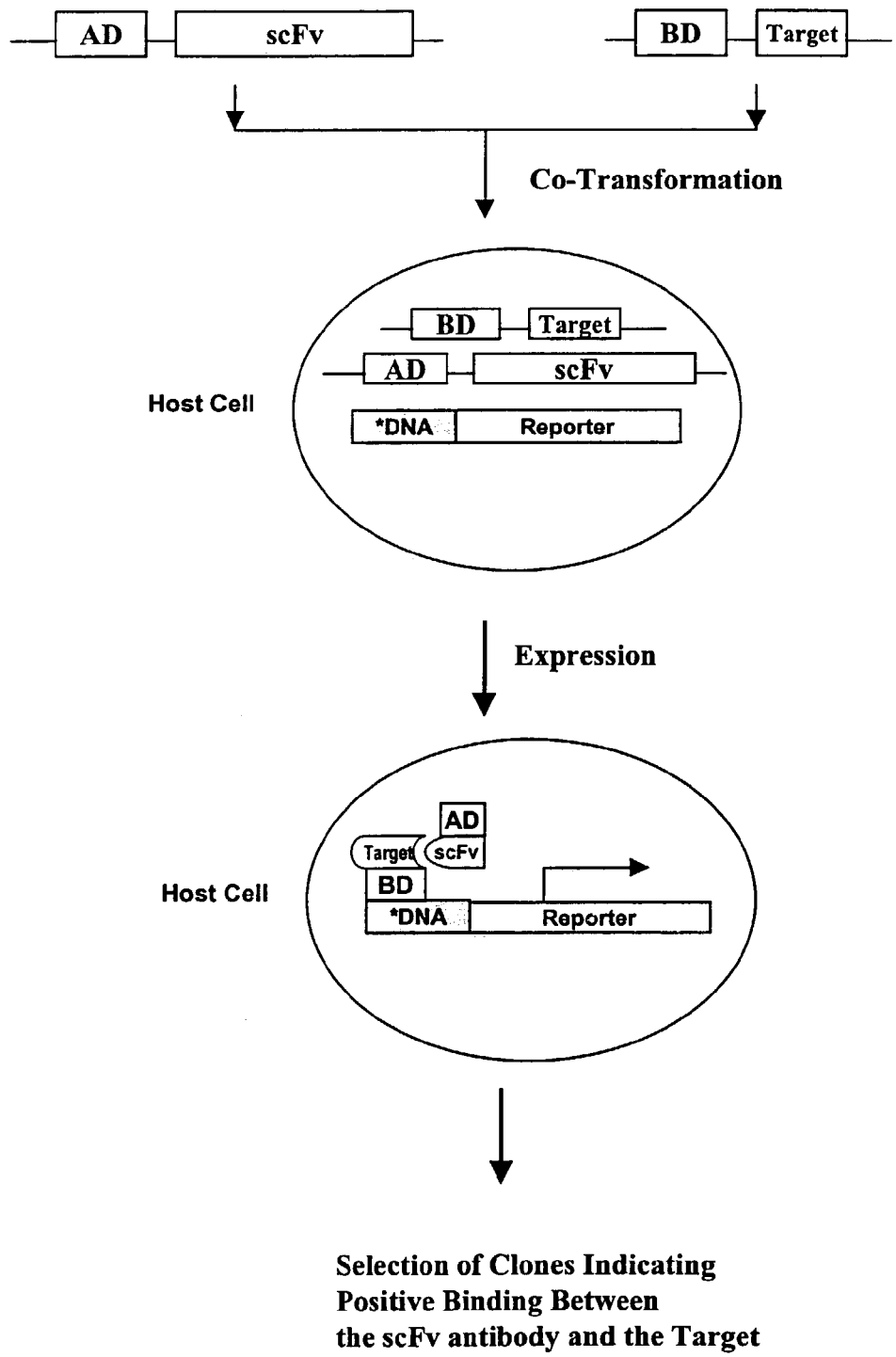
FIG. 2A illustrates an embodiment of the method of present invention for screening of scFv against a target peptide derived from a membrane protein via transformation of yeast cells.

FIG. 2A illustrates a flow diagram of a preferred embodiment of the above described method. As illustrated in FIG. 2A, the sequence library containing scFv fused with an AD domain upstream is carried by a library of expression vectors, the AD-scFv vectors. The coding sequence of the target peptide (labeled as "Target") is contained in another expression vector and fused with a BD domain, forming the BD-Target vector.

The AD-scFv vector and the BD-Target vector may be co-transformed into a yeast cell by using method known in the art. Gietz, D. et al. (1992) "Improved method for high efficiency transformation of intact yeast cells" Nucleic Acids Res. 20:1425. The construct carrying the specific DNA binding site and the reporter gene (labeled as "Reporter") may be stably integrated into the genome of the host cell or transiently transformed into the host cell. Upon expression of the sequences in the expression vectors, the library of scFv fusion proteins undergo protein folding in the host cell and adopt various conformations. Some of the scFv fusion proteins may bind to the Target protein expressed by the BD-Target vector in the host cell, thereby bringing the AD and BD domains to a close proximity in the promoter region (i.e., the specific DNA binding site) of the reporter construct and thus reconstituting a functional transcription activator composed of the AD and BD domains. As a result, the AD activates the transcription of the reporter gene downstream from the specific DNA binding site, resulting in expression of the reporter gene, such as the lacZ reporter gene. Clones showing the phenotype of the reporter gene expression are selected, and the AD-scFv vectors are isolated. The coding sequences for scFv are identified and characterized.

Alternatively, the steps of expressing the library of scFv fusion proteins and expressing the target fusion protein includes causing mating between first and second populations of haploid yeast cells of opposite mating types. The first population of haploid yeast cells comprises a library of scFv expression vectors for the library of tester fusion proteins. The second population of haploid yeast cells comprises a target expression vector. Either the first or second population of haploid yeast cells comprises a reporter construct comprising the reporter gene whose expression is under transcriptional control of the transcription activator.

In this method, the haploid yeast cells of opposite mating types may preferably be a and α type strains of yeast. The mating between the first and second populations of haploid yeast cells of a and α type strains may be conducted in a rich nutritional culture medium.

Figure 2B:
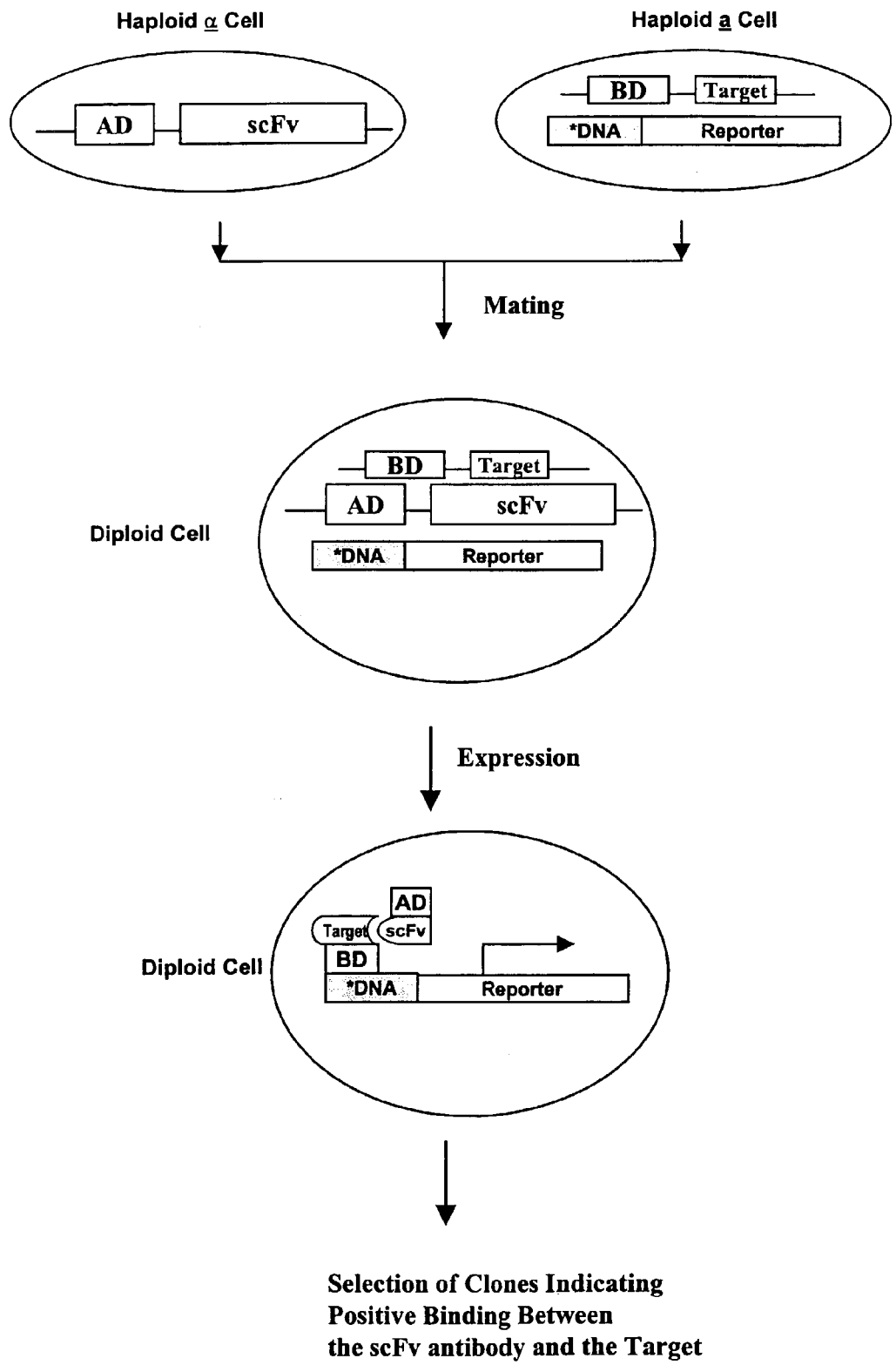
FIG. 2B illustrates another embodiment of the method of present invention for screening of scFv against a target peptide derived from a membrane protein via mating of two yeast strains.

FIG. 2B illustrates a flow diagram of a preferred embodiment of the above described method. As illustrated in FIG. 2B, the sequence library containing scFv fused with an AD domain upstream is carried by a library of expression vectors, the AD-scFv vectors. The library of the AD-scFv vectors are transformed into haploid yeast cells such as the a type strain of yeast.

The coding sequence of the target protein (labeled as "Target") is contained in another expression vector and fused with a BD domain, forming the BD-Target vector. The BD-Target vector is transformed into haploid cells of opposite mating type of the haploid cells containing the the AD-scFv vectors, such as the α type strain of yeast. The construct carrying the specific DNA binding site and the reporter gene (labeled as "Reporter") may be transformed into the haploid cells of either the type a or type α strain of yeast.

The haploid cells of the type a and type α strains of yeast are mated under suitable conditions such as low speed of shaking in liquid culture, physical contact in solid medium culture, and rich medium such as YPD. Bendixen, C. et al. (1994) "A yeast mating-selection scheme for detection of protein-protein interactions", Nucleic Acids Res. 22: 1778–1779. Finley, Jr., R. L. & Brent, R. (1994) "Interaction mating reveals linery and ternery connections between Drosophila cell cycle regulators", Proc. Natl. Acad. Sci. USA, 91:12980–12984. As a result, the AD-scFv, the BD- Target expression vectors and the Reporter construct are taken into the parental diploid cells of the a and type α strain of haploid yeast cells.

Upon expression of the sequences in the expression vectors in the parental diploid cells, the library of scFv fusion proteins undergo protein folding in the host cell and adopt various conformations. Some of the AD-scFv fusion proteins may bind to the Target protein expressed by the BD-Target vector in the parental diploid cell, thereby bringing the AD and BD domains to a close proximity in the promoter region (i.e., the specific DNA binding site) of the reporter construct and thus reconstituting a functional transcription activator composed of the AD and BD domains. As a result, the AD activates the transcription of the reporter gene downstream from the specific DNA binding site, resulting in expression of the reporter gene, such as the lacZ reporter gene. Clones showing the phenotype of the reporter gene expression are selected, and the AD-scFv vectors are isolated. The coding sequences for scFv are identified and characterized.

A wide variety of reporter genes may be used in the present invention. Examples of proteins encoded by reporter genes include, but are not limited to, easily assayed enzymes such as β-galactosidase, α-galactosidase, luciferase, β-glucuronidase, chloramphenicol acetyl transferase (CAT), secreted embryonic alkaline phosphatase (SEAP), fluorescent proteins such as green fluorescent protein (GFP), enhanced blue fluorescent protein (EBFP), enhanced yellow fluorescent protein (EYFP) and enhanced cyan fluorescent protein (ECFP); and proteins for which immunoassays are readily available such as hormones and cytokines. The expression of these reporter genes can also be monitored by measuring levels of mRNA transcribed from these genes.

When the screening of the scFv library is conducted in yeast cells, certain reporter(s) are of nutritional reporter which allows the yeast to grow on the specific selection medium plate. This is a very powerful screening process, as has been shown by many published papers. Examples of the nutritional reporter include, but are not limited to, His3, Ade2, Leu2, Ura3, Trp1 and Lys2. The His3 reporter is described in Bartel, P. L. et al. (1993) "Using the two-hybrid system to detect protein-protein interactions", in Cellular interactions in Development: A practical approach, ed. Hastley, D. A., Oxford Press, pages 153–179. The Ade2 reporter is described in Jarves, P. et al. (1996) "Genomic libraries and a host strain designed for highly efficient two-hybrid selection in yeast" Genetics 144:1425–1436.

For example, a library of scFv expression vectors that contains a scFv fused with an AD domain of GAL 4 transcription activator (the AD-scFv library) may be transformed into haploid cells of the α mating type of yeast strain. A BD domain of GAL 4 transcription activator is fused with the sequence encoding the target protein to be selected against the scFV library in a plasmid. This plasmid is transformed into haploid cells of the a mating type of yeast strain.

Equal volume of AD-scFv library-containing yeast stain (α-type) and the BD-target-containing yeast strain (a-type) are inoculated into selection liquid medium and incubated separately first. These two cultures are then mixed and allowed to grow in rich medium such as 1×YPD and 2×YPD. Under the rich nutritional culture condition, the two haploid yeast strains will mate and form diploid cells. At the end of this mating process, these yeast cells are plated on selection plates. A multiple-marker selection scheme may be used to select yeast clones that show positive interaction between the scFVs in the library and the target. For example, a scheme of SD/-Leu-Trp-His-Ade may be used. The first two selections (Leu-Trp) are for markers (Leu and Trp) expressed from the AD-scFv library and the BD-Target vector, respectively. Through this dual-marker selection, diploid cells retaining both BD and AD vectors in the same yeast cells are selected. The latter two markers, His-Ade, are used to screen for those clones that express the reporter gene from parental strain, presumably due to affinity binding between the scFv in the library and the target.

After the screening by co-transformation, or by mating screening as described above, the putative interaction between the gene probe and the library clone isolates can be further tested and confirmed in vitro or in vivo.

In vitro binding assays may be used to confirm the positive interaction between the scFv expressed by the clone isolate and the target peptide. For example, the in vitro binding assay may be a "pull-down" method, such as using GST (glutathione S-transferase)-fused gene probe as matrix-binding protein, and with in vitro expressed library clone isolate that are labeled with a radioactive or non-radioactive group. While the probe is bound to the matrix through GST affinity substrate (glutathione-agarose), the library clone isolate will also bind to the matrix through its affinity with the gene probe. The in vitro binding assay may also be a Co-immuno-precipitation (Co-IP) method using two affinity tag antibodies. In this assay, both the target gene probe and the library clone isolate are in vitro expressed fused with peptide tags, such as HA (haemaglutinin A) or Myc tags. The gene probe is first immuno-precipitated with an antibody against the affinity peptide tag (such as HA) that the target gene probe is fused with. Then the second antibody against a different affinity tag (such as Myc) that is fused with the library clone isolate is used for reprobing the precipitate.

In vivo assays may also be used to confirm the positive interaction between the scFv expressed by the clone isolate and the target peptide. For example, a mammalian two-hybrid system may serve as a reliable verification system for the yeast two-hybrid library screening. In this system, the target gene probe and library clone are fused with Gal 4 DNA-binding domain or an mammalian activation domain (such as VP-16) respectively. These two fusion proteins under control of a strong and constitutive mammalian promoter (such as CMV promoter) are introduced into mammalian cells by transfection along with a reporter responsive to Gal 4. The reporter can be CAT gene (chloramphenical acetate transferase) or other commonly used reporters. After 2–3 days of transfection, CAT assay or other standard assays will be performed to measure the strength of the reporter which is correlated with the strength of interaction between the gene probe and the library clone isolate.

It should be noted that the antibody library described above may be screened against a target peptide fragment derived from a membrane protein in other organisms or in vitro. For example, the target peptide may be expressed as a fusion protein with another protein and screened against the antibody library co-expressed in mammalian cells. The target peptide may also be immobilized to a substrate as a single peptide or a fusion protein and selected against a library of antibodies displayed by bacteriophagedisplayed, mRNA, ribosome or cells such as yeast cells. In addition, the target peptide may be introduced to a xenomouse, HuMab mouse, or a transchromosomal mouse which contains a library of human antibody, and selected for monoclonal human antibodies with specific binding affinity to target peptide and/or the target membrane protein.

For example, the library of human antibodies may be screened against a target peptide derived from a membrane protein (e.g., CCR5) by using ribosome display. Ribosome display is a form of protein display for in vitro selection against a target ligand. In this system, mRNA encoding the tester protein (e.g. an antibody) and the translated tester protein are associated through the ribosome complex, also called an antibody-ribosome-mRNA (ARM) complex. He and Taussig (1997) Nucleic Acid Research 25:5132–5134. The principle behind this approach is that single chain antibody can be functionally produced in an in vitro translation system (e.g. rabbit reticulocyte lysate), and in the absence of a stop codon, individual nascent proteins remain associated with their corresponding mRNa as stable ternary polypeptide-ribosome-mRNA complexes in such a cell-free system.

In the ribosome display assay, each member of the library of human antibody sequences includes a bacterial phage T7 promoter and protein synthesis initiation sequence attached to the 5' end of the cDNA encoding the antibody (e.g., scFv) and no stop codon in the 3' end. Because the cDNA pool is depleted of the stop codon, when the mRNA is transcribed from the cDNA and is subject to in vitro translation, the mRNA will still be attached to the ribosome and mRNA, forming the ARM complex. The library of human scFv antibody that is translated from the cDNA gene pool and displayed on the surface of the ribosome can be screened against the target peptide as a single peptide or as a fusion protein with a protein other than the target membrane protein. The in vitro transcription and translation of this library may be carried out in rabbit reticulocyte lysate in the presence of methionine at 30° C. by using the commercially available systems, such as TNT® T7 Quick Coupled Transcription/Translation System (Promega, Madison, Wis.).

The target peptide or its fusion protein may be immobilized to a solid substrate, such as a chromatography resin by covalent linkage to enrich for those ribosomes with high affinity humanized antibody attached. By affinity chromatography, the ribosomes with high affinity scFv antibody attached are isolated. The mRNA encoding the high affinity scFv antibody is recovered from the isolated ARM complexes and subject to reverse transcriptase (RT)/PCR to synthesize and amplify the cDNA of the selected antibody. This completes the first cycle of the panning process for antibody isolation and its coding sequence characterization. Such a panning process may be repeated until scFv antibody with desirably affinity is isolated.

Optionally, the library of human antibodies may be screened against a target peptide derived from a membrane protein (e.g., CCR5) by using mRNA display. Wilson et al. (2001) Proc Natl Acad Sci USA. 98:3750–3755; and Keefe and Szostak (2001) Nature 410:715–718. These documents, and all documents cited to herein, are incorporated by reference as if fully reproduced below. Each of the antibodies can be covalently linked through the carboxy terminus if the antibody is a single chain antibody or through the carboxy terminus of the light or heavy chain if the antibody is a Fv, Fab or a fully assembled antibody to the 3' end of its encoding mRNA.

The target peptide or its fusion protein may be immobilized to a solid substrate, such as a chromatography resin by covalent linkage to enrich for the mRNA to which high affinity humanized antibody is linked. The mRNA encoding the high affinity antibody is recovered from the isolated the mRNA-antibody conjugate and subject to reverse transcriptase (RT)/PCR to synthesize and amplify the cDNA of the selected antibody. This completes the first cycle of the panning process for antibody isolation and its coding sequence characterization. Such a panning process may be repeated until antibody with desirably affinity is isolated.

Also optionally, the library of human antibodies may be screened against a target peptide derived from a membrane protein (e.g., CCR5) by using yeast display. Boder et al. (2000) Proc Natl Acad Sci USA. 97:10701–10705; and Boder and Wittrup (1997) Nat Biotechnol. 15:553–557. These documents, and all documents cited to herein, are incorporated by reference as if fully reproduced below. For example, the library of antibodies may be display on the surface of yeast cells via C-terminal fusion to the Aga2p mating adhesion receptor of *Saccharomyces cerevisiae*. The displayed antibodies can be selected for binding to the target peptide or its fusion with a chaperon protein. Such a eukaryotic host may alleviate expression biases present in bacterially propagated combinatorial libraries.

The target peptide or its fusion protein may be immobilized to a solid substrate or present in a solution. For example, the target peptide or its fusion may be mixed with yeast cells which display the library of antibodies on the cell surface. The cell displaying the antibody that binds to the target may be selected by using flow cytometric cell sorting. The cDNA encoding the selected antibody can be recovered from the isolated cell. This completes the first cycle of the selection process for antibody isolation and its coding sequence characterization. Such a selection process may be repeated until antibody with desirably affinity is isolated.

6. Affinity Maturation of scFv Leads Positively Selected Against Target Peptide

The binding affinity of the primary scFv antibody leads can be improved by using an in vitro affinity maturation process according to the present invention. The coding sequences of these protein leads may be mutagenized in vitro or in vivo to generated a secondary library more diverse than these leads. The mutagenized leads can be selected against the target peptide again in vivo following similar procedures described for the selection of the primary library carrying scFv. Such mutagenesis and selection of primary antibody leads effectively mimics the affinity maturation process naturally occurring in a mammal that produces antibody with progressive increase in the affinity to the immunizing antigen.

The sequences encoding $V_H$ and $V_L$ of the primary antibody leads are mutagenized in vitro to produce a secondary antibody library. The $V_H$ and $V_L$ sequences can be randomly mutagenized by "poison" PCR (or error-prone PCR), by DNA shuffling, or by any other way of random or site-directed mutagenesis (or cassette mutagenesis). After mutagenesis in the regions of $V_H$ and $V_L$, the secondary antibody library formed by the mutants of the primary antibody can be screened against the peptide target by using the yeast two-hybrid system or other screening method. Mutants with higher affinity than the primary antibody lead can be isolated.

The coding sequences of the scFv leads may be mutagenized by using a wide variety of methods. Examples of methods of mutagenesis include, but are not limited to site-directed mutagenesis, error-prone PCR mutagenesis, cassette mutagenesis, random PCR mutagenesis, DNA shuffling, and chain shuffling.

Site-directed mutagenesis or point mutagenesis may be used to gradually change the $V_H$ and $V_L$ sequences in specific regions. This is generally accomplished by using oligonucleotide-directed mutagenesis. For example, a short sequence of a scFv antibody lead may be replaced with a synthetically mutagenized oligonucleotide. The method may not be efficient for mutagenizing large numbers of $V_H$ and $V_L$ sequences, but may be used for fine toning of a particular lead to achieve higher affinity toward a specific target protein.

Cassette mutagenesis may also be used to mutagenize the $V_H$ and $V_L$ sequences in specific regions. In a typical cassette mutagenesis, a sequence block, or a region, of a single template is replaced by a completely or partially randomized sequence. However, the maximum information content that can be obtained may be statistically limited by the number of random sequences of the oligonucleotides. Similar to point mutagenesis, this method may also be used for fine toning of a particular lead to achieve higher affinity toward a specific target protein.

Error-prone PCR, or "poison" PCR, may be used to the $V_H$ and $V_L$ sequences by following protocols described in Caldwell and Joyce (1992) PCR Methods and Applications 2:28–33. Leung, D. W. et al. (1989) Technique 1:11–15. Shafikhani, S. et al. (1997) Biotechniques 23:304–306. Stemmer, W. P. et al. (1994) Proc. Natl. Acad. Sci. USA 91:10747–10751.

Figure 4:
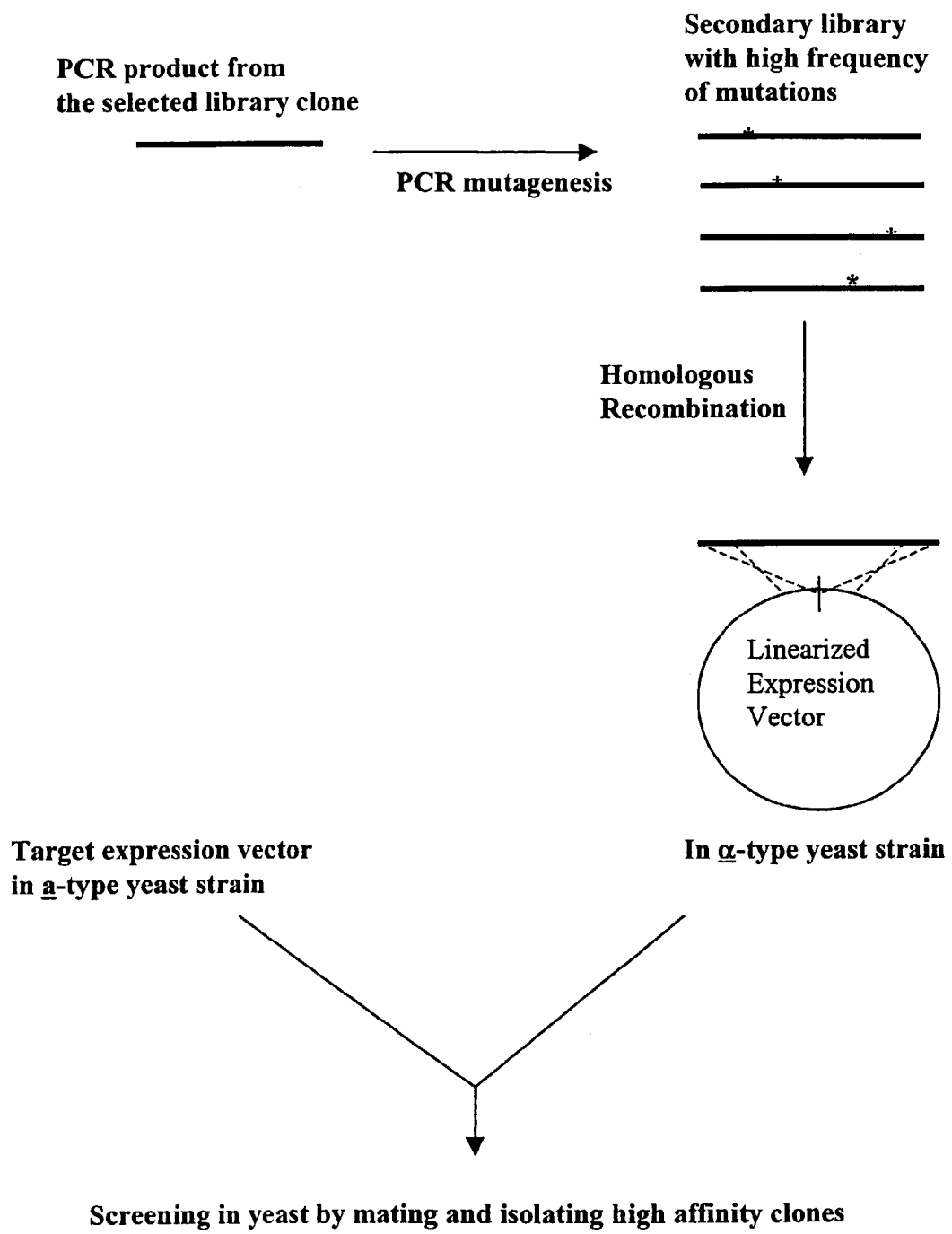
FIG. 4 illustrates a method of affinity maturation of an antibody lead.

FIG. 4 illustrates an example of the method of the present invention for affinity maturation of antibody leads selected from the primary scFv library. As illustrated in FIG. 4, the coding sequences of the scFv leads selected from clones containing the primary scFv library are mutagenized by using a poison PCR method. Since the coding sequences of the scFV library are contained in the expression vectors isolated from the selected clones, one or more pairs of PCR primers may be used to specifically amplify the $V_H$ and $V_L$ region out of the vector. The PCR fragments containing the $V_H$ and $V_L$ sequences are mutagenized by the poison PCR under conditions that favors incorporation of mutations into the product.

Such conditions for poison PCR may include a) high concentrations of $Mn^{2+}$ (e.g. 0.4–0.6 mM) that efficiently induces malfunction of Taq DNA polymerase; and b) disproportionately high concentration of one nucleotide substrate (e.g., dGTP) in the PCR reaction that causes incorrect incorporation of this high concentration substrate into the template and produce mutations. Additionally, other factors such as, the number of PCR cycles, the species of DNA polymerase used, and the length of the template, may affect the rate of mis-incorporation of "wrong" nucleotides into the PCR product. Commercially available kits may be utilized for the mutagenesis of the selected scFv library, such as the "Diversity PCR random mutagenesis kit" (catalog No. K1830-1, Clontech, Palo Alto, Calif.).

The PCR primer pairs used in mutagenesis PCR may preferably include regions matched with the homologous recombination sites in the expression vectors. This design allows re-introduction of the PCR products after mutagenesis back into the yeast host strain again via homologous recombination. This also allows the modified $V_H$ and $V_L$ region to be fused with the AD domain directly in the expression vector in the yeast.

Still referring to FIG. 4, the mutagenized scFv fragments are inserted into the expression vector containing an AD domain via homologous recombination in haploid cells of α type yeast strain. Similarly to the selection of scFv clones from the primary antibody library, the AD-scFv containing haploid cells are mated with haploid cells of opposite mating type (e.g. a type) that contains the BD-Target vector and the reporter gene construct. The parental diploid cells are selected based on expression of the reporter gene and other selection criteria as described in detail in Section 5.

Other PCR-based mutagenesis method can also be used, alone or in conjunction with the poison PCR described above. For example, the PCR amplified $V_H$ and $V_L$ segments may be digested with DNase to create nicks in the double DNA strand. These nicks can be expanded into gaps by other exonucleases such as Bal 31. The gaps may be then be filled by random sequences by using DNA Klenow polymerase at low concentration of regular substrates dGTP, dATP, dTTP, and dCTP with one substrate (e.g., dGTP) at a disproportionately high concentration. This fill-in reaction should produce high frequency mutations in the filled gap regions. These method of DNase I digestion may be used in conjunction with poison PCR to create highest frequency of mutations in the desired $V_H$ and $V_L$ segments.

The PCR amplified $V_H$ and $V_L$ segments or the scFv segments amplified from the primary antibody leads may be mutagenized in vitro by using DNA shuffling techniques described by Stemmer (1994) Nature 370:389–391; and Stemmer (1994) Proc. Natl. Acad. Sci. USA 91:10747–10751. The $V_H$, $V_L$ or scFV segments from the primary antibody leads are digested with DNase I into random fragments which are then reassembled to their original size by homologous recombination in vitro by using PCR methods. As a result, the diversity of the library of primary antibody leads are increased as the numbers of cycles of molecular evolution increase in vitro.

The $V_H$, $V_L$ or scFv segments amplified from the primary antibody leads may also be mutagenized in vivo by exploiting the inherent ability of mution in pre-B cells. The Ig gene in pre-B cells is specifically susceptible to a high-rate of mutation in the development of pre-B cells. The Ig promoter and enhancer facilitate such high rate mutations in a pre-B cell environment while the pre-B cells proliferate. Accordingly, $V_H$ and $V_L$ gene segments may be cloned into a mammalian expression vector that contains human Ig enhancer and promoter. This construct may be introduced into a pre-B cell line, such as 38B9, which allows the mutation of the $V_H$ and $V_L$ gene segments naturally in the pre-B cells. Liu, X., and Van Ness, B. (1999) Mol. Immunol. 36:461–469. The mutagenized $V_H$ and $V_L$ segments can be amplified from the cultured pre-B cell line and re-introduced back into the AD-containing yeast strain via, for example, homologous recombination.

The secondary antibody library produced by mutagenesis in vitro (e.g. PCR) or in vivo, i.e., by passing through a mammalian pre-B cell line may be cloned into an expression vector and screened against the same target protein as in the first round of screening using the primary antibody library. For example, the expression vectors containing the secondary antibody library may be transformed into haploid cells of α type yeast strain. These α cells are mated with haploid cells a type yeast strain containing the BD-target expression vector and the reporter gene construct. The positive interaction of scFvs from the secondary antibody library is screened by following similar procedures as described for the selection of the primary antibody leads in yeast.

Alternatively, since the secondary antibody library may be relatively low in complexity (e.g., $10^4$–$10^5$ independent clones) as compared to the primary libraries (e.g., $10^7$–$10^{14}$), the screening of the secondary antibody library may be performed without mating between two yeast strains. Instead, the linearized expression vectors containing the AD domain and the mutagenized $V_H$ and $V_L$ segments may be directly co-transformed into yeast cells containing the BD-target expression vector and the reporter gene construct. Via homologous recombination in yeast, the secondary antibody library are expressed by the recombined AD-scFv vector and screened against the target protein expressed by the BD-target vector by following similar procedures as described for the selection of the primary antibody leads in yeast.

7. Functional Expression and Purification of Selected Antibody

The library of scFv fusion protens that are generated and selected in the screening against the target protein(s) may be expressed in hosts after the $V_H$ and $V_L$ sequences are operably linked to an expression control DNA sequence, including naturally-associated or heterologous promoters, in an expression vector. By operably linking the $V_H$ and $V_L$ sequences to an expression control sequence, the $V_H$ and $V_L$ coding sequences are positioned to ensure the transcription and translation of these inserted sequences. The expression vector may be replicable in the host organism as episomes or as an integral part of the host chromosomal DNA. The expression vector may also contain selection markers such as antibiotic resistance genes (e.g. neomycin and tetracycline resistance genes) to permit detection of those cells transformed with the expression vector.

Preferably, the expression vector may be a eukaryotic vector capable of transforming or transfecting eukaryotic host cells. Once the expression vector has been incorporated into the appropriate host cells, the host cells are maintained under conditions suitable for high level expression of the single-chains polypeptide encoded by a scFv. The polypeptides expressed are collected and purified depending on the expression system used.

The scFv, Fab, or fully assembled antibodies selected by using the methods of the present invention may be expressed in various scales in any host system such as bacteria (e.g. E. coli), yeast (e.g. S. cerevisiae), and mammalian cells (COS). The bacteria expression vector may preferably contain the bacterial phage T7 promoter and express a single chain variable fragment (scFv). The yeast expression vector may contain a constitutive promoter (e.g. ADGI promoter) or an inducible promoter such as (e.g. GCN4 and Gal 1 promoters). All three types of antibody, scFv, Fab, and full antibody, may be expressed in a yeast expression system.

The expression vector may be a mammalian express vector that can be used to express the single-chains polypeptide encoded by $V_H$ and $V_L$ in mammalian cell culture transiently or stably. Examples of mammalian cell lines that may be suitable of secreting immunoglobulins include, but are not limited to, various COS cell lines, HeLa cells, myeloma cell lines, CHO cell lines, transformed B-cells and hybridomas.

Typically, a mammalian expression vector includes certain expression control sequences, such as an origin of replication, a promoter, an enhancer, as well as necessary processing signals, such as ribosome binding sites, RNA splice sites, polyadenylation sites, and transcriptional terminator sequences. Examples of promoters include, but are not limited to, insulin promoter, human cytomegalovirus (CMV) promoter and its early promoter, simian virus SV40 promoter, Rous sarcoma virus LTR promoter/enhancer, the chicken cytoplasmic β-actin promoter, promoters derived from immunoglobulin genes, bovine papilloma virus and adenovirus.

One or more enhancer sequence may be included in the expression vector to increase the transcription efficiency. Enhancers are cis-acting sequences of between 10 to 300 bp that increase transcription by a promoter. Enhancers can effectively increase transcription when positioned either 5' or 3' to the transcription unit. They may also be effective if located within an intron or within the coding sequence itself. Examples of enhancers include, but are not limited to, SV40 enhancers, cytomegalovirus enhancers, polyoma enhancers, the mouse immunoglobulin heavy chain enhancer, and adenovirus enhancers.

The mammalian expression vector may also typically include a selectable marker gene. Examples of suitable markers include, but are not limited to, the dihydrofolate reductase gene (DHFR), the thymidine kinase gene (TK), or prokaryotic genes conferring antibiotic resistance. The DHFR and TK genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The expression vectors containing the scFv sequences can then be transferred into the host cell by methods known in the art, depending on the type of host cells.

Examples of transfection techniques include, but are not limited to, calcium phosphate transfection, calcium chloride transfection, lipofection, electroporation, and microinjection.

The $V_H$ and $V_L$ sequences may also be inserted into a viral vector such as adenoviral vector that can replicate in its host cell and produce the polypeptide encoded by $V_H$ and $V_L$ in large amounts.

In particular, the scFv, Fab, or fully assembled antibody may be expressed in mammalian cells by using a method described by Persic et al. (1997) Gene, 187:9–18. The mammalian expression vector that is described by Persic and contains EF-α promoter and SV40 replication origin is preferably utilized. The SV40 origin allows a high level of transient expression in cells containing large T antigen such as COS cell line. The expression vector may also include secretion signal and different antibiotic markers (e.g. neo and hygro) for integration selection.

Once expressed, polypeptides encoded by $V_H$ and $V_L$ may be isolated and purified by using standard procedures of the art, including ammonium sulfate precipitation, fraction column chromatography, and gel electrophoresis. Once purified, partially or to homogeneity as desired, the polypeptides may then be used therapeutically or in developing, performing assay procedures, immunofluorescent stainings, and in other biomedical and industrial applications. In particular, the antibodies generated by the method of the present invention may be used for diagnosis and therapy for the treatment of various diseases such as cancer, autoimmune diseases, or viral infections.

In a preferred embodiment, the scFv human antibody with $V_H$ and $V_L$ segments that are generated and screened by using the methods of the present invention may be expressed directly in yeast. According to this embodiment, the $V_H$ and $V_L$ regions from the selected expression vectors may be PCR amplified with primers that simultaneously add appropriate homologous recombination sequences to the PCR products. These PCR segments of $V_H$ and $V_L$ may then be introduced into a yeast strain together with a linearized expression vector containing desirable promoters, expression tags and other transcriptional or translational signals.

For example, the PCR segments of $V_H$ and $V_L$ regions may be homologously recombined with a yeast expression vector that already contains a desirable promoter in the upstream and stop codons and transcription termination signal in the downstream. The promoter may be a constitutive expression promoter such as ADH1, or an inducible expression promoter, such as Gal 1, or GCN4 (A. Mimran, I. Marbach, and D. Engelberg, (2000) Biotechniques 28:552–560). The latter inducible promoter may be preferred because the induction can be easily achieved by adding 3-AT into the medium.

The yeast expression vector to be used for expression of the scFv antibody may be of any standard strain with nutritional selection markers, such as His 3, Ade 2, Leu 2, Ura 3, Trp 1 and Lys 2. The marker used for the expression of the selected scFv may preferably be different from the AD vector used in the selection of scFv in the two-hybrid system. This may help to avoid potential carryover problem associated with multiple yeast expression vectors.

For expressing the scFv antibody in a secreted form in yeast, the expression vector may include a secretion signal in the 5' end of the $V_H$ and $V_L$ segments, such as an alpha factor signal and a 5-pho secretion signal. Certain commercially available vectors that contain a desirable secretion signal may also be used (e.g., pYEX-S1, catalog # 6200-1, Clontech, Palo Alto, Calif.).

The scFv antibody fragments generated may be analyzed and characterized for their affinity and specificity by using methods known in the art, such as ELISA, western, and immune staining. Those scFv antibody fragments with reasonably good affinity (with dissociation constant preferably lower than $10^{-6}$ M) and specificity can be used as building blocks in Fab expression vectors, or can be further assembled with the constant region for full length antibody expression. These fully assembled human antibodies may also be expressed in yeast in a secreted form.

The $V_H$ sequence encoding the selected scFv protein may be linked with the constant regions of a full antibody, $C_H1$, $C_H2$ and $C_H3$. Similarly, the $V_L$ sequence may be linked with the constant region $C_L$. The assembly of two units of $V_H$-$C_H1$-$C_H2$-$C_H3$ and $V_L$-$C_L$ leads to formation of a fully functional antibody. The present invention provides a method for producing fully functional antibody in yeast. Fully functional antibody retaining the rest of the constant regions may have a higher affinity (or avidity) than a scFv or a Fab. The full antibody should also have a higher stability, thus allowing more efficient purification of antibody protein in large scale.

The method is provided by exploiting the ability of yeast cells to uptake and maintain multiple copies of plasmids of the same replication origin. According to the method, different vectors may be used to express the heavy chain and light chain separately, and yet allows for the assembly of a fully functional antibody in yeast. This approach has been successfully used in a two-hybrid system design where the BD and AD vectors are identical in backbone structure except the selection markers are distinct. This approach has been used in a two-hybrid system design for expressing both BD and AD fusion proteins in the yeast. The BD and AD vectors are identical in their backbone structures except the selection markers are distinct. Both vectors can be maintained in yeast in high copy numbers. Chien, C. T., et al. (1991) "The two-hybrid system: a method to identify and clone genes for proteins that interact with a protein of interest" Proc. Natl. Acad. Sci. USA 88:9578–9582.

In the present invention, the heavy chain gene and light chain genes are placed in two different vectors. Under a suitable condition, the $V_H$-$C_H1$-$C_H2$-$C_H3$ and $V_L$-$C_L$ sequences are expressed and assembled in yeast, resulting in a fully functional antibody protein with two heavy chains and two light chains. This fully functional antibody may be secreted into the medium and purified directly from the supernatant.

The scFv with a constant region, Fab, or fully assembled antibody can be purified using methods known in the art. Conventional techniques include, but are not limited to, precipitation with ammnonium sulfate and/or caprylic acid, ion exchange chromatography (e.g. DEAE), and gel filtration chromatography. Delves (1997) "Antibody Production: Essential Techniques", New York, John Wiley & Sons, pages 90–113. Affinity-based approaches using affinity matrix based on Protein A, Protein G or Protein L may be more efficiency and results in antibody with high purity. Protein A and protein G are bacterial cell wall proteins that bind specifically and tightly to a domain of the Fc portion of certain immunoglobulins with differential binding affinity to different subclasses of IgG. For example, Protein G has higher affinities for mouse IgG1 and human IgG3 than does Protein A. The affinity of Protein A of IgG1 can be enhanced by a number of different methods, including the use of binding buffers with increased pH or salt concentration. Protein L binds antibodies predominantly through kappa light chain interactions without interfering with the antigen-binding site. Chateau et al. (1993) "On the interaction between Protein L and immunoglobulins of various mammalian species" Scandinavian J. Immunol., 37:399–405. Protein L has been shown to bind strongly to human kappa light chain subclasses I, III and IV and to mouse kappa chain subclasses I. Protein L can be used to purify relevant kappa chain-bearing antibodies of all classes (IgG, IgM, IgA, IgD, and IgE) from a wide variety of species, including human, mouse, rat, and rabbit. Protein L can also be used for the affinity purification of scFv and Fab antibody fragments containing suitable kappa light chains. Protein L-based reagents is commercially available from Actigen, Inc., Cambridgem, England. Actigen can provide a line of recombinant Protein products, including agarose conjugates for affinity purification and immobilized forms of recombinant Protein L and A fusion protein which contains four protein A antibody-binding domains and four protein L kappa-binding domains.

Other affinity matrix may also be used, including those that exploit peptidomimetic ligands, anti-immunoglobulins, mannan binding protein, and the relevant antigen. Peptidomimetic ligands resemble peptides but they do not correspond to natural peptides. Many of Peptidomimetic ligands contain unnatural or chemically modified amino acids. For example, peptidomimetic ligands designed for the affinity purification of antibodies of the IGA and IgE classes are commercially available from Tecnogen, Piana di Monte Verna, Italy. Mannan binding protein (MBP) is a mannose- and N-acetylglucosamine-specific lectin found in mammalian sera. This lectin binds IgM. The MBP-agarose support for the purification IgM is commercially available from Pierce.

Immunomagnetic methods that combine an affinity reagent (e.g. protein A or an anti-immunoglobulin) with the ease of separation conferred by paramagnetic beads may be used for purifying the antibody produced. Magnetic beads coated with Protein or relevant secondary antibody may be commercially available from Dynal, Inc., NY; Bangs Laboratories, Fishers, Ind.; and Cortex Biochem Inc., San Leandro, Calif.

Direct expression and purification of the selected antibody in yeast is advantageous in various aspects. As a eukaryotic organism, yeast is more of an ideal system for expressing human proteins than bacteria or other lower organisms. It is more likely that yeast will make the scFv, Fab, or fully assembled antibody in a correct conformation (folded correctly), and will add post-translation modifications such as correct disulfide bond(s) and glycosylations.

Yeast has been explored for expressing many human proteins in the past. Many human proteins have been successfully produced from the yeast, such as human serum albumin (Kang, H. A. et al. (2000) Appl. Microbiol. Biotechnol. 53:578–582) and human telomerase protein and RNA complex (Bachand, F., et al. (2000) RNA 6:778–784).

Yeast has fully characterized secretion pathways. The genetics and biochemistry of many if not all genes that regulate the pathways have been identified. Knowledge of these pathways should aid in the design of expression vectors and procedures for isolation and purification of antibody expressed in the yeast.

Moreover, yeast has very few secreted proteases. This should keep the secreted recombinant protein quite stable. In addition, since yeast does not secrete many other and/or toxic proteins, the supernatant should be relatively uncontaminated. Therefore, purification of recombinant protein from yeast supernatant should be simple, efficient and economical.

Additionally, simple and reliable methods have been developed for isolating proteins from yeast cells. Cid, V. J. et al. (1998) "A mutation in the Rho&GAP-encoding gene BEM2 of *Saccharomyces cerevisiae* affects morphogenesis and cell wall functionality" Microbiol. 144:25–36. Although yeast has a relatively thick cell wall that is not present in either bacterial or mammalian cells, the yeast cells can still keep the yeast strain growing with the yeast cell wall striped from the cells. By growing the yeast strain in yeast cells without the cell wall, secretion and purification of recombinant human antibody may be made more feasible and efficient.

By using yeast as host system for expression, a streamlined process can be established to produce recombinant antibodies in fully assembled and purified form. This may save tremendous time and efforts as compared to using any other systems such as humanization of antibody in vitro and production of fully human antibody in transgenic animals.

In summary, the compositions, kits and methods provided by the present invention should be very useful for selecting proteins such as human antibodies with high affinity and specificity against a wide variety of targets including, but not limited to, soluble proteins (e.g. growth factors, cytokines and chemokines), membrane-bound proteins (e.g. cell surface receptors), and viral antigens. The whole process of library construction, functional screening and expression of highly diverse repertoire of human antibodies can be streamlined, and efficiently and economically performed in yeast in a high throughput and automated manner. The selected proteins can have a wide variety of applications. For example, they can be used in therapeutics and diagnosis of diseases including, but not limited to, autoimmune diseases, cancer, transplant rejection, infectious diseases and inflammation.

EXAMPLE

1. Construction of Human Single Chain Antibody Library

A human scFv library was constructed in a yeast two-hybrid vector pACT2 that contains sequence encoding Gal4 activation domain (AD) (Li et al. (1994) "Specific association between the human DNA repair proteins XPA and ERCC1" Proc Natl Acad Sci U S A. 91:5012–5016). cDNA encoding the variable regions of heavy ($V_H$) and light chain ($V_L$) were amplified by RT-PCR from poly $A^+$ RNA of human spleen, bone marrow, fetal liver and peripheral blood leukocytes (PBL). The $V_H$ and $V_L$ cDNA fragments were linked by a linker encoding [(Gly)$_4$Ser]$_4$ (Nicholls et al. (1993) "An improved method for generating single-chain antibodies from hybridomas" J Immunol Methods 165: 81–91), and are flanked by sequences of approximately 60 bp at each end that are homologous to the pACT2 multiple cloning sites (MCS) (Hua, et al, (1998) "Construction of a modular yeast two-hybrid cDNA library from human EST clones for the human genome protein linkage map" Gene. 215:143–152). Such assembled PCR products were cloned into pACT2 by homologous recombination (Hua et al, 1997) in yeast cells (MATα strains Y187 or MaV203) (Harper et al, (1993) "The p21 Cdk-interacting protein Cip1 is a potent inhibitor of G1 cyclin-dependent kinases" Cell 75:805–16; Vidal et al. (1996) "Reverse two-hybrid and one-hybrid systems to detect dissociation of protein-protein and DNA-protein interactions" Proc Natl Acad Sci U S A. 93:10315–10320). Such derived human scFvs are fused in-frame with the Gal4 activation domain. A total of 5×10$^7$ independent yeast colonies were harvested and stored at −80° C.

More specifically, poly $A^+$ RNA from human bone marrow, human fetal liver, human spleen and human peripheral blood leukocytes were purchased from Clontech Laboratories (Palo Alto, Calif.). First strand cDNA were made from the poly $A^+$ RNA using random primer and PowerScript reverse transcriptase kit (Clontech Laboratories, Palo Alto, Calif.). A set of oligonucleotides designed by Sblattero and Bradbury (Sblattero and Bradbury (1998) "A definitive set of oligonucleotide primers for amplifying human V regions" Immunotechnology. 3:271–278) that recognize all functional V genes were used to amplify all variable regions of heavy chain and light chain of human antibodies in PCR (Marks et al. (1991) "By-passing immunization: Human antibodies from V-gene libraries displayed on phage" J Mol Biol. 222:581–597).

The cDNA of heavy chain variable region ($V_H$) and light chain variable region ($V_L$) were linked by a short linker sequence encoding [(Gly)$_4$Ser]$_4$ (5'-GGC GGT GGT GGA TCA GGC GGC GGA GGA TCT GGC GGA GGT GGC AGC GGT GGT GGA GGC AGT-3' [SEQ ID NO: 5]) (Nicholls et al. (1993) "An improved method for generating single-chain antibodies from hybridomas" J Immunol Methods 165:81–91). The $V_H$-linker-$V_L$ cassettes were flanked by 60 base pairs (bp) at its 5' end and 57 bp at its 3' end of sequence homologous to the sequence adjacent to multiple cloning site of the yeast two-hybrid vector pACT2 (Hua et al, (1997), supra, Hua et al (1998), supra).

The 5' (1.3.a) and 3' homologous sequence (1.3.b) are as follows:

[SEQ ID NO: 6]
1.3.a: 5'-ACC CCA CCA AAC CCA AAA AAA GAG ATC TGT ATG GCT TAC CCA TAC GAT GTT CCA GAT TAC

[SEQ ID NO: 7]
1.3/b: 5-GAG ATG GTG CAC GAT GCA CAG TTG AAG TGA ACT TGC GGG GTT TTT CAG TAT CTA CGA

The above-assembled PCR products containing scFv were co-transformed with linearized pACT2 DNA (Hua et al. (1997), supra) into yeast strains Y187 (MATα, ura3-52, his3-200, ade2-101, lys2-801, trp1-901, leu2-3,112, gal4 Δ, gal80Δ, URA3::GAL1$_{UAS}$-GAL1$_{TATA}$-lacZ) (Harper et al, 1993) or MaV203 (MATα, ura3-52, his3Δ200, ade2-101, trp1-901, leu2-3,112, cyh2$^R$, can1$^R$, gal4 Δ, gal80Δ, GAL1::

lacZ, HIS3$_{UASGAL1}$::HIS3@LYS2, SPAL10::URA3) (Vidal et al. (1996) "Reverse two-hybrid and one-hybrid systems to detect dissociation of protein-protein and DNA-protein interactions" Proc Natl Acad Sci U S A. 93:10315–10320). The transformants were plated on yeast synthetic medium lacking leucine (SD/-L) and incubated at 30° C. for 2 days. A total of approximately 5×10$^7$ independent colonies of the yeast two-hybrid scFv library were harvested and stored at −80° C.

2. Construction of a Yeast Expression Vector Encoding Peptide Fragments Derived from Human CCR5

Peptide fragments derived from human CCR5 were used as target peptides against which the scFv library constructed above was screened. Three extracellular domains of human CCR5 cDNA, an N-terminal fragment, the 4$^{th}$ loop (or loop 4) and the 6$^{th}$ loop (or loop 6), were separately PCR-amplified from human leukocyte cDNA (Clontech Laboratories, Inc., Palo Alto, Calif.) using the following oligonucleotide primers. For amplification of the N-terminus of human CCR5 (aa 1–36), the primer pair are:

```
                                          [SEQ ID NO: 49]
13.13.L    5'-GGA GAA TTC GATTATCAAGTGTCAAGTCCA

[SEQ ID NO: 50]
13.13.M    5'-CGC GGA TCC TTA GAGCGGAGGCAGGAGGCGG
```

Primer 13.13.L corresponds to the N-terminus of CCR5, with an Eco R1 site added. Primer 13.13.M complements the sequence at the end of N-terminal extracellular domain (aa 36) of CCR5, with Bam HI and Stop codon added.

For amplification of the 4$^{th}$ loop of human CCR5 (aa 167–198), the primer pair are:

```
                                          [SEQ ID NO: 51]
13.13.N    5'-GGA GAA TTC ACCAGATCTCAAAAAGAAGG

[SEQ ID NO: 52]
13.13.O    5'-CGC GGA TCC TTA TATCTTTAATGTCTGGAAATT
```

Primer 13.13.N corresponds the sequence at the N-terminus of 4$^{th}$ loop of CCR5 (aa 167), with Eco RI site added. Primer 13.13.O complements the sequence at the C-terminus of 4$^{th}$ loop of CCR5 (aa 198), with Bam HI and Stop codon added.

For amplification of the 6$^{th}$ loop of CCR5 (aa 262–290), the primer pair are:

```
                                          [SEQ ID NO: 53]
13.13.P    5'-CAG GAA TTC TTTGGCCTGAAT

[SEQ ID NO: 54]
13.13.Q    5'-CGC GGA TCC TCA GCAGTGCGTCATCCCAAGA
```

Primer 13.13.P corresponds the sequence at the N-terminus of 6$^{th}$ loop of hCCR5 (aa 262) at the Eco RI site. Primer 13.13.Q complements the sequence at the C-terminus of 6$^{th}$ loop of CCR5 (aa 290), with Bam HI and Stop codon added.

The PCR product of each of the domains was cloned into an Eco RI/Bam HI-digested cloning vector pGBKT7 (Clontech Laboratories, Palo Alto, Calif.) with the Gal4 DNA binding domain (DNA-BD) at its carboxy terminus. The resulting plasmids were designated as follows:

```
pG90: pGBKT7-CCR5 N-terminus;

pG91: pGBKT7-CCR5 loop 4;

pG92: pGBKT7-CCR5 loop 6.
```

Each of the above plasmids encoding CCR5 peptide fragments was transformed into yeast strain AH109 (MATa, ura3-52, his3-200, ade2-101, trp1-901, leu2-3,112, gal4 Δ, gal80Δ, LYS2::GAL1$_{UAS}$-GAL1$_{TATA}$-HIS3, GAL2$_{UAS}$-GAL2$_{TATA}$-ADE2, URA3::MEL1$_{UAS}$-MEL1$_{TATA}$-lacZ) (Clontech Laboratories, Palo Alto, Calif.). The transformants were selected on synthetic medium lacking tryptophan (SD/-W).

3. Screening of a Human scFv Library Against Extracellular Domains of Human CCR5

To screen the scFv library against the extracellular domains of human CCR5, the AH109 transformants containing one of the three extracellular domains were mated with MATα type yeast cells (Y187 or MaV203 strain) containing the scFv library following the protocols from Clontech Laboratories. The scFv library-containing vector pACT2 contains a LEU2 gene, whereas the pGBKT7 plasmids contain a TRP1 gene. Cells harboring both plasmids can grow in the yeast synthetic medium lacking leucine and tryptophan (SD/-LW). Interactions between a scFv and the target CCR5 domain activated expression of reporter genes ADE2 and HIS3 built in genome of the strains, thus allowing the cells to grow on medium lacking adenine, histidine, leucine and tryptophan (SD/-AHLW). Colonies that were able to grow on SD/-ALHW medium were picked. These colonies were assayed for the expression of additional reporter gene/acZ in the β-galactosidase colony-lifting assay as described in the instruction manual from Clontech Laboratories. Plasmid DNA of pACT2 containing the scFv fragment was retrieved from the yeast cells.

To analyze the specificity of those scFv clones isolated from the above-mentioned library screening, pGBKT7 plasmids encoding CCR5 domains, empty vector pGBKT7 and pGBKT7-Lam (Clontech) (which contains sequence of human lamin C), were co-transformed, respectively, with individual scFv plasmids into yeast cells, followed by growth selection on SD/-LW or SD/-AHLW media. Yeast colonies grown on the selection media were subjected to β-galactosidase activity assays. The sequences of those scFv clones specific to human CCR5 domains were determined with an ABI automatic sequencer.

From the above library screening and specificity analysis, one specific scFv clone (clone 15.186.35) was obtained against the N-terminal fragment of human CCR5, and 3 specific scFv clones against Loop 6 of human CCR5: clones 15.150.11, 15.150.12, and 15.150.24. The DNA and amino acid sequences encoding these four clones are listed in FIG. 5. In addition, some variants of the four clones with slight modifications in the sequences in the framework regions are listed in FIG. 6.

4. Inhibition of HIV-1 Infection by the Selected Human Monoclonal Antibody

ScFv clones 15.150.11 and 15.150.12 were cloned into E. coli expression vector pET27b(+) (Novagen) to facilitate expression of scFv antibodies of Ab32 and Ab33, respectively. ScFv proteins were expressed and purified from the periplasmic space of the bacteria. The ability of the selected anti-CCR5 scFv antibodies, Ab32 and Ab33, to inhibit HIV-1 infection was determined by using an assay described in Cotter et al. (2001) J. Virol. 75:4308–4320. The control scFv antibody used was anti-human p53 scFv antibody.

Human monocytes were recovered from peripheral blood mononuclear cells of HIV-1-, HIV-2-, and hepatitis B virus-seronegative donors after leukapheresis and then purified by countercurrent centrifugal elutriation. Monocytes were cultured as adherent monolayers and differentiated for 7 days into macrophages (monocyte-derived macrophages or MDM). MDM were first incubated with different concentrations of scFv antibodies, then infected with HIV-1. HIV-1 reverse transcriptase (RT) activity was determined at Day 4, Day 8 and Day 12, as incorporation of [$^3$H]TTP (Cotter et al, 2001, J. Virol. 75:4308–4320). Radiolabeled nucleotides were precipitated with cold 10% trichloroacetic acid on paper filters in an automatic cell harvester and washed with 95% ethanol. Radioactivity was estimated by liquid scintillation spectroscopy. The cell viability was determined by MTT assay. Briefly, MTT (3-{4,5-Dimethylthiazol-2-yl]-2, 5-diphenyltetrazolium bromide, from Sigma) was dissolved in cell culture medium without phenol red. Live cells will convert MTT into purple dye inside cells. The dye was solubilized with acidic isopropanol and absorbance (OD) of the converted dye was measured at 570 nm. Mossman T., 1983, J. Immunol. Methods 65:55.

Figure 9A:
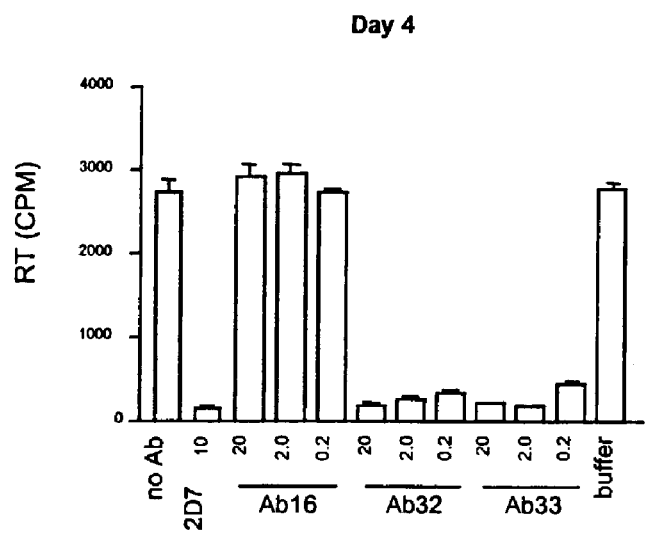
FIGS. 9A–C show HIV-1 reverse transcriptase (RT) activity in a culture of human monocytes infected by HIV-1 in the present or absent of antibody on day 4, 8, and 12 post infection, respectively.
Figure 9B:
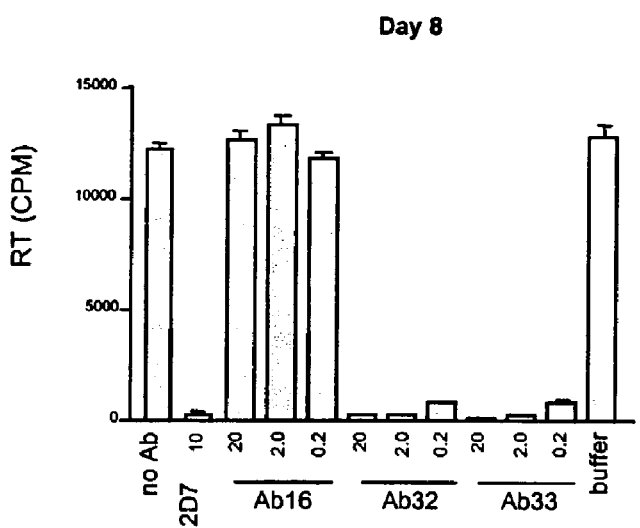
Figure 9C:
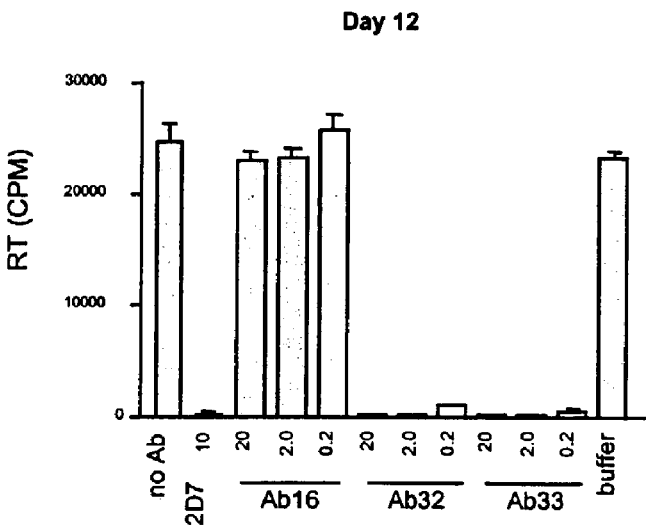
Figure 10A:
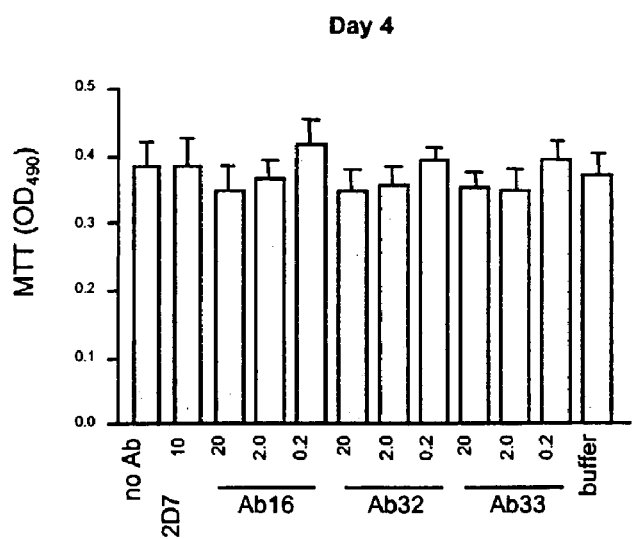
FIGS. 10A–C show viability of a culture of human monocytes infected by HIV-1 in the present or absent of antibody on day 4, 8, and 12 post infection, respectively.
Figure 10B:
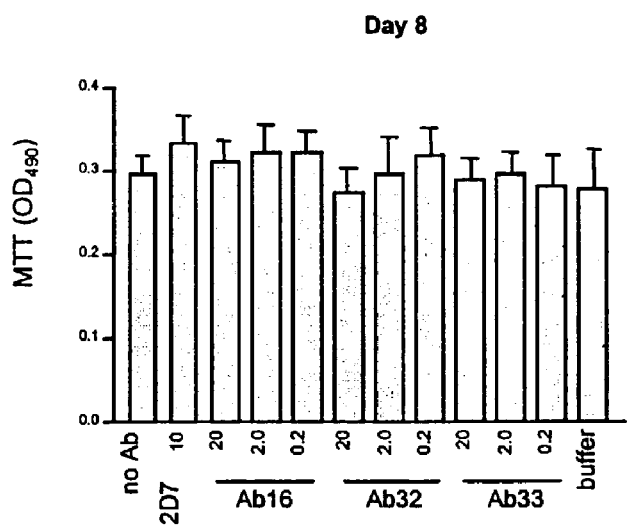
Figure 10C:
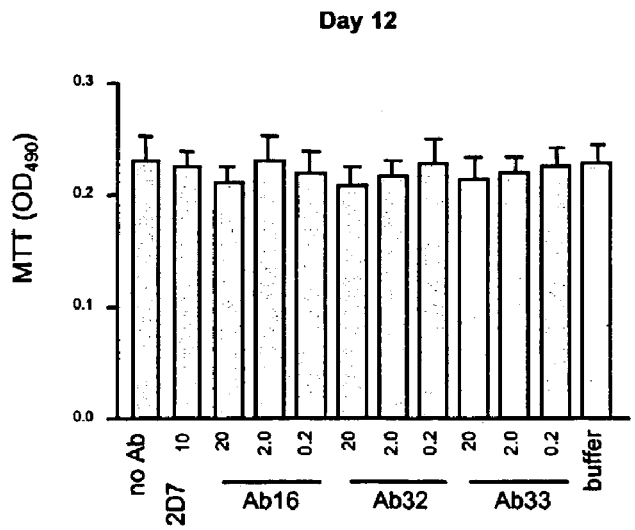

FIGS. 9A–C show HIV-1 RT activity in monocytes infected by HIV-1 in the presence or absence of two selected scFv antibodies against human CCR5 Loop (Ab32 and AB33) of the present invention on day 4, 8, and 12 post infection, respectively. As shown in FIGS. 9A–C, both Ab32 and AB33 effectively inhibit HIV-1 RT activity at concentrations 20, 2.0 and 0.2 µg/mL. In contrast, a non-specific antibody which is elicited against the tumor suppressor p53 protein), Ab 16, is completely ineffective in inhibition of HIV-1 RT activity. The positive control, a murine monoclonal antibody 2D7 (available from Pharmingen, San Diego, Calif.) could inhibit HIV-1 RT activity at a concentration of 10 µg/mL. In the absence of antibodies or with addition of mere buffer the HIV RT activity is completely uninhibited. Throughout the incubation period, the HIV-infected monocytes had normal viability in the presence or absence of these antibodies, as shown in FIGS. 10A–C.

Figure 11A:
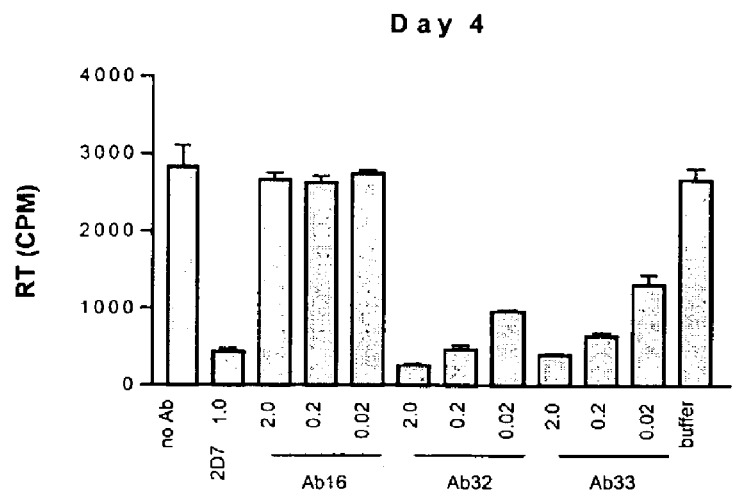
FIGS. 11A–C show HIV-1 reverse transcriptase (RT) activity in a culture of human monocytes infected by HIV-1 in the present or absent of antibody at lower concentrations than those in FIGS. 9A–C on day 4, 8, and 12 post infection, respectively.
Figure 11B:
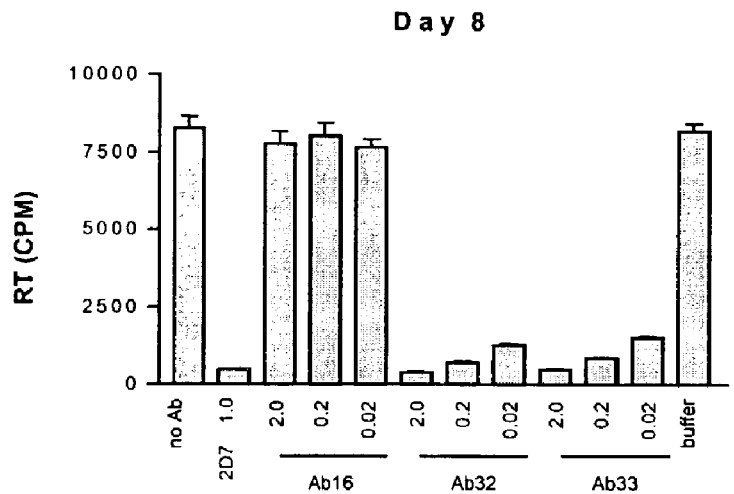
Figure 11C:
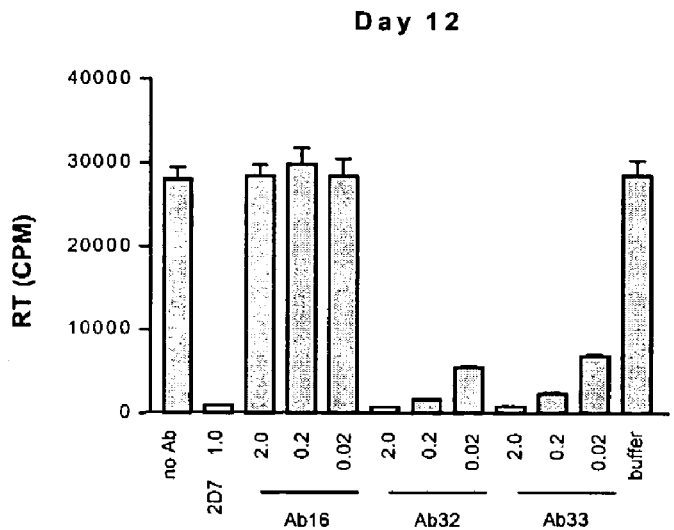

More significantly, when the concentrations of both Ab32 and AB33 were lowered to 0.02 µg/mL, these two scFv antibodies were still effectively inhibit inhibit HIV-1 RT activity. FIGS. 11A–C show HIV-1 RT activity in monocytes infected by HIV-1 in the presence or absence of Ab32 and AB33 at various concentrations on day 4, 8, and 12 post infection, respectively. At a concentration as lower as 0.02 µg/mL (~0.8 nM), both Ab32 and AB33 could inhibit HIV-1 RT activity by 75% on day 12 post infection of the monocytes.

5. Binding of the Selected Human Monoclonal Antibody to CCR5

The ability of the human monoclonal scFv antibodies Ab32 and Ab33 to bind with their target protein was confirmed by Western blot. Briefly, lysate of human macrophage (expressing CCR5) was separated on SDS-PAGE, and transferred to nitrocellulose membrane. The membrane was then probed either with the scFv selected in the above-described process (Ab32 and Ab33) or positive control antibody (murine monoclonal antibody 2D7 from Pharmingen, San Diego), or a negative control (Ab16, an anti-p53 scFv antibody). The positive control (MAb 2D7) blot was then probed with goat anti-mouse IgG conjugated with HRP (horse radish peroxidase). The scFv-probed blots were incubated with mouse anti-HSV tag antibody followed by goat anti-mouse IgG conjugated HRP. The CCR5 band was then detected with ECL (Enhanced Chemilluminence, from Amersham-Pharmacia).

Figure 12:
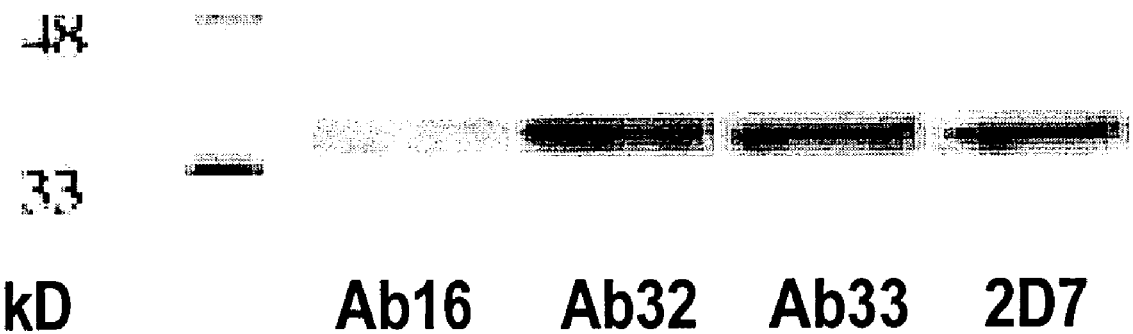
FIG. 12 shows a Western blot of CCR5 expressed by human macrophage probed by scFv against human CCR5 Loop 6.

FIG. 12 shows the Western blot of CCR5 expressed by human macrophage probed by Ab32 and Ab33. As shown in FIG. 12, both Ab32 and Ab33 were capable of binding to CCR5, just like the positive control MAb 2D7. In contrast, a non-specific scFv antibody elicited against human p53 protein, AB16, is incapable of binding to CCR5.

These results indicate that the monoclonal scFv antibodies selected against a peptide fragment derived from CCR5 Loop 6 can specifically recognize and bind to human CCR5 in vitro.

6. Inhibition of Chemokine Binding to CCR5 by the Selected Human Monoclonal Antibody The ability of the human monoclonal scFv antibodies Ab32 and Ab33 to bind with their target protein was further validated by conducting competition binding assay using described in Wu et al. (1997) J. Exp. Med. 186:1373–1381. Briefly, human MDMs (monocyte-derived macrophages) were plated in 48-well plates. The attached cells were incubated with antibodies (Ab32, Ab33, or the mouse monoclonal antibody 2D7) at 37° C. for 30 minutes. Radiolabeled human CCR5 ligand, $^{125}$I MIP1-α (Amersham), was added to each well to a final concentration of 100 pM (2 µCi/pmole) and the cultures were incubated at 37° C. for two hours. After removal of the medium, the cultures were washed 3 times with cold PBS buffer. Cells were lysed with 0.3 ml of 1% Triton X-100 in PBS for 30 min at room temperature. Radioactivity in the lysates were measured by a gamma counter (Packard). The results were shown in FIG. 13.

Figure 13:
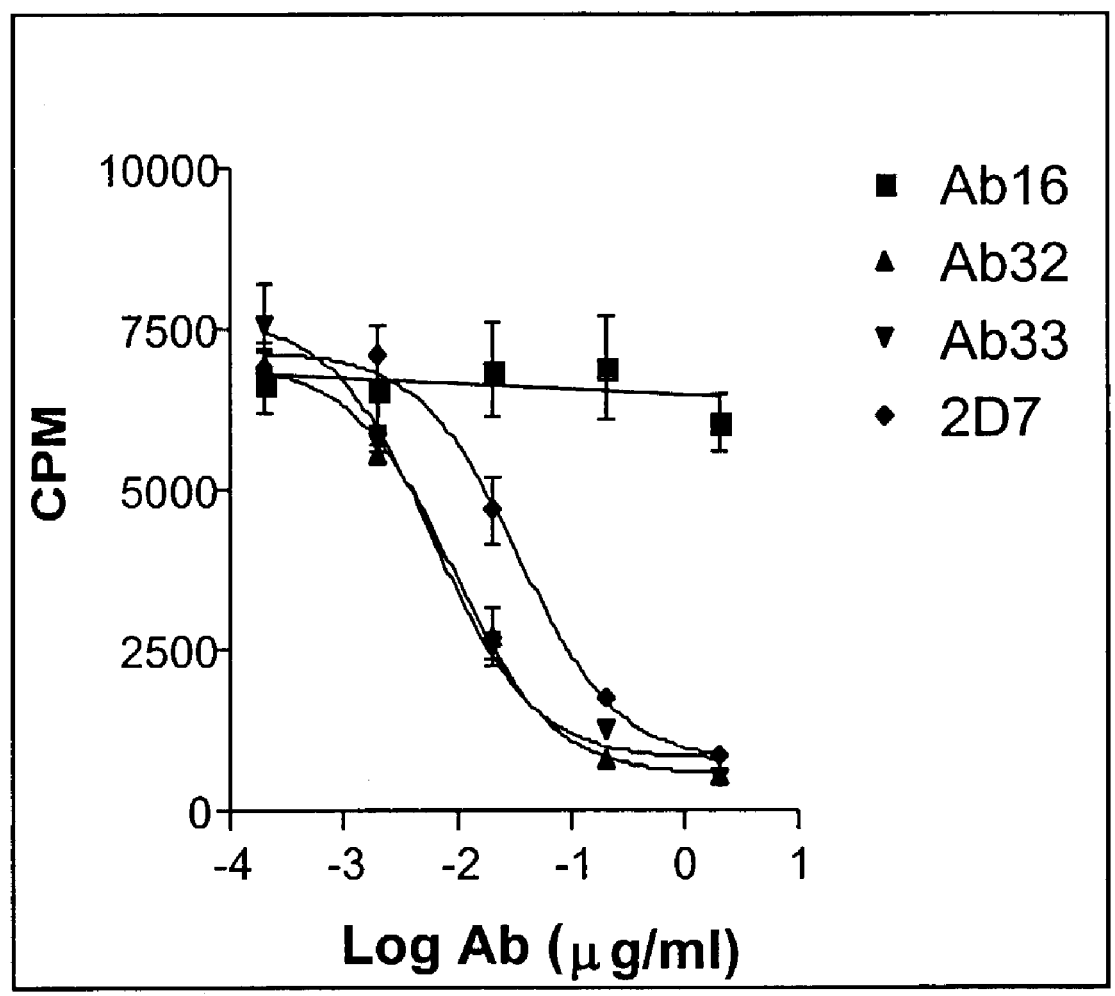
FIG. 13 is a graph showing that two scFv against human CCR5 Loop 6 are both capable of blocking the binding of MIP-1α to CCR5 on human monocyte-derived macrophages.

As shown in FIG. 13, the human monoclonal scFv antibodies Ab32 and Ab33 effectively blocked the binding of $^{125}$I MIP1-α to its cognate receptor CCR5 on human MDMs. Significantly, both Ab32 and Ab33 exhibited slightly stronger binding affinity to human CCR5 than the mouse monoclonal antibody 2D7. In contrast, a non-specific human scFv against human p53, Ab16, could not inhibit the binding of $^{125}$I MIP1-α to CCR5.

Figure 14:
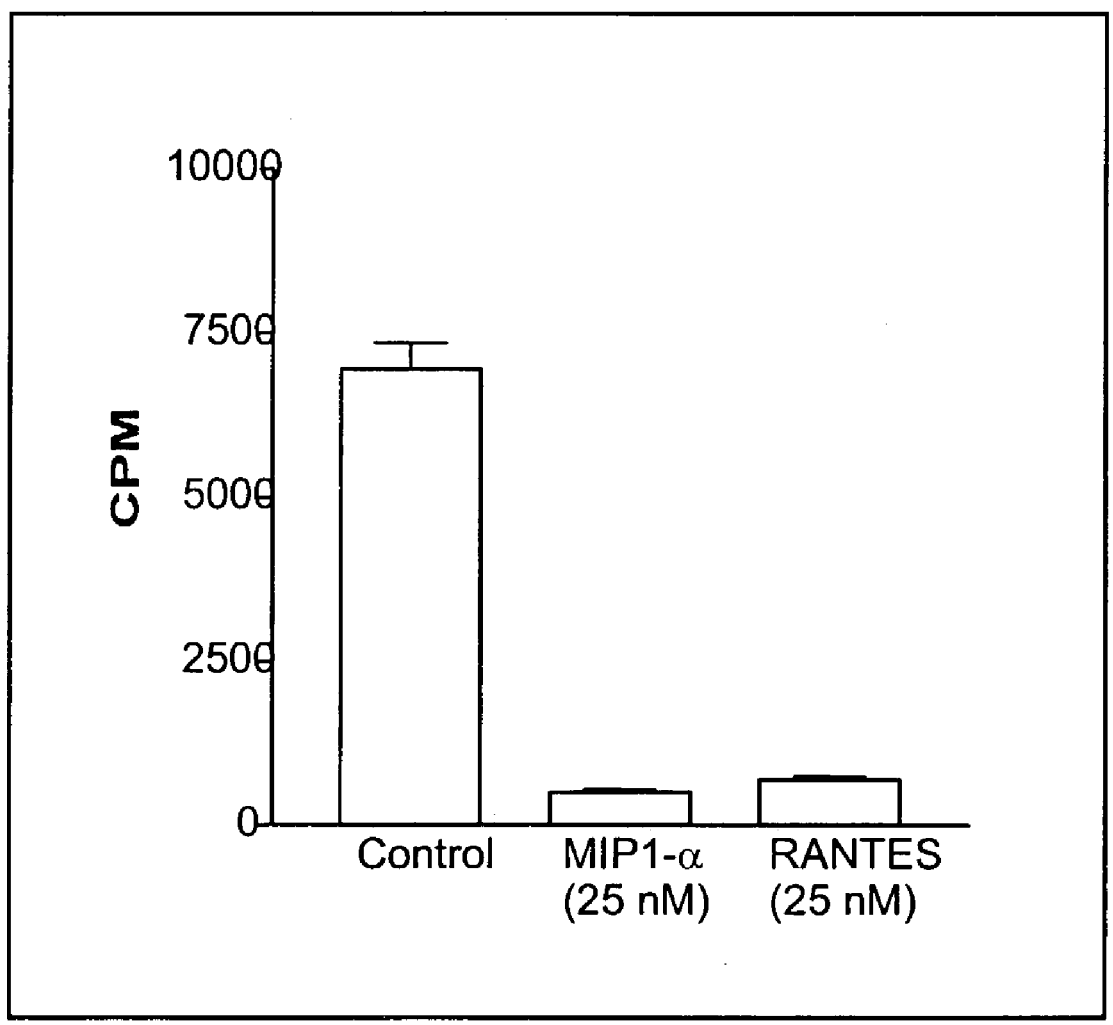
FIG. 14 is a graph showing that non-labeled CCR5 ligands, MIP-1α and RANTES, can compete with radio-labeled MIP-1α in binding with CCR5 on human monocyte-derived macrophages.

To ensure that the results obtained in above-described assay were obtained in a normally-behaving binding assay, non-labeled MIP1-α was used to compete with $^{125}$I MIP1-α for binding to CCR5. As shown in FIG. 14, MIP1-α could compete with $^{125}$I MIP1-α for binding to CCR5 at a concentration of 25 nm. Similarly, another cognate ligand of human CCR5, RANTES, could also compete with $^{125}$I MIP1-α for binding to CCR5 at a concentration of 25 nm. These results indicate that the radio-labeled human CCR5 ligand, $^{125}$I MIP1-α, did bind to its cognate receptor CCR5 on human MDMs and the binding could be inhibited by the human monoclonal scFv antibodies Ab32 and Ab33 selected using the method of the present invention.

7. Construction of a Yeast Expression Vector Encoding Peptide Fragments Derived from Human CXCR4

In one embodiment of the present invention, the last extracellular loop of human CXCR4, loop 6, was used as the target peptide fragment for eliciting monoclonal antibodies against CXCR4 in yeast. The cDNA encoding CXCR4 loop 6 was amplified from human leukocyte Quick-clone cDNA (purchased from BD-Clontech, Cat. # 7182-1) using primers 13.12.G and 13.12.H.

[SEQ ID NO: 55]
13.12.G  5'-GGA GAA TTC ATCGACTCCTTCATCCTCCTG

[SEQ ID NO: 56]
13.12.H  5'-CGC GGA TCC TTA AGCTAGGGCCTCGGTGATGGA

The PCR product was cloned into Eco RI/Bam HI sites of pGBK-T7, resulting a plasmid (designated as pG88) encoding CXCR4 loop 6 with the Gal4 DNA binding domain fused at its carboxy terminus. The DNA sequence of the coding region of human CXCR4 loop6 is as follows:

[SEQ ID NO; 57]
5'ATCGACTCCTTCATCCTCCTGGAAATCATCAAGCAAGGGTGTGAGTTT

GAGAACACTGTGCACAAGTGGATTTCCATCACCGAGGCCCTAGCT-3'

The amino acid sequence encoded by the above DNA sequence is as follows:
IDSFILLEIIKQGCEFENTVHKWISITEALA
[SEQ ID NO: 58]

8. Screening of a Human scFv Antibody Library Against Human CXCR4 Loop 6 in Yeast Two-Hybrid System Plasmid DNA of pG88 was transformed into yeast cells of strain AH109. Transformed cells were mated with a fully human scFv library as described in Section 1 of "EXAMPLE" above. The mated cells were selected on medium SD/-Leu-Trp-His-Ade. Cells grown on the selection medium were assayed for β-gal activities. Non-specific scFv clones were ruled out by assaying with control bait plasmids (pGBK-T7 and pGBK-Lam). DNA sequences of the scFv inserts from the human CXCR4 loop 6-specific clones were determined. Two clones with complete scFv inserts were obtained. These two scFv clones were designated Ab124 and Ab125. Their nucleotide and amino acid sequences are listed in FIG. 15.

9. Inhibition of SDF-1 Induced Chemotaxis by the Selected Human Monoclonal Antibodies Against CXCR4 in Human Breast Cancer Cells ScFv clones encoding Ab124 and Ab125 were cloned into E. coli expression vector pET27b(+) (Novagen) to facilitate expression of these 2 scFv antibodies. ScFv proteins were expressed and purified from the periplasmic space of the bacteria. The ability of these selected anti-CXCR4 scFv antibodies to inhibit SDF-1 induced chemotaxis was determined by using an assay described in Harvath L, et al. (1980) J Immunol Methods. 37:39–45. SDF-1 (Stromal cell Derived Factor-1) is a ligand of CXCR4 which can cause chemotaxis of certain cell types, including the breast cancer cell line MDA-MB-231. In the present invention, the selected antibodies were tested for their ability to inhibit SDF-1 induced chemotaxis in MDA-MB-231 cells.

Cells of breast cancer cell line MDA-MB-231 were incubated with i) medium only, ii) mouse anti-CXCR4 monoclonal antibody (R&D System), iii) isotype control mouse monoclonal antibody, iv) control scFv Ab16, v) scFv Ab124, or vi) scFv Ab125, followed by the chemotaxis assay. Numbers of MDA-MB-231 cells that migrated toward the chamber containing SDF-1 were counted under a microscope.

Figure 16:
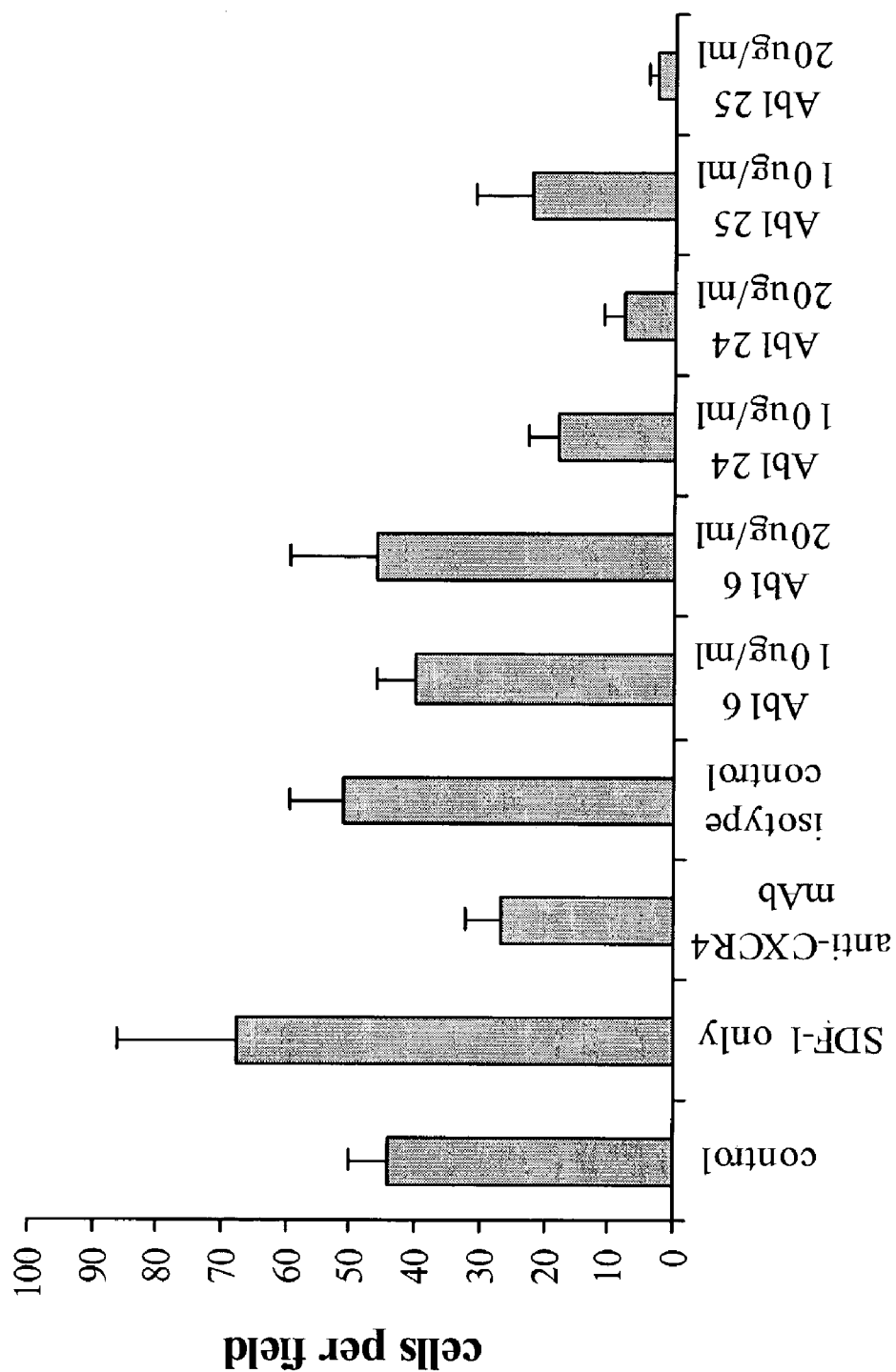
FIG. 16 is a graph showing that single chain antibodies Ab124 and Ab125 can inhibit SDF-1 induced chemotaxis in human breast cancer line MDA-MB-231.

The results are shown in FIG. 16. These results demonstrate that Ab124 and Ab125 can block SDF-1 induced chemotaxis in the breast cancer cell line MDA-MB-231, suggesting that the Ab124 and Ab125 can bind to CXCR4 and block the function of a CXCR4 ligand, SDF-1.

What is claimed is:

1. An isolated antibody that specifically binds to human CXCR4, wherein the antibody comprises a heavy chain variable region of SEQ ID NO: 60 and a light chain variable region of SEQ ID NO: 61, or a heavy chain variable region of SEQ ID NO: 63 and a light chain variable region of SEQ ID NO: 64.

2. The antibody of claim 1, wherein the antibody is a monoclonal antibody.

3. The antibody of claim 2, wherein the monoclonal antibody is a single chain antibody.

4. The antibody of claim 3, wherein the single chain antibody is encoded by DNA SEQ ID NO: 59 or 62.

5. The antibody of claim 1, wherein the antibody specifically binds to loop 6 of human CXCR4 of SEQ ID NO: 58.

* * * * *

SEQUENCE LISTING

<160> NUMBER OF SEQ ID NOS: 64

<210> SEQ ID NO 1
<211> LENGTH: 352
<212> TYPE: PRT
<213> ORGANISM: Homo sapiens

<400> SEQUENCE: 1

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

```
Ala Val Val His Ala Val Phe Ala Leu Lys Ala Arg Thr Val Thr Phe
        130                 135                 140
Gly Val Val Thr Ser Val Ile Thr Trp Val Val Ala Val Phe Ala Ser
145                 150                 155                 160
Leu Pro Gly Ile Ile Phe Thr Arg Ser Gln Lys Glu Gly Leu His Tyr
                165                 170                 175
Thr Cys Ser Ser His Phe Pro Tyr Ser Gln Tyr Gln Phe Trp Lys Asn
                180                 185                 190
Phe Gln Thr Leu Lys Ile Val Ile Leu Gly Leu Val Leu Pro Leu Leu
            195                 200                 205
Val Met Val Ile Cys Tyr Ser Gly Ile Leu Lys Thr Leu Leu Arg Cys
        210                 215                 220
Arg Asn Glu Lys Lys Arg His Arg Ala Val Arg Leu Ile Phe Thr Ile
225                 230                 235                 240
Met Ile Val Tyr Phe Leu Phe Trp Ala Pro Tyr Asn Ile Val Leu Leu
                245                 250                 255
Leu Asn Thr Phe Gln Glu Phe Phe Gly Leu Asn Asn Cys Ser Ser Ser
            260                 265                 270
Asn Arg Leu Asp Gln Ala Met Gln Val Thr Glu Thr Leu Gly Met Thr
        275                 280                 285
His Cys Cys Ile Asn Pro Ile Ile Tyr Ala Phe Val Gly Glu Lys Phe
290                 295                 300
Arg Asn Tyr Leu Leu Val Phe Phe Gln Lys His Ile Ala Lys Arg Phe
305                 310                 315                 320
Cys Lys Cys Cys Ser Ile Phe Gln Gln Glu Ala Pro Glu Arg Ala Ser
                325                 330                 335
Ser Val Tyr Thr Arg Ser Thr Gly Glu Gln Glu Ile Ser Val Gly Leu
                340                 345                 350
```

```
<210> SEQ ID NO 2
<211> LENGTH: 17
<212> TYPE: PRT
<213> ORGANISM: Homo sapiens

<400> SEQUENCE: 2

Gln Glu Phe Phe Gly Leu Asn Asn Cys Ser Ser Ser Asn Arg Leu Asp
1               5                   10                  15
Gln

<210> SEQ ID NO 3
<211> LENGTH: 32
<212> TYPE: PRT
<213> ORGANISM: Homo sapiens

<400> SEQUENCE: 3

Thr Arg Ser Gln Lys Glu Gly Leu His Tyr Thr Cys Ser Ser His Phe
1               5                   10                  15
Pro Tyr Ser Gln Tyr Gln Phe Trp Lys Asn Phe Gln Thr Leu Lys Ile
            20                  25                  30

<210> SEQ ID NO 4
<211> LENGTH: 20
<212> TYPE: PRT
<213> ORGANISM: Artificial Sequence
<220> FEATURE:
<223> OTHER INFORMATION: G4S Linker

<400> SEQUENCE: 4
```

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 5
<211> LENGTH: 60
<212> TYPE: DNA
<213> ORGANISM: Artificial Sequence
<220> FEATURE:
<223> OTHER INFORMATION: DNA of G4S Linker

<400> SEQUENCE: 5
ggcggtggtg gatcaggcgg cggaggatct ggcggaggtg gcagcggtgg tggaggcagt    60

<210> SEQ ID NO 6
<211> LENGTH: 60
<212> TYPE: DNA
<213> ORGANISM: Artificial Sequence
<220> FEATURE:
<223> OTHER INFORMATION: 5' Homologous Sequence

<400> SEQUENCE: 6
accccaccaa acccaaaaaa agagatctgt atggcttacc catacgatgt tccagattac    60

<210> SEQ ID NO 7
<211> LENGTH: 57
<212> TYPE: DNA
<213> ORGANISM: Artificial Sequence
<220> FEATURE:
<223> OTHER INFORMATION: 3' Homologous Sequence

<400> SEQUENCE: 7
gagatggtgc acgatgcaca gttgaagtga acttgcgggg ttttcagta tctacga      57

<210> SEQ ID NO 8
<211> LENGTH: 36
<212> TYPE: PRT
<213> ORGANISM: Homo sapiens

<400> SEQUENCE: 8

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu
            35
```

<210> SEQ ID NO 9
<211> LENGTH: 32
<212> TYPE: PRT
<213> ORGANISM: Homo sapiens

<400> SEQUENCE: 9

```
Thr Arg Ser Gln Lys Glu Gly Leu His Tyr Thr Cys Ser Ser His Phe
1               5                   10                  15

Pro Tyr Ser Gln Tyr Gln Phe Trp Lys Asn Phe Gln Thr Leu Lys Ile
            20                  25                  30
```

<210> SEQ ID NO 10
<211> LENGTH: 30
<212> TYPE: DNA
<213> ORGANISM: Artificial Sequence

```
<220> FEATURE:
<223> OTHER INFORMATION: Primer

<400> SEQUENCE: 10
ggagaattcg attatcaagt gtcaagtcca                              30

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
cgcggatcct tagagcggag gcaggaggcg g                            31

<210> SEQ ID NO 12
<211> LENGTH: 29
<212> TYPE: DNA
<213> ORGANISM: Artificial Sequence
<220> FEATURE:
<223> OTHER INFORMATION: Primer

<400> SEQUENCE: 12
ggagaattca ccagatctca aaaagaagg                               29

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
cgcggatcct tatatcttta atgtctggaa att                          33

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
caggaattct ttggcctgaa t                                       21

<210> SEQ ID NO 15
<211> LENGTH: 31
<212> TYPE: DNA
<213> ORGANISM: Artificial Sequence
<220> FEATURE:
<223> OTHER INFORMATION: Primer

<400> SEQUENCE: 15
cgcggatcct cagcagtgcg tcatcccaag a                            31

<210> SEQ ID NO 16
<211> LENGTH: 759
<212> TYPE: DNA
<213> ORGANISM: Artificial Sequence
<220> FEATURE:
<223> OTHER INFORMATION: Clone 15.186.35

<400> SEQUENCE: 16
caggttacct tgaaggagtc tggtcctacg ttggtgaaac ccacacagac cctcacgctg    60
```

```
acctgcacct tgtctgggtt ctcactcagc actagtggag tgagtgtggg ctggatccgt    120
cagcccccag gaaaggccct tgagtggctt gcaagcataa attggaatga tgataagtgc    180
tacagcccat ctctgaaaag caggctcacc atcaccaagg acaccccaa aaaccaggtg     240 gtccttgcaa tgagcaacat ggaccctgcg acacagcca catattcctg tgcactcgat     300 atgcccccc atgatagtgg cccgcaatct tttgatgctt ctgatgtctg gggcccaggg     360
acaatggtca ccgtctcttc aggcggtggt ggatcaggcg gcggaggatc tggcggaggt    420
ggcagcggtg gtggaggcag ttcctatgag ctgatgcagc taccctcagt gtccgtgtcc    480
ccaggacaga cagccagcat cacctgctct ggagataatt tggggataaa atatgcctgc    540
tggtatcaac agaagccagg ccggtcccct gtgctggtca tttatggaga taacaagcgg    600
ccctcaggga tccctgagcg attctctggc tccaactctg gaacacagc cactctgacc     660 atcagcggga cccaggctat ggatgaggct gactattact gtcaggcgtg ggacaccagc    720
actgctgtct tcggaactgg gaccaagctc accgtccta                            759
```

<210> SEQ ID NO 17
<211> LENGTH: 253
<212> TYPE: PRT
<213> ORGANISM: Artificial Sequence
<220> FEATURE:
<223> OTHER INFORMATION: Clone 15.186.35

<400> SEQUENCE: 17

```
Gln Val Thr Leu Lys Glu Ser Gly Pro Thr Leu Val Lys Pro Thr Gln
 1               5                  10                  15

Thr Leu Thr Leu Thr Cys Thr Leu Ser Gly Phe Ser Leu Ser Thr Ser
            20                  25                  30

Gly Val Ser Val Gly Trp Ile Arg Gln Pro Pro Gly Lys Ala Leu Glu
        35                  40                  45

Trp Leu Ala Ser Ile Asn Trp Asn Asp Asp Lys Cys Tyr Ser Pro Ser
    50                  55                  60

Leu Lys Ser Arg Leu Thr Ile Thr Lys Asp Thr Pro Lys Asn Gln Val
65                  70                  75                  80

Val Leu Ala Met Ser Asn Met Asp Pro Ala Asp Thr Ala Thr Tyr Ser
                85                  90                  95

Cys Ala Leu Asp Met Pro Pro His Asp Ser Gly Pro Gln Ser Phe Asp
            100                 105                 110

Ala Ser Asp Val Trp Gly Pro Gly Thr Met Val Thr Val Ser Ser Gly
        115                 120                 125

Gly Gly Ser Gly Gly Gly Gly Ser Gly Gly Gly Gly Ser Gly Gly
    130                 135                 140

Gly Gly Ser Ser Tyr Glu Leu Met Gln Leu Pro Ser Val Ser Val Ser
145                 150                 155                 160

Pro Gly Gln Thr Ala Ser Ile Thr Cys Ser Gly Asp Asn Leu Gly Asp
                165                 170                 175

Lys Tyr Ala Cys Trp Tyr Gln Gln Lys Pro Gly Arg Ser Pro Val Leu
            180                 185                 190

Val Ile Tyr Gly Asp Asn Lys Arg Pro Ser Gly Ile Pro Glu Arg Phe
        195                 200                 205

Ser Gly Ser Asn Ser Gly Asn Thr Ala Thr Leu Thr Ile Ser Gly Thr
    210                 215                 220

Gln Ala Met Asp Glu Ala Asp Tyr Tyr Cys Gln Ala Trp Asp Thr Ser
225                 230                 235                 240
```

Thr Ala Val Phe Gly Thr Gly Thr Lys Leu Thr Val Leu
            245                 250

<210> SEQ ID NO 18
<211> LENGTH: 762
<212> TYPE: DNA
<213> ORGANISM: Artificial Sequence
<220> FEATURE:
<223> OTHER INFORMATION: Clone 15.150.11

<400> SEQUENCE: 18

| | | | | | |
|---|---|---|---|---|---|
| caggtgcagc | tgcaggagtc | gggcccagga | ctggtgaagc | cttcggagac | cctgtccctc | 60 |
| acttgcactg | tctctggtgg | ctccatcggt | catgactact | ggagctggat | acggcagccc | 120 |
| ccaggggagg | gactggagtg | gattggtttc | atcttcttcg | atgggagcac | caactacaac | 180 |
| ccctccctca | acggtcgagt | caccatctca | ctcgacacgt | cgaagaatca | gctctccctg | 240 |
| aggctgacct | ctgtgaccgc | tgcggacacg | gccgtgtatt | tctgtgcgag | actaaagggg | 300 |
| gcgtggttat | tgtctgaacc | cccttacttc | agctccgacg | gcatggacgt | ctggggccaa | 360 |
| gggaccacgg | tcaccgtccc | ctcaggcggt | ggtggatcag | gcggcggagg | atctggcgga | 420 |
| ggtggcagcg | gtggtggagg | cagtaatttt | atgctgactc | agccccctc | agcgtctggg | 480 |
| acccccgggc | agagggtcag | catctcttgt | tctgggagca | gctccgacat | cggaagtaat | 540 |
| actgtaaact | ggtaccagca | actcccagga | acggccccca | aactcctcat | ctatagtaat | 600 |
| aatcagcggc | cctcaggggt | ccctgaccga | ttctctggct | tcaagtctgg | cacctcagcc | 660 |
| tccctggtca | tcagtggcct | ccagtctgag | gatgaggctg | attattattg | tgcagcatgg | 720 |
| gatgagagcc | tgaatggtgt | ggtgttcggc | ggaggaccaa | gg | | 762 |

<210> SEQ ID NO 19
<211> LENGTH: 254
<212> TYPE: PRT
<213> ORGANISM: Artificial Sequence
<220> FEATURE:
<223> OTHER INFORMATION: Clone 15.150.11

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly His Asp
            20                  25                  30

Tyr Trp Ser Trp Ile Arg Gln Pro Pro Gly Glu Gly Leu Glu Trp Ile
        35                  40                  45

Gly Phe Ile Phe Phe Asp Gly Ser Thr Asn Tyr Asn Pro Ser Leu Asn
    50                  55                  60

Gly Arg Val Thr Ile Ser Leu Asp Thr Ser Lys Asn Gln Leu Ser Leu
65                  70                  75                  80

Arg Leu Thr Ser Val Thr Ala Ala Asp Thr Ala Val Tyr Phe Cys Ala
                85                  90                  95

Arg Leu Lys Gly Ala Trp Leu Leu Ser Glu Pro Pro Tyr Phe Ser Ser
            100                 105                 110

Asp Gly Met Asp Val Trp Gly Gln Gly Thr Thr Val Thr Val Pro Ser
        115                 120                 125

Gly Gly Gly Gly Ser Gly Gly Gly Ser Gly Gly Gly Ser Gly
    130                 135                 140

Gly Gly Gly Ser Asn Phe Met Leu Thr Gln Pro Pro Ser Ala Ser Gly
145                 150                 155                 160

```
Thr Pro Gly Gln Arg Val Ser Ile Ser Cys Ser Gly Ser Ser Ser Asp
                165                 170                 175

Ile Gly Ser Asn Thr Val Asn Trp Tyr Gln Gln Leu Pro Gly Thr Ala
            180                 185                 190

Pro Lys Leu Leu Ile Tyr Ser Asn Asn Gln Arg Pro Ser Gly Val Pro
        195                 200                 205

Asp Arg Phe Ser Gly Phe Lys Ser Gly Thr Ser Ala Ser Leu Val Ile
    210                 215                 220

Ser Gly Leu Gln Ser Glu Asp Glu Ala Asp Tyr Tyr Cys Ala Ala Trp
225                 230                 235                 240

Asp Glu Ser Leu Asn Gly Val Val Phe Gly Gly Pro Arg
                245                 250
```

<210> SEQ ID NO 20
<211> LENGTH: 750
<212> TYPE: DNA
<213> ORGANISM: Artificial Sequence
<220> FEATURE:
<223> OTHER INFORMATION: Clone 15.150.12

<400> SEQUENCE: 20

```
caggtgcagc tacagcagtg gggcgcagga ctgttgaagt cttggggaac cctgtccctc    60
acctgcgctg tctctggtgc gtcgtttagt ggttattatt ggagctggat ccgccagccc   120
ccagggaagg ggctggagtg gattggggag atcaatcatc gtggaagcac tacctacaac   180
ccgtccctcg acggtcgagt caccatatca ttagacacat ctaccaacca gatctccctt   240
aaactgacct ctatgaccgc cgcggacacg gccgtgtatt actgtgcgag acagtggct    300
ggtactagtg actactgggg ccagggaacc ctggtcaccg tttcctcagg gagtgcatcc   360
gccccaacgg gcggtggtgg atcaggcggc ggaggatctg gcggaggtgg cagcggtggt   420
ggaggcagta aaacgacact cacgcagtct ccagcattca tgtcagcgac tccaggagac   480
aaagtcagca tctcctgcaa agccagccga acgttgatg atgatgtgaa ctggtaccaa   540
cagagaccag gagaagctcc tattttcatt attgaagatg ctactactct cgttcctgga   600
atctcacctc gattcagtgg cagcgggtat ggaaccgatt ttaccctcac aattaataac   660
atcgattctg aggatgctgc atattatttc tgtctacaac atgataattt cccgctcacc   720
ttcggcggag ggaccaaggt ggagatcaaa                                    750
```

<210> SEQ ID NO 21
<211> LENGTH: 250
<212> TYPE: PRT
<213> ORGANISM: Artificial Sequence
<220> FEATURE:
<223> OTHER INFORMATION: Clone 15.150.12

<400> SEQUENCE: 21

```
Gln Val Gln Leu Gln Gln Trp Gly Ala Gly Leu Leu Lys Ser Trp Gly
1               5                   10                  15

Thr Leu Ser Leu Thr Cys Ala Val Ser Gly Ala Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Thr Thr Tyr Asn Pro Ser Leu Asp
    50                  55                  60

Gly Arg Val Thr Ile Ser Leu Asp Thr Ser Thr Asn Gln Ile Ser Leu
65                  70                  75                  80
```

-continued

Lys Leu Thr Ser Met Thr Ala Ala Asp Thr Ala Val Tyr Tyr Cys Ala
                85                  90                  95
Arg Thr Val Ala Gly Thr Ser Asp Tyr Trp Gly Gln Gly Thr Leu Val
            100                 105                 110
Thr Val Ser Ser Gly Ser Ala Ser Ala Pro Thr Gly Gly Gly Ser
        115                 120                 125
Gly Gly Gly Gly Ser Gly Gly Gly Ser Gly Gly Gly Ser Lys
    130                 135                 140
Thr Thr Leu Thr Gln Ser Pro Ala Phe Met Ser Ala Thr Pro Gly Asp
145                 150                 155                 160
Lys Val Ser Ile Ser Cys Lys Ala Ser Arg Asp Val Asp Asp Val
                165                 170                 175
Asn Trp Tyr Gln Gln Arg Pro Gly Glu Ala Pro Ile Phe Ile Ile Glu
            180                 185                 190
Asp Ala Thr Thr Leu Val Pro Gly Ile Ser Pro Arg Phe Ser Gly Ser
        195                 200                 205
Gly Tyr Gly Thr Asp Phe Thr Leu Thr Ile Asn Asn Ile Asp Ser Glu
    210                 215                 220
Asp Ala Ala Tyr Tyr Phe Cys Leu Gln His Asp Asn Phe Pro Leu Thr
225                 230                 235                 240
Phe Gly Gly Gly Thr Lys Val Glu Ile Lys
                245                 250

<210> SEQ ID NO 22
<211> LENGTH: 759
<212> TYPE: DNA
<213> ORGANISM: Artificial Sequence
<220> FEATURE:
<223> OTHER INFORMATION: Clone 15.150.24

<400> SEQUENCE: 22

```
caggtcacct tgaaggagtc tggtcctacg ctggtgaaac ccacacagac cctcacgctg      60
acctgcacct tctctgggtt ctcactcaga actactggag agggtgtggg ctgggtccgt     120
cagcccccag gaaaggccct ggaatggctt gcactcattt attgggatga tgataagcgc     180
tacagcccat ctctgaagag caggctcacc atcaccaagg acacctccaa aaagcaggtg     240
gtccttacaa tgaccaacgt ggacccagcg acacagcca cctattactg tacacacgag     300
caatactatt atgatactag tggtcagcca tactactttg acttctgggg ccagggcacc     360
ctggtcaccg tctcctcagg cggtggtgga tcaggcggcg aggatctggc ggaggtggc     420
agcggtggtg gaggcagtaa catccaggtg acccagtctc catcctccct gtctgcatct     480
gtaggagaca gagtcaccat gacttgccgg gcgagtcagg acattaggaa gaatttaaat     540
tggtatcagc aaaaaccagg gaaagcccct aaggtcctga tctacgatgc atccgatttg     600
gaaacaggga tcccatcaag gttcagtgga agtggatctg ggacagattt tatcctcacc     660
atcagcagcc tgcagcctga agatattgca acatactact gtcaacagtc tgattattta     720
ccgctcactt tcggcggagg gaccaaagtg gatatcaaa                            759
```

<210> SEQ ID NO 23
<211> LENGTH: 253
<212> TYPE: PRT
<213> ORGANISM: Artificial Sequence
<220> FEATURE:
<223> OTHER INFORMATION: Clone 15.150.24

<400> SEQUENCE: 23

-continued

```
Gln Val Thr Leu Lys Glu Ser Gly Pro Thr Leu Val Lys Pro Thr Gln
  1               5                  10                  15
Thr Leu Thr Leu Thr Cys Thr Phe Ser Gly Phe Ser Leu Arg Thr Thr
             20                  25                  30
Gly Glu Gly Val Gly Trp Val Arg Gln Pro Pro Gly Lys Ala Leu Glu
         35                  40                  45
Trp Leu Ala Leu Ile Tyr Trp Asp Asp Asp Lys Arg Tyr Ser Pro Ser
 50                  55                  60
Leu Lys Ser Arg Leu Thr Ile Thr Lys Asp Thr Ser Lys Lys Gln Val
 65                  70                  75                  80
Val Leu Thr Met Thr Asn Val Asp Pro Ala Asp Thr Ala Thr Tyr Tyr
                 85                  90                  95
Cys Thr His Glu Gln Tyr Tyr Tyr Asp Thr Ser Gly Gln Pro Tyr Tyr
            100                 105                 110
Phe Asp Phe Trp Gly Gln Gly Thr Leu Val Thr Val Ser Ser Gly Gly
        115                 120                 125
Gly Gly Ser Gly Gly Gly Gly Ser Gly Gly Gly Ser Gly Gly Gly Gly
    130                 135                 140
Gly Ser Asn Ile Gln Val Thr Gln Ser Pro Ser Ser Leu Ser Ala Ser
145                 150                 155                 160
Val Gly Asp Arg Val Thr Met Thr Cys Arg Ala Ser Gln Asp Ile Arg
                165                 170                 175
Lys Asn Leu Asn Trp Tyr Gln Gln Lys Pro Gly Lys Ala Pro Lys Val
            180                 185                 190
Leu Ile Tyr Asp Ala Ser Asp Leu Glu Thr Gly Ile Pro Ser Arg Phe
        195                 200                 205
Ser Gly Ser Gly Ser Gly Thr Asp Phe Ile Leu Thr Ile Ser Ser Leu
    210                 215                 220
Gln Pro Glu Asp Ile Ala Thr Tyr Tyr Cys Gln Gln Ser Asp Tyr Leu
225                 230                 235                 240
Pro Leu Thr Phe Gly Gly Gly Thr Lys Val Asp Ile Lys
                245                 250
```

<210> SEQ ID NO 24
<211> LENGTH: 759
<212> TYPE: DNA
<213> ORGANISM: Artificial Sequence
<220> FEATURE:
<223> OTHER INFORMATION: Clone 15.186.35 Variant

<400> SEQUENCE: 24

```
caggtcacct tgaaggagtc tggtcctacg ttggtgaaac ccacacagac cctcacgctg     60
acctgcacct tgtctgggtt ctcactcagc actagtggag tgagtgtggg ctggatccgt    120
cagcccccag gaaaggccct tgagtggctt gcaagcataa attggaatga tgataagtgc    180
tacagcccat ctctgaaaag caggctcacc atcaccaagg acacccccaa aaaccaggtg    240
gtccttgcaa tgagcaacat ggaccctgcg gacacagcca catattcctg tgcactcgat    300
atgcccccc atgatagtgg cccgcaatct tttgatgctt ctgatgtctg ggcccaggg     360
acaatggtca ccgtctcttc aggcggtggt ggatcaggcg gcggaggatc tggcggaggt    420
ggcagcggtg gtggaggcag ttcctatgag ctgatgcagc taccctcagt gtccgtgtcc    480
ccaggacaga cagccagcat cacctgctct ggagataatt tggggataa atatgcctgc    540
tggtatcaac agaagccagg ccgtcccct gtgctggtca tttatggaga taacaagcgg    600
ccctcaggga tccctgagcg attctctggc tccaactctg gaacacagc cactctgacc    660
```

```
atcagcggga cccaggctat ggatgaggct gactattact gtcaggcgtg ggacaccagc    720
actgctgtct tcggaactgg gaccaagctc accgtccta                           759
```

<210> SEQ ID NO 25
<211> LENGTH: 253
<212> TYPE: PRT
<213> ORGANISM: Artificial Sequence
<220> FEATURE:
<223> OTHER INFORMATION: Clone 15.186.35 Variant

<400> SEQUENCE: 25

```
Gln Val Thr Leu Lys Glu Ser Gly Pro Thr Leu Val Lys Pro Thr Gln
1               5                   10                  15

Thr Leu Thr Leu Thr Cys Thr Leu Ser Gly Phe Ser Leu Ser Thr Ser
            20                  25                  30

Gly Val Ser Val Gly Trp Ile Arg Gln Pro Pro Gly Lys Ala Leu Glu
        35                  40                  45

Trp Leu Ala Ser Ile Asn Trp Asn Asp Asp Lys Cys Tyr Ser Pro Ser
    50                  55                  60

Leu Lys Ser Arg Leu Thr Ile Thr Lys Asp Thr Pro Lys Asn Gln Val
65                  70                  75                  80

Val Leu Ala Met Ser Asn Met Asp Pro Ala Asp Thr Ala Thr Tyr Ser
                85                  90                  95

Cys Ala Leu Asp Met Pro Pro His Asp Ser Gly Pro Gln Ser Phe Asp
            100                 105                 110

Ala Ser Asp Val Trp Gly Pro Gly Thr Met Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Ser Tyr Glu Leu Met Gln Leu Pro Ser Val Ser Val Ser
145                 150                 155                 160

Pro Gly Gln Thr Ala Ser Ile Thr Cys Ser Gly Asp Asn Leu Gly Asp
                165                 170                 175

Lys Tyr Ala Cys Trp Tyr Gln Gln Lys Pro Gly Arg Ser Pro Val Leu
            180                 185                 190

Val Ile Tyr Gly Asp Asn Lys Arg Pro Ser Gly Ile Pro Glu Arg Phe
        195                 200                 205

Ser Gly Ser Asn Ser Gly Asn Thr Ala Thr Leu Thr Ile Ser Gly Thr
    210                 215                 220

Gln Ala Met Asp Glu Ala Asp Tyr Tyr Cys Gln Ala Trp Asp Thr Ser
225                 230                 235                 240

Thr Ala Val Phe Gly Thr Gly Thr Lys Leu Thr Val Leu
                245                 250
```

<210> SEQ ID NO 26
<211> LENGTH: 774
<212> TYPE: DNA
<213> ORGANISM: Artificial Sequence
<220> FEATURE:
<223> OTHER INFORMATION: Clone 15.150.11 Variant

<400> SEQUENCE: 26

```
caggtgcagc tgcaggagtc gggcccagga ctggtgaagc cttcggagac cctgtccctc    60
acttgcactg tctctggtgg ctccatcggt catgactact ggagctggat acggcagccc   120
ccaggggagg gactggagtg gattggtttc atcttcttcg atgggagcac caactacaac   180
```

-continued

```
ccctccctca acggtcgagt caccatctca ctcgacacgt cgaagaatca gctctccctg    240
aggctgacct ctgtgaccgc tgcggacacg gccgtgtatt tctgtgcgag actaaagggg    300
gcgtggttat tgtctgaacc cccttacttc agctccgacg gcatggacgt ctggggccaa    360
gggaccacgg tcaccgtctc ctcaggcggt ggtggatcag gcggcggagg atctggcgga    420
ggtggcagcg gtggtggagg cagtaatttt atgctgactc agccccctc agcgtctggg     480 accccggc agagggtcag catctcttgt tctgggagca gctccgacat cggaagtaat     540
actgtaaact ggtaccagca actcccagga acggccccca aactcctcat ctatagtaat    600
aatcagcggc cctcagggt ccctgaccga ttctctggct tcaagtctgg cacctcagcc     660
tccctggtca tcagtggcct ccagtctgag gatgaggctg attattattg tgcagcatgg    720
gatgagagcc tgaatggtgt ggtgttcggc ggaggaacca aggtgaccgt ccta          774
```

<210> SEQ ID NO 27
<211> LENGTH: 258
<212> TYPE: PRT
<213> ORGANISM: Artificial Sequence
<220> FEATURE:
<223> OTHER INFORMATION: Clone 15.150.11 Variant

<400> SEQUENCE: 27

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Gly His Asp
             20                  25                  30

Tyr Trp Ser Trp Ile Arg Gln Pro Pro Gly Glu Gly Leu Glu Trp Ile
         35                  40                  45

Gly Phe Ile Phe Phe Asp Gly Ser Thr Asn Tyr Asn Pro Ser Leu Asn
     50                  55                  60

Gly Arg Val Thr Ile Ser Leu Asp Thr Ser Lys Asn Gln Leu Ser Leu
 65                  70                  75                  80

Arg Leu Thr Ser Val Thr Ala Ala Asp Thr Ala Val Tyr Phe Cys Ala
                 85                  90                  95

Arg Leu Lys Gly Ala Trp Leu Leu Ser Glu Pro Pro Tyr Phe Ser Ser
            100                 105                 110

Asp Gly Met Asp Val Trp Gly Gln Gly Thr Thr Val Thr Val Ser Ser
        115                 120                 125

Gly Gly Gly Gly Ser Gly Gly Gly Ser Gly Gly Gly Ser Gly
    130                 135                 140

Gly Gly Gly Ser Asn Phe Met Leu Thr Gln Pro Pro Ser Ala Ser Gly
145                 150                 155                 160

Thr Pro Gly Gln Arg Val Ser Ile Ser Cys Ser Gly Ser Ser Ser Asp
                165                 170                 175

Ile Gly Ser Asn Thr Val Asn Trp Tyr Gln Gln Leu Pro Gly Thr Ala
            180                 185                 190

Pro Lys Leu Leu Ile Tyr Ser Asn Asn Gln Arg Pro Ser Gly Val Pro
        195                 200                 205

Asp Arg Phe Ser Gly Phe Lys Ser Gly Thr Ser Ala Ser Leu Val Ile
    210                 215                 220

Ser Gly Leu Gln Ser Glu Asp Glu Ala Asp Tyr Tyr Cys Ala Ala Trp
225                 230                 235                 240

Asp Glu Ser Leu Asn Gly Val Val Phe Gly Gly Gly Thr Lys Val Thr
                245                 250                 255

Val Leu
```

<210> SEQ ID NO 28
<211> LENGTH: 750
<212> TYPE: DNA
<213> ORGANISM: Artificial Sequence
<220> FEATURE:
<223> OTHER INFORMATION: Clone 15.150.12 Variant

<400> SEQUENCE: 28

```
caggtgcagc tacagcagtg gggcgcagga ctgttgaagt cttggggaac cctgtccctc      60
acctgcgctg tctctggtgc gtcgtttagt ggttattatt ggagctggat ccgccagccc     120
ccagggaagg ggctggagtg gattggggag atcaatcatc gtggaagcac tacctacaac     180
ccgtccctcg acggtcgagt caccatatca ttagacacat ctaccaacca gatctccctt     240
aaactgacct ctatgaccgc cgcggacacg gccgtgtatt actgtgcgag gacagtggct     300
ggtactagtg actactgggg ccagggaacc ctggtcaccg tttcctcagg agtgcatcc      360
gccccaacgg gcggtggtgg atcaggcggc ggaggatctg gcggaggtgg cagcggtggt     420
ggaggcagtg aaacgacact cacgcagtct ccagcattca tgtcagcgac tccaggagac     480
aaagtcagca tctcctgcaa agccagccga gacgttgatg atgatgtgaa ctggtaccaa     540
cagagaccag gagaagctcc tattttcatt attgaagatg ctactactct cgttcctgga     600
atctcacctc gattcagtgg cagcgggtat ggaaccgatt ttaccctcac aattaataac     660
atcgattctg aggatgctgc atattatttc tgtctacaac atgataattt cccgctcacc     720
ttcggcggag ggaccaaggt ggagatcaaa                                      750
```

<210> SEQ ID NO 29
<211> LENGTH: 250
<212> TYPE: PRT
<213> ORGANISM: Artificial Sequence
<220> FEATURE:
<223> OTHER INFORMATION: Clone 15.150.12 Variant

<400> SEQUENCE: 29

```
Gln Val Gln Leu Gln Gln Trp Gly Ala Gly Leu Leu Lys Ser Trp Gly
1               5                   10                  15

Thr Leu Ser Leu Thr Cys Ala Val Ser Gly Ala Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Thr Thr Tyr Asn Pro Ser Leu Asp
    50                  55                  60

Gly Arg Val Thr Ile Ser Leu Asp Thr Ser Thr Asn Gln Ile Ser Leu
65                  70                  75                  80

Lys Leu Thr Ser Met Thr Ala Ala Asp Thr Ala Val Tyr Tyr Cys Ala
                85                  90                  95

Arg Thr Val Ala Gly Thr Ser Asp Tyr Trp Gly Gln Gly Thr Leu Val
            100                 105                 110

Thr Val Ser Ser Gly Ser Ala Ser Ala Pro Thr Gly Gly Gly Ser
        115                 120                 125

Gly Gly Gly Gly Ser Gly Gly Gly Ser Gly Gly Gly Ser Glu
    130                 135                 140

Thr Thr Leu Thr Gln Ser Pro Ala Phe Met Ser Ala Thr Pro Gly Asp
145                 150                 155                 160

Lys Val Ser Ile Ser Cys Lys Ala Ser Arg Asp Val Asp Asp Val
                165                 170                 175
```

Asn Trp Tyr Gln Gln Arg Pro Gly Glu Ala Pro Ile Phe Ile Ile Glu
                180                 185                 190

Asp Ala Thr Thr Leu Val Pro Gly Ile Ser Pro Arg Phe Ser Gly Ser
            195                 200                 205

Gly Tyr Gly Thr Asp Phe Thr Leu Thr Ile Asn Asn Ile Asp Ser Glu
        210                 215                 220

Asp Ala Ala Tyr Tyr Phe Cys Leu Gln His Asp Asn Phe Pro Leu Thr
225                 230                 235                 240

Phe Gly Gly Gly Thr Lys Val Glu Ile Lys
            245                 250

<210> SEQ ID NO 30
<211> LENGTH: 759
<212> TYPE: DNA
<213> ORGANISM: Artificial Sequence
<220> FEATURE:
<223> OTHER INFORMATION: Clone 15.150.24 Variant

<400> SEQUENCE: 30
caggtcacct tgaaggagtc tggtcctacg ctggtgaaac ccacacagac cctcacgctg      60
acctgcacct tctctgggtt ctcactcaga actactggag agggtgtggg ctgggtccgt     120
cagcccccag gaaaggccct ggaatggctt gcactcattt attgggatga tgataagcgc     180
tacagcccat ctctgaagag caggctcacc atcaccaagg acacctccaa aaagcaggtg     240
gtccttacaa tgaccaacgt ggacccagcg gacacagcca cctattactg tacacacgag     300
caatactatt atgatactag tggtcagcca tactactttg acttctgggg ccagggcacc     360
ctggtcaccg tctcctcagg cggtggtgga tcaggcggcg aggatctggc cggaggtggc     420
agcggtggtg gaggcagtaa catccaggtg acccagtctc catcctccct gtctgcatct     480
gtaggagaca gagtcaccat gacttgccgg gcgagtcagg acattaggaa gaatttaaat     540
tggtatcagc aaaaaccagg gaaagcccct aaggtcctga tctacgatgc atccgatttg     600
gaaacaggga tcccatcaag gttcagtgga agtggatctg ggacagattt tatcctcacc     660
atcagcagcc tgcagcctga agatattgca acatactact gtcaacagtc tgattattta     720
ccgctcactt tcggcggagg gaccaaagtg gatatcaaa                            759

<210> SEQ ID NO 31
<211> LENGTH: 253
<212> TYPE: PRT
<213> ORGANISM: Artificial Sequence
<220> FEATURE:
<223> OTHER INFORMATION: Clone 15.150.24 Variant

<400> SEQUENCE: 31

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Arg Thr Thr
            20                  25                  30

Gly Glu Gly Val Gly Trp Val Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Lys Gln Val
65                  70                  75                  80

Val Leu Thr Met Thr Asn Val Asp Pro Ala Asp Thr Ala Thr Tyr Tyr
                85                  90                  95

Cys Thr His Glu Gln Tyr Tyr Tyr Asp Thr Ser Gly Gln Pro Tyr Tyr
            100                 105                 110

Phe Asp Phe Trp Gly Gln Gly Thr Leu Val Thr Val Ser Ser Gly Gly
        115                 120                 125

Gly Gly Ser Gly Gly Gly Ser Gly Gly Gly Ser Gly Gly Gly
    130                 135                 140

Gly Ser Asn Ile Gln Val Thr Gln Ser Pro Ser Ser Leu Ser Ala Ser
145                 150                 155                 160

Val Gly Asp Arg Val Thr Met Thr Cys Arg Ala Ser Gln Asp Ile Arg
                165                 170                 175

Lys Asn Leu Asn Trp Tyr Gln Gln Lys Pro Gly Lys Ala Pro Lys Val
                180                 185                 190

Leu Ile Tyr Asp Ala Ser Asp Leu Glu Thr Gly Ile Pro Ser Arg Phe
            195                 200                 205

Ser Gly Ser Gly Ser Gly Thr Asp Phe Ile Leu Thr Ile Ser Ser Leu
        210                 215                 220

Gln Pro Glu Asp Ile Ala Thr Tyr Tyr Cys Gln Gln Ser Asp Tyr Leu
225                 230                 235                 240

Pro Leu Thr Phe Gly Gly Gly Thr Lys Val Asp Ile Lys
                245                 250

<210> SEQ ID NO 32
<211> LENGTH: 9
<212> TYPE: PRT
<213> ORGANISM: Artificial Sequence
<220> FEATURE:
<223> OTHER INFORMATION: VH CDR2
<220> FEATURE:
<221> NAME/KEY: MISC_FEATURE
<222> LOCATION: (4)..(4)
<223> OTHER INFORMATION: X = Asparagine or Threonine

<400> SEQUENCE: 32

Gly Ser Thr Xaa Tyr Asn Pro Ser Leu
1               5

<210> SEQ ID NO 33
<211> LENGTH: 5
<212> TYPE: PRT
<213> ORGANISM: Artificial Sequence
<220> FEATURE:
<223> OTHER INFORMATION: VL CDR2
<220> FEATURE:
<221> NAME/KEY: MISC_FEATURE
<222> LOCATION: (3)..(4)
<223> OTHER INFORMATION: X3 = Asparagine or Threonine
      X4 = Threonine or Aspartic acid

<400> SEQUENCE: 33

Asp Ala Xaa Xaa Leu
1               5

<210> SEQ ID NO 34
<211> LENGTH: 127
<212> TYPE: PRT
<213> ORGANISM: Homo sapiens

<400> SEQUENCE: 34

Gln Val Thr Leu Lys Glu Ser Gly Pro Thr Leu Val Lys Pro Thr Gln
1               5                   10                  15

Thr Leu Thr Leu Thr Cys Thr Leu Ser Gly Phe Ser Leu Ser Thr Ser
            20                  25                  30

```
Gly Val Ser Val Gly Trp Ile Arg Gln Pro Pro Gly Lys Ala Leu Glu
            35                  40                  45

Trp Leu Ala Ser Ile Asn Trp Asn Asp Asp Lys Cys Tyr Ser Pro Ser
 50                  55                  60

Leu Lys Ser Arg Leu Thr Ile Thr Lys Asp Thr Pro Lys Asn Gln Val
 65                  70                  75                  80

Val Leu Ala Met Ser Asn Met Asp Pro Ala Asp Thr Ala Thr Tyr Ser
                 85                  90                  95

Cys Ala Leu Asp Met Pro Pro His Asp Ser Gly Pro Gln Ser Phe Asp
                100                 105                 110

Ala Ser Asp Val Trp Gly Pro Gly Thr Met Val Thr Val Ser Ser
                115                 120                 125
```

<210> SEQ ID NO 35
<211> LENGTH: 106
<212> TYPE: PRT
<213> ORGANISM: Homo sapiens

<400> SEQUENCE: 35

```
Ser Tyr Glu Leu Met Gln Leu Pro Ser Val Ser Val Ser Pro Gly Gln
 1               5                  10                  15

Thr Ala Ser Ile Thr Cys Ser Gly Asp Asn Leu Gly Asp Lys Tyr Ala
                 20                  25                  30

Cys Trp Tyr Gln Gln Lys Pro Gly Arg Ser Pro Val Leu Val Ile Tyr
             35                  40                  45

Gly Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Thr Ser Thr Ala Val
                 85                  90                  95

Phe Gly Thr Gly Thr Lys Leu Thr Val Leu
                100                 105
```

<210> SEQ ID NO 36
<211> LENGTH: 126
<212> TYPE: PRT
<213> ORGANISM: Homo sapiens

<400> SEQUENCE: 36

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Gly His Asp
                 20                  25                  30

Tyr Trp Ser Trp Ile Arg Gln Pro Pro Gly Glu Gly Leu Glu Trp Ile
             35                  40                  45

Gly Phe Ile Phe Phe Asp Gly Ser Thr Asn Tyr Asn Pro Ser Leu Asn
 50                  55                  60

Gly Arg Val Thr Ile Ser Leu Asp Thr Ser Lys Asn Gln Leu Ser Leu
 65                  70                  75                  80

Arg Leu Thr Ser Val Thr Ala Ala Asp Thr Ala Val Tyr Phe Cys Ala
                 85                  90                  95

Arg Leu Lys Gly Ala Trp Leu Leu Ser Glu Pro Pro Tyr Phe Ser Ser
                100                 105                 110

Asp Gly Met Asp Val Trp Gly Gln Gly Thr Thr Val Thr Val
                115                 120                 125
```

<210> SEQ ID NO 37
<211> LENGTH: 104
<212> TYPE: PRT
<213> ORGANISM: Homo sapiens

<400> SEQUENCE: 37

```
Asn Phe Met Leu Thr Gln Pro Pro Ser Ala Ser Gly Thr Pro Gly Gln
1               5                   10                  15

Arg Val Ser Ile Ser Cys Ser Gly Ser Ser Asp Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Phe Lys Ser Gly Thr Ser Ala Ser Leu Val Ile Ser Gly Leu Gln
65                  70                  75                  80

Ser Glu Asp Glu Ala Asp Tyr Tyr Cys Ala Ala Trp Asp Glu Ser Leu
                85                  90                  95

Asn Gly Val Val Phe Gly Gly Gly
            100
```

<210> SEQ ID NO 38
<211> LENGTH: 116
<212> TYPE: PRT
<213> ORGANISM: Homo sapiens

<400> SEQUENCE: 38

```
Gln Val Gln Leu Gln Gln Trp Gly Ala Gly Leu Leu Lys Ser Trp Gly
1               5                   10                  15

Thr Leu Ser Leu Thr Cys Ala Val Ser Gly Ala Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Arg Gly Ser Thr Thr Tyr Asn Pro Ser Leu Asp
    50                  55                  60

Gly Arg Val Thr Ile Ser Leu Asp Thr Ser Thr Asn Gln Ile Ser Leu
65                  70                  75                  80

Lys Leu Thr Ser Met Thr Ala Ala Asp Thr Ala Val Tyr Tyr Cys Ala
                85                  90                  95

Arg Thr Val Ala Gly Thr Ser Asp Tyr Trp Gly Gln Gly Thr Leu Val
            100                 105                 110

Thr Val Ser Ser
        115
```

<210> SEQ ID NO 39
<211> LENGTH: 106
<212> TYPE: PRT
<213> ORGANISM: Homo sapiens

<400> SEQUENCE: 39

```
Thr Thr Leu Thr Gln Ser Pro Ala Phe Met Ser Ala Thr Pro Gly Asp
1               5                   10                  15

Lys Val Ser Ile Ser Cys Lys Ala Ser Arg Asp Val Asp Asp Val
            20                  25                  30

Asn Trp Tyr Gln Gln Arg Pro Gly Glu Ala Pro Ile Phe Ile Ile Glu
            35                  40                  45
```

```
Asp Ala Thr Thr Leu Val Pro Gly Ile Ser Pro Arg Phe Ser Gly Ser
 50                  55                  60
Gly Tyr Gly Thr Asp Phe Thr Leu Thr Ile Asn Asn Ile Asp Ser Glu
 65                  70                  75                  80
Asp Ala Ala Tyr Tyr Phe Cys Leu Gln His Asp Asn Phe Pro Leu Thr
                 85                  90                  95
Phe Gly Gly Gly Thr Lys Val Glu Ile Lys
            100                 105
```

<210> SEQ ID NO 40
<211> LENGTH: 126
<212> TYPE: PRT
<213> ORGANISM: Homo sapiens

<400> SEQUENCE: 40

```
Gln Val Thr Leu Lys Glu Ser Gly Pro Thr Leu Val Lys Pro Thr Gln
 1               5                  10                  15
Thr Leu Thr Leu Thr Cys Thr Phe Ser Gly Phe Ser Leu Arg Thr Thr
                 20                  25                  30
Gly Glu Gly Val Gly Trp Val Arg Gln Pro Pro Gly Lys Ala Leu Glu
             35                  40                  45
Trp Leu Ala Leu Ile Tyr Trp Asp Asp Lys Arg Tyr Ser Pro Ser
 50                  55                  60
Leu Lys Ser Arg Leu Thr Ile Thr Lys Asp Thr Ser Lys Lys Gln Val
 65                  70                  75                  80
Val Leu Thr Met Thr Asn Val Asp Pro Ala Asp Thr Ala Thr Tyr Tyr
                 85                  90                  95
Cys Thr His Glu Gln Tyr Tyr Tyr Asp Thr Ser Gly Gln Pro Tyr Tyr
            100                 105                 110
Phe Asp Phe Trp Gly Gln Gly Thr Leu Val Thr Val Ser Ser
            115                 120                 125
```

<210> SEQ ID NO 41
<211> LENGTH: 107
<212> TYPE: PRT
<213> ORGANISM: Homo sapiens

<400> SEQUENCE: 41

```
Asn Ile Gln Val Thr Gln Ser Pro Ser Ser Leu Ser Ala Ser Val Gly
 1               5                  10                  15
Asp Arg Val Thr Met Thr Cys Arg Ala Ser Gln Asp Ile Arg Lys Asn
                 20                  25                  30
Leu Asn Trp Tyr Gln Gln Lys Pro Gly Lys Ala Pro Lys Val Leu Ile
             35                  40                  45
Tyr Asp Ala Ser Asp Leu Glu Thr Gly Ile Pro Ser Arg Phe Ser Gly
 50                  55                  60
Ser Gly Ser Gly Thr Asp Phe Ile Leu Thr Ile Ser Ser Leu Gln Pro
 65                  70                  75                  80
Glu Asp Ile Ala Thr Tyr Tyr Cys Gln Gln Ser Asp Tyr Leu Pro Leu
                 85                  90                  95
Thr Phe Gly Gly Gly Thr Lys Val Asp Ile Lys
            100                 105
```

<210> SEQ ID NO 42
<211> LENGTH: 5
<212> TYPE: PRT
<213> ORGANISM: Artificial Sequence
<220> FEATURE:

<223> OTHER INFORMATION: Linker Sequence

<400> SEQUENCE: 42

Gly Gly Gly Gly Ser
1               5

<210> SEQ ID NO 43
<211> LENGTH: 21
<212> TYPE: PRT
<213> ORGANISM: Homo sapiens

<400> SEQUENCE: 43

Arg Leu Lys Gly Ala Trp Leu Leu Ser Glu Pro Pro Tyr Phe Ser Ser
1               5                   10                  15

Asp Gly Met Asp Val
            20

<210> SEQ ID NO 44
<211> LENGTH: 9
<212> TYPE: PRT
<213> ORGANISM: Homo sapiens

<400> SEQUENCE: 44

Arg Thr Val Ala Gly Thr Ser Asp Tyr
1               5

<210> SEQ ID NO 45
<211> LENGTH: 17
<212> TYPE: PRT
<213> ORGANISM: Homo sapiens

<400> SEQUENCE: 45

His Glu Gln Tyr Tyr Tyr Asp Thr Ser Gly Gln Pro Tyr Tyr Phe Asp
1               5                   10                  15

Phe

<210> SEQ ID NO 46
<211> LENGTH: 11
<212> TYPE: PRT
<213> ORGANISM: Homo sapiens

<400> SEQUENCE: 46

Ala Ala Trp Asp Glu Ser Leu Asn Gly Val Val
1               5                   10

<210> SEQ ID NO 47
<211> LENGTH: 9
<212> TYPE: PRT
<213> ORGANISM: Homo sapiens

<400> SEQUENCE: 47

Leu Gln His Asp Asn Phe Pro Leu Thr
1               5

<210> SEQ ID NO 48
<211> LENGTH: 9
<212> TYPE: PRT
<213> ORGANISM: Homo sapiens

<400> SEQUENCE: 48

Gln Gln Ser Asp Tyr Leu Pro Leu Thr
1               5

```
<210> SEQ ID NO 49
<211> LENGTH: 30
<212> TYPE: DNA
<213> ORGANISM: Artificial Sequence
<220> FEATURE:
<223> OTHER INFORMATION: Primer

<400> SEQUENCE: 49
ggagaattcg attatcaagt gtcaagtcca                              30

<210> SEQ ID NO 50
<211> LENGTH: 31
<212> TYPE: DNA
<213> ORGANISM: Artificial Sequence
<220> FEATURE:
<223> OTHER INFORMATION: Primer

<400> SEQUENCE: 50
cgcggatcct tagagcggag gcaggaggcg g                            31

<210> SEQ ID NO 51
<211> LENGTH: 29
<212> TYPE: DNA
<213> ORGANISM: Artificial Sequence
<220> FEATURE:
<223> OTHER INFORMATION: Primer

<400> SEQUENCE: 51
ggagaattca ccagatctca aaaagaagg                               29

<210> SEQ ID NO 52
<211> LENGTH: 33
<212> TYPE: DNA
<213> ORGANISM: Artificial Sequence
<220> FEATURE:
<223> OTHER INFORMATION: Primer

<400> SEQUENCE: 52
cgcggatcct tatatcttta atgtctggaa att                          33

<210> SEQ ID NO 53
<211> LENGTH: 21
<212> TYPE: DNA
<213> ORGANISM: Artificial Sequence
<220> FEATURE:
<223> OTHER INFORMATION: Primer

<400> SEQUENCE: 53
caggaattct ttggcctgaa t                                       21

<210> SEQ ID NO 54
<211> LENGTH: 31
<212> TYPE: DNA
<213> ORGANISM: Artificial Sequence
<220> FEATURE:
<223> OTHER INFORMATION: Primer

<400> SEQUENCE: 54
cgcggatcct cagcagtgcg tcatcccaag a                            31

<210> SEQ ID NO 55
<211> LENGTH: 30
<212> TYPE: DNA
<213> ORGANISM: Artificial Sequence
<220> FEATURE:
<223> OTHER INFORMATION: Primer 13.12.G
```

<210> SEQ ID NO 56
<211> LENGTH: 33
<212> TYPE: DNA
<213> ORGANISM: Artificial Sequence
<220> FEATURE:
<223> OTHER INFORMATION: Primer 13.12.H

<400> SEQUENCE: 56
cgcggatcct taagctaggg cctcggtgat gga               33

<210> SEQ ID NO 57
<211> LENGTH: 93
<212> TYPE: DNA
<213> ORGANISM: Homo sapiens

<400> SEQUENCE: 57
atcgactcct tcatcctcct ggaaatcatc aagcaagggt gtgagtttga gaacactgtg     60
cacaagtgga tttccatcac cgaggcccta gct                                  93

<210> SEQ ID NO 58
<211> LENGTH: 31
<212> TYPE: PRT
<213> ORGANISM: Homo sapiens

<400> SEQUENCE: 58

Ile Asp Ser Phe Ile Leu Leu Glu Ile Ile Lys Gln Gly Cys Glu Phe
1               5                   10                  15

Glu Asn Thr Val His Lys Trp Ile Ser Ile Thr Glu Ala Leu Ala
            20                  25                  30

<210> SEQ ID NO 59
<211> LENGTH: 765
<212> TYPE: DNA
<213> ORGANISM: Artificial Sequence
<220> FEATURE:
<223> OTHER INFORMATION: DNA of scFv Ab124

<400> SEQUENCE: 59
caggtgcagc tgcaggagtc cggcccagga ctggtgaagc cttcggagac cctgtccctc     60
acctgcactg tctctggtgg ctccatcagc agtagtagtt actactgggg ctggatccgc    120
cagcccccag ggaaggggct ggagtggatt gggagtatct attatagtgg gagcacctac    180
tacaacccgt ccctcaagag tcgagtcacc atatccgtag acacgtccaa gaaccagttc    240
tccctgaagc tgagctctgt gaccgccgca gacacggctg tgtattactg tgcgagacat    300
attcttacga aagcagctgg ctactggtac ttcgatctct ggggccgtgg caccctggtc    360
accgtctcct ctggcggtgg tggatcaggc ggcgaggat ctggcggagg tggcagcggt     420
ggtggaggca gtcagtctgt tctgattcag cctcgctcag tgtccgggtc tcctggacag    480
tcagtcacca tctcctgcac tggaaccagc agtgatgttg gtggttataa ctatgtctcc    540
tggtaccaac agcacccagg caaagccccc aaactcatga tttatgatgt cagtaagcgg    600
ccctcagggg tccctgatcg cttctctggc tccaagtctg gcaacacggc ctccctgacc    660
atctctgggc tccaggctga ggatgaggct gattattact gctgctcata tgcaggcagc    720
tacagggatt atgtcttcgg aactgggacc aagctgaccg tccta                    765

<210> SEQ ID NO 60
<211> LENGTH: 124
<212> TYPE: PRT
<213> ORGANISM: Artificial Sequence
<220> FEATURE:
<223> OTHER INFORMATION: VH of scFv Ab124

<400> SEQUENCE: 60

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Ile Leu Thr Lys Ala Ala Gly Tyr Trp Tyr Phe Asp
            100                 105                 110

Leu Trp Gly Arg Gly Thr Leu Val Thr Val Ser Ser
        115                 120
```

<210> SEQ ID NO 61
<211> LENGTH: 111
<212> TYPE: PRT
<213> ORGANISM: Artificial Sequence
<220> FEATURE:
<223> OTHER INFORMATION: VL of scFv Ab124

<400> SEQUENCE: 61

```
Gln Ser Val Leu Ile Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Arg Asp Tyr Val Phe Gly Thr Gly Thr Lys Leu Thr Val Leu
            100                 105                 110
```

<210> SEQ ID NO 62
<211> LENGTH: 828
<212> TYPE: DNA
<213> ORGANISM: Artificial Sequence
<220> FEATURE:
<223> OTHER INFORMATION: DNA of scFv Ab125

<400> SEQUENCE: 62

```
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg gctggagtg gattggggaa atcaatcata gtggaagcac caactacaac      180
```

```
ccgtccctca agagtcgagt caccatatca gtagacacgt ccaaaaacca attctccctg      240
aagctgagct ctgtgaccgc cgcggacacg gctgtgtatt actgtgcgag aggccgacgt      300
agtatagcag ctcgtccgtt ttctttttgat atctggggcc aagggacaat ggtcaccgtc      360
tcttcaggcg gtggtggatc aggcggcaca atggtcaccg tctcttctgg cggtggtgga      420
tcaggcggcg gaggatctgg cggtggtgga tcaggcggcg gaggatctgg cggaggtggc      480
agcggtggtg gaggcagtca gcctgtgctg actcaatcac cctcagcgtc tgggaccccc      540
ggccagaggg tcaccatctc ttgttctgga agcagctcca acatcggaat taatcctgta      600
aactggtacc agcagctccc aggagcggct cccaaactcc tcatctacac tactaatcag      660
cggccctcag gggtccctga ccgattctct gcctccaagt ctggcacctc ggcctccccg      720
gccatcagtg gactccagtc tgcggatgag gctgattatt actgtgcagc gtgggatgac      780
aggctgaatg gtgtggtttt cggcggtggg accaagctca ccgtcctc                  828
```

```
<210> SEQ ID NO 63
<211> LENGTH: 122
<212> TYPE: PRT
<213> ORGANISM: Artificial Sequence
<220> FEATURE:
<223> OTHER INFORMATION: VH of scFv Ab125

<400> SEQUENCE: 63

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Arg Ser Ile Ala Ala Arg Pro Phe Ser Phe Asp Ile Trp
            100                 105                 110

Gly Gln Gly Thr Met Val Thr Val Ser Ser
        115                 120
```

```
<210> SEQ ID NO 64
<211> LENGTH: 110
<212> TYPE: PRT
<213> ORGANISM: Artificial Sequence
<220> FEATURE:
<223> OTHER INFORMATION: VL of scFv Ab125

<400> SEQUENCE: 64

Gln Pro Val Leu Thr Gln Ser Pro Ser Ala Ser Gly Thr Pro Gly Gln
1               5                   10                  15

Arg Val Thr Ile Ser Cys Ser Gly Ser Ser Asn Ile Gly Ile Asn
            20                  25                  30

Pro Val Asn Trp Tyr Gln Gln Leu Pro Gly Ala Ala Pro Lys Leu Leu
        35                  40                  45

Ile Tyr Thr Thr Asn Gln Arg Pro Ser Gly Val Pro Asp Arg Phe Ser
    50                  55                  60
```

-continued

```
Ala Ser Lys Ser Gly Thr Ser Ala Ser Pro Ala Ile Ser Gly Leu Gln
 65                  70                  75                  80

Ser Ala Asp Glu Ala Asp Tyr Tyr Cys Ala Ala Trp Asp Asp Arg Leu
                 85                  90                  95

Asn Gly Val Val Phe Gly Gly Gly Thr Lys Leu Thr Val Leu
            100                 105                 110
```